US009102966B2

(12) United States Patent
Schroven et al.

(10) Patent No.: US 9,102,966 B2
(45) Date of Patent: Aug. 11, 2015

(54) SYNTHESIS OF SIALOOLIGOSACCHARIDE DERIVATIVES

(75) Inventors: Andreas Schroven, Barssel (DE); Elise Champion, Toulouse (FR); Gyula Dekany, Queensland (AU); Christoph Röhrig, Mühlingen (DE); Ioannis Vrasidas, Thessaloniki (GR); Ignacio Figueroa Pérez, Miami, FL (US); Markus Hederos, Svedala (SE); Julien Boutet, La Plaine sur Mer (FR); Ágnes Ágoston, Telki (HU); Piroska Kovács-Pénzes, Jászberény (HU); Ferenc Horváth, Pilisszentkereszt (HU); Christian Risinger, Rottweil (DE); Gergely Pipa, Budapest (HU); Sándor Demkó, Debrecen (HU); Lars Kröger, Hamburg (DE)

(73) Assignee: GLYCOM A/S, KGS, Lyngby (DK)

( * ) Notice: Subject to any disclaimer, the term of this patent is extended or adjusted under 35 U.S.C. 154(b) by 165 days.

(21) Appl. No.: 13/809,794

(22) PCT Filed: Jul. 15, 2011

(86) PCT No.: PCT/EP2011/062184

§ 371 (c)(1), (2), (4) Date: Mar. 15, 2013

(87) PCT Pub. No.: WO2012/007588

PCT Pub. Date: Jan. 19, 2012

(65) Prior Publication Data

US 2013/0171696 A1 Jul. 4, 2013

(30) Foreign Application Priority Data

Jul. 16, 2010 (GB) .................................. 1012036.8
May 13, 2011 (EP) .................................... 11166036

(51) Int. Cl.

| | |
|---|---|
| ***C12N 9/00*** | (2006.01) |
| ***C12P 19/14*** | (2006.01) |
| ***C12P 19/44*** | (2006.01) |
| ***C12P 19/18*** | (2006.01) |
| ***C07H 1/06*** | (2006.01) |
| ***C07H 3/06*** | (2006.01) |
| ***C12P 19/26*** | (2006.01) |

(52) U.S. Cl.

CPC . *C12P 19/14* (2013.01); *C07H 1/06* (2013.01); *C07H 3/06* (2013.01); *C12P 19/18* (2013.01); *C12P 19/26* (2013.01); *C12P 19/44* (2013.01)

(58) Field of Classification Search

CPC ............ C07H 1/06; C07H 3/06; C12N 19/18; C12N 19/26; C12N 19/28; C12N 19/44; C12P 19/26; C12P 19/18; C12P 19/44

See application file for complete search history.

(56) References Cited

U.S. PATENT DOCUMENTS

2008/0306267 A1* 12/2008 Rishel et al. .................... 546/95

FOREIGN PATENT DOCUMENTS

| | | |
|---|---|---|
| WO | 96/32492 | 10/1996 |
| WO | 2011/100979 | 8/2011 |
| WO | 2011/100980 | 8/2011 |
| WO | 2012/113404 | 8/2012 |
| WO | 2012/113405 | 8/2012 |
| WO | 2012/127410 | 9/2012 |
| WO | 2012/155916 | 11/2012 |
| WO | 2012/156897 | 11/2012 |
| WO | 2012/156898 | 11/2012 |

OTHER PUBLICATIONS

Cohen et al. J. Org. Chem. (2000) 65: 6145-6152.*

International Search Report mailed Oct. 31, 2011 in corresponding International Patent Application No. PCT/EP2011/062184.

Angela M. Scheppokat et al., "Enzymatic glycosylation, inhibitor design, and synthesis and formation of glyco-self assembled monolayers for simulation of recognition," European Journal of Cell Biology, vol. 89, pp. 39-52 (2010).

Deepani Indurugalla et al., "Natural sialoside analogues for the determination of enzymatic rate constants," Org. Biomol, Chem., vol. 4, pp. 4453-4459 (2006).

Scott B. Cohen et al., "Synthesis and Characterization of an Anomeric Sulfur Analogue of CMP-Sialic Acid," J. Org. Chem., vol. 65, No. 19, pp. 6145-6152 (2000).

Annie Malleron et al., "Chemoenzymatic synthesis of the 3-sulfated Lewis$^a$ pentasaccharide," Carbohydrate Research, vol. 341, pp. 29-34 (2006).

Mahendra S. Sandbhor et al., "Substrate Recognition of the Membrane-Associated Sialidase NEU3 Requires a Hydrophobic Aglycone," Biochemistry, vol. 50, pp. 6753-6762 (2011).

Milady R. Ninonuevo et al., "A Strategy for Annotating the Human Milk Glycome," J. Agric. Food Chem., vol. 54, No. 20, pp. 7471-7480 (2006).

Mitree M. Ponpipom et al., "Synthesis of Paragloboside Analogs," Tetrahedron Letters, No. 20, pp. 1717-1720 (1978).

Fengyang Yan et al., "Polymer-supported and chemoenzymatic synthesis of the *Neisseria meningitidis* pentasaccharide: a methodological comparison," Carbohydrate Research, vol. 328, pp. 3-16 (2000).

Xian-wei Liu et al., "Characterization and synthetic application of a novel β1,3-galactosyltransferase from *Escherichia coli* 055:1-17," Bioorg, Med. Chem., vol. 17, pp. 4910-4915 (2009).

Anna Rencurosi et al., "Human milk oligosaccharides: an enzymatic protection step simplifies the synthesis of 3'- and 6'-*O*-sialyllactose and their analogues," Carbohydrate Research, vol. 337, pp. 473-483 (2002).

Joachim Thiem et al., "Chemoenzymatic Syntheses of Sialyloligosaccharides with Immobilized Sialidase," Chem. Int. Ed. Engl., vol. 30, No. 11, pp. 1503-1505 (1991).

(Continued)

*Primary Examiner* — Susan Hanley

(74) *Attorney, Agent, or Firm* — Pillsbury Winthrop Shaw Pittman LLP

(57) ABSTRACT

The invention relates to a method for the synthesis of compounds of general formula (1A) and salts thereof wherein one of the R groups is an α-sialyl moiety and the other is H, $X^1$ represents a carbohydrate linker, A is a D-glucopyranosyl unit optionally substituted with fucosyl, $R^1$ is a protecting group that is removable by hydrogenolysis, the integer m is 0 or 1, by a transsialidation reaction.

10 Claims, 1 Drawing Sheet

(56) References Cited

OTHER PUBLICATIONS

Rosalia Agusti et al., "Comparative rates of sialylation by recombinant trans-sialidase and inhibitor properties of synthetic oligosaccharides from *Trypanosoma cruzi* mucins-containing galactofuranose and galactopyranose," Bioorg. Med. Chem., vol. pp. 2611-2616 (2007).

Dirk Schmidt et al., "Sialidase-catalyzed transsialylation using polymer-supported solution-phase techniques," Chem. Commun., pp. 1919-1920 (2000).

Andre Lubineau et al., "Porcine liver (2→3)-α-sialyltransferase: substrate specificity studies and application of the immobilized enzyme to the synthesis of various sialylated oligosaccharide sequences," Carbohydrate Research, vol. 300, pp. 161-167 (1997).

Dirk Schmidt et al., "Chemoenzymatic Synthesis of Sialyl Oligosaccharides with Sialidases Employing Transglycosylation Methodology," J. Org. Chem., vol. 65, No. 25, pp. 8518-8526 (2000).

Gastón Paris et al., "A Sialidase Mutant Displaying *trans*-Sialidase Activity," J. Mol. Biol., vol. 345, pp. 923-934 (2005).

International Search Report mailed Mar. 26, 2012 in International Patent Application No. PCT/DK2012/050060 (International Publication No. WO 2012/113405).

International Search Report mailed May 10, 2011 in International Patent Application No. PCT/DK2011/050052 (International Publication No. WO 2011/100979).

International Search Report mailed Jun. 13, 2012 in International Patent Application No. PCT/IB2012/051314 (International Publication No. WO 2012/127410).

International Search Report mailed Aug. 6, 2012 in International Patent Application No. PCT/DK2012/050170 (International Publication No. WO 2012/155916).

U.S. Office Action dated Nov. 19, 2014 in corresponding U.S. Appl. No. 13/809,829.

Green et al., "Protection for the Hydroxyl Group, Including 1,2- and 1,3-Diols," Protective Groups in Organic Synthesis, 2nd Edition, pp. 48-49 (1991).

* cited by examiner

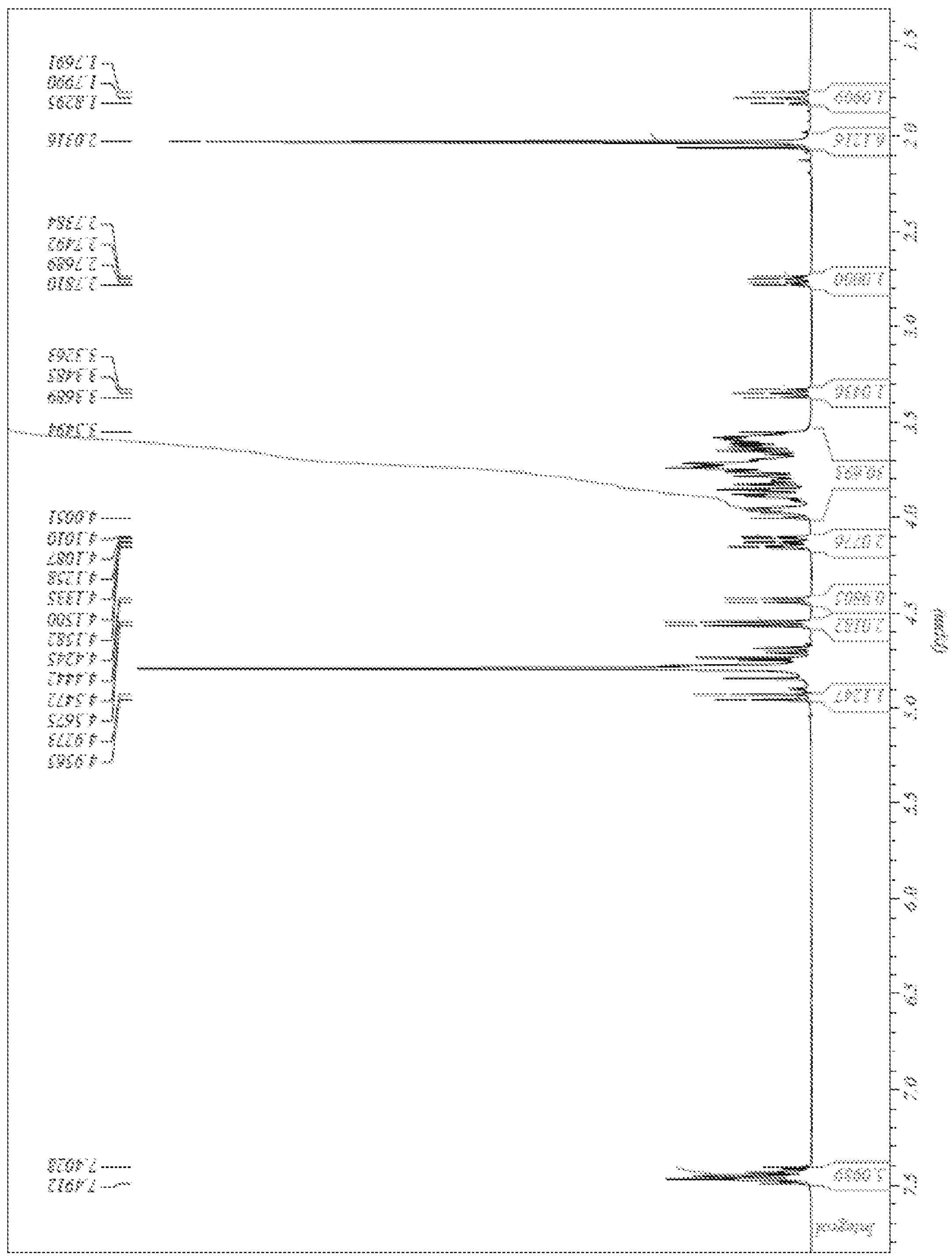
The 400 MHz $^{1}$H-NMR spectrum of benzyl 3'''-*O*-(*N*-acetyl-neuraminosyl)-β-LNnT

SEQUENCE LISTING

<160> NUMBER OF SEQ ID NOS: 11

<210> SEQ ID NO 1
<211> LENGTH: 393
<212> TYPE: PRT
<213> ORGANISM: Bifidobacterium longum subsp. infantis ATCC 15697
<220> FEATURE:
<221> NAME/KEY: source
<222> LOCATION: 1..393
<223> OTHER INFORMATION: /mol_type="protein"
/organism="Bifidobacterium longum subsp. infantis ATCC 15697"

<400> SEQUENCE: 1

```
Met Thr Glu Asn Gly Met Met Asn Thr Asn Asn Thr Val Cys Gly Ala
1               5                   10                  15

Asn His Asp Gly Ala Met Ser Leu Ala Ala Pro Gly Asp Tyr Gly Val
            20                  25                  30

Ala Cys Tyr Arg Ile Pro Ala Leu Ala Glu Ala Pro Asn Gly Trp Ile
        35                  40                  45

Leu Ala Ala Phe Asp Ala Arg Pro His Asn Cys Gln Asp Ala Pro Gln
    50                  55                  60

Ala Asn Ser Ile Val Gln Arg Ile Ser Lys Asp Gly Gly Arg Ser Phe
65                  70                  75                  80

Glu Pro Gln His Val Val Ala Ala Gly His Asp Gly Val Asp Lys Tyr
                85                  90                  95

Gly Tyr Ser Asp Pro Ser Tyr Val Val Asp Arg Gln Thr Gly Glu Val
            100                 105                 110

Phe Leu Phe Phe Val Lys Ser Tyr Asp Ala Gly Phe Gly Thr Ser Gln
        115                 120                 125

Ala Gly Val Asp Pro Ser Ala Arg Glu Val Leu Gln Ala Ala Val Thr
    130                 135                 140

Ser Ser Ile Asp Asn Gly Val Thr Trp Ser Glu Pro Arg Ile Ile Thr
145                 150                 155                 160

Ala Asp Ile Thr Asn Ser Glu Ser Trp Ile Ser Arg Phe Ala Ser Ser
                165                 170                 175

Gly Ala Gly Ile Gln Leu Thr Tyr Gly Glu His Ala Gly Arg Leu Ile
            180                 185                 190

Gln Gln Tyr Thr Ile Lys Glu Leu Asp Gly Arg Tyr Arg Ala Val Ser
        195                 200                 205

Val Phe Ser Asp Asp His Gly Ala Thr Trp His Ala Gly Thr Pro Val
    210                 215                 220

Gly Asp His Met Asp Glu Asn Lys Val Val Glu Leu Ser Asp Gly Arg
225                 230                 235                 240

Val Met Leu Asn Ser Arg Ser Ser Asp Gly Asn Gly Cys Arg Tyr Val
                245                 250                 255

Ala Ile Ser Arg Asp Gly Gly Ala Thr Tyr Gly Pro Val Ile Arg Glu
            260                 265                 270

Thr Gln Leu Pro Asp Pro Glu Asn Asn Ala Gln Ile Ala Arg Ala Phe
        275                 280                 285

Pro Asp Ala Pro Glu Gly Ser Ala Gln Ala Lys Val Leu Leu Tyr Ser
    290                 295                 300

Ser Ser Ser Pro Ser Asp Arg Ile Asp Gly Leu Val Arg Val Ser Ile
305                 310                 315                 320

Asp Asp Gly Lys Thr Trp Ser Ala Gly Arg Arg Phe Thr Thr Gly Pro
                325                 330                 335

Met Ala Tyr Ser Val Ile Ala Ala Leu Ser His Lys Ala Gly Gly Gly
```

```
            340                 345                 350

Tyr Gly Leu Leu Tyr Glu Gly Asp Asn Asn Asn Ile Met Tyr Thr Arg
        355                 360                 365

Ile Ser Leu Asp Trp Leu Asn Gly Gln Leu Asn Val Asp Gly Ile Gly
    370                 375                 380

Gly Phe Pro Leu Ser Gly Glu Gly Gly
385                 390


<210> SEQ ID NO 2
<211> LENGTH: 760
<212> TYPE: PRT
<213> ORGANISM: Bifidobacterium longum subsp. infantis ATCC 15697
<220> FEATURE:
<221> NAME/KEY: source
<222> LOCATION: 1..760
<223> OTHER INFORMATION: /mol_type="protein"
      /organism="Bifidobacterium longum subsp. infantis ATCC 15697"

<400> SEQUENCE: 2

Met Ala Ala Ser Asn Pro Ile Ser Trp Ser Gln Arg Thr Phe Pro Ser
1               5                   10                  15

Pro Glu Gly Thr Ile Ala Cys Arg Phe Arg Ala His Ala Asp Gly Arg
            20                  25                  30

Ile Phe Asp Ala Val Asn Gly Ser Ala Asn Asp Ala Pro Leu Leu Ile
        35                  40                  45

Cys Ala Ile Glu His Asp Ala Leu Arg Val Arg Ala Thr Thr Pro Arg
    50                  55                  60

Gln His Val Asp Phe Asp Ile Glu Asp Thr Thr Gly Ile Ala Asp Gly
65                  70                  75                  80

Ala Met His Thr Phe Ala Leu Thr Phe Gly Glu Phe Gly Thr Arg Val
                85                  90                  95

Tyr Leu Asp Gly Ser Gln Cys Phe Ser Gly Thr Ala Asn Leu Cys Pro
            100                 105                 110

Thr Thr Leu Thr Gly Thr Glu Gly Ser Gly Gln Gly Ala Ile Arg Leu
        115                 120                 125

Ala Gly Pro Ser Ile Asp Val Thr Asp Met Arg Leu His Ala Ile Pro
    130                 135                 140

Leu Thr Ser Glu Ser Ile Ala Ala Leu Thr Pro Arg Pro Ala Pro Asp
145                 150                 155                 160

Ile Asp Phe Ala Ala Ala Gln Leu Ala Pro Arg Asp Val Arg Arg Val
                165                 170                 175

Arg Thr Leu Arg Ser Gly Thr Ile Phe Met His Phe Arg Val Arg Gly
            180                 185                 190

Pro Arg Gln Tyr Gly Thr Leu Leu Ala Ala Gly Glu Arg Gly Glu Glu
        195                 200                 205

Arg Leu Ala Val Ser Ile Asp Asp Asn Gly Ile Thr Met Thr Ala Ala
    210                 215                 220

Asp Gly Leu Tyr Glu Pro Ser Thr Tyr His Ala Arg Gly Ala Trp Asp
225                 230                 235                 240

Asp Gly Arg Trp His Asp Leu Ser Ile Arg Ser Ala Arg Gly Ala Ile
                245                 250                 255

Asp Met Tyr Val Asp Gly Trp His Glu Leu His Gln Ala Gly Gln Val
            260                 265                 270

Phe Phe Gly Asp Trp Pro Gln Leu Asp Glu Val Ala Ile Gly Gln Asn
        275                 280                 285

Thr Glu Gly Val Arg Leu Met Gly Glu Val Arg Asn Gly Gly Val Phe
```

```
    290                 295                 300

Thr Thr Pro Leu Thr Asp Gly Ala Ile Arg Arg Leu Ser Asp Ala Pro
305                 310                 315                 320

Ala Leu Thr Thr Thr Ala Leu Phe Asp Lys Gly Tyr His Gly Ser Val
                325                 330                 335

Ser Tyr Arg Ile Pro Ser Ile Ile Arg Thr Pro His Gly Val Val Val
            340                 345                 350

Ala Gly Ala Asp Gln Arg Thr Ala Ile Ala Asn Asp Ala Pro Asn His
        355                 360                 365

Ile Asn Phe Val Met Arg Arg Ser Leu Asp Gly Gly Arg Thr Trp Leu
    370                 375                 380

Asp Met Gln Thr Val Ile Ala Asn Pro Gly Glu Gly Val Asp Gly Ala
385                 390                 395                 400

Cys Thr Ile Asp Ser Cys Leu Val Cys Asp Glu Arg Asn Gly Arg Leu
                405                 410                 415

Thr Val Leu Ile Asp Arg Phe Ala Gly Gly Val Gly Leu Pro Asn Asn
            420                 425                 430

Thr Pro Gly Thr Gly Val Asp Arg His Gly Arg Pro Cys Leu Tyr Asp
        435                 440                 445

Arg Ala Gly Thr Arg Tyr Val Leu Ala Asp Asp Gly Thr Val Leu Asp
    450                 455                 460

Gly Gly Gly Glu Arg Thr Gly Tyr Arg Val Asp Ala His Gly Asn Val
465                 470                 475                 480

Thr His Glu Gly Arg Ala Ser Gly Asn Ile Tyr Leu Lys Glu Gly Ala
                485                 490                 495

Asp Pro Asp Glu Ser Leu Leu Ile Glu Arg Thr Ser Phe Ile Ile Glu
            500                 505                 510

Leu His Ser Asp Asp Asp Gly Glu Thr Trp Ser Thr Pro Arg Asn Ile
        515                 520                 525

Asn His Met Ile Lys Glu Asp Trp Met His Phe Leu Gly Val Ser Pro
    530                 535                 540

Gly Asn Gly Ile Gln Leu Gln Ala Ser Glu His Arg Gly Arg Leu Leu
545                 550                 555                 560

Val Pro Phe Tyr Cys Thr Gly Ala Ser Leu Lys His Tyr Ser Gly Gly
                565                 570                 575

Ala Leu Ile Ser Asp Asp Gly Gly Asp Thr Trp Arg Arg Gly Ser Met
            580                 585                 590

Ile Asn Asp Gly Arg Ile Val Asn Gly Thr Ala Val Asp Pro Lys Asn
        595                 600                 605

Ile Arg Asp Asp Asp Ala Thr Thr His Glu Ser Val Phe Val Glu Arg
    610                 615                 620

Ala Asp Gly Thr Val Val Cys Phe Phe Arg Asn Gln Asn His Ala Gly
625                 630                 635                 640

Arg Ile Gly Val Ala Leu Ser His Asp Gly Gly Glu Thr Trp Asp Asp
                645                 650                 655

Leu Tyr Phe Asp Lys Asp Val Pro Asp Ile Phe Cys Gln Pro Asn Ala
            660                 665                 670

Val Ala Cys Ala Pro Arg Ser Asp Thr Met Val Phe Ala Asn Ala Ser
        675                 680                 685

Gln Met Leu Pro Tyr Arg Gly Asn Gly Val Leu Arg Leu Ser Leu Asp
    690                 695                 700

Gly Ala Arg Thr Trp Ala Ala His Arg Cys Ile Asn Pro Tyr His Tyr
705                 710                 715                 720
```

```
Gly Tyr Gln Cys Met Thr Met Leu Pro Asp Gly Glu Leu Gly Leu Leu
                725                 730                 735

Trp Glu Arg Glu Thr Ala Gly Leu Tyr Phe Thr Thr Leu Pro Leu Ser
            740                 745                 750

Val Phe Gly Ala Ala Glu Thr His
        755                 760


<210> SEQ ID NO 3
<211> LENGTH: 836
<212> TYPE: PRT
<213> ORGANISM: Bifidobacterium bifidum
<220> FEATURE:
<221> NAME/KEY: source
<222> LOCATION: 1..836
<223> OTHER INFORMATION: /mol_type="protein"
      /organism="Bifidobacterium bifidum"

<400> SEQUENCE: 3

Met Val Arg Ser Thr Lys Pro Ser Leu Leu Arg Arg Leu Gly Ala Leu
1               5                   10                  15

Val Ala Ala Ala Ala Met Leu Val Val Leu Pro Ala Gly Val Ser Thr
            20                  25                  30

Ala Ser Ala Ala Ser Asp Asp Ala Asp Met Leu Thr Val Thr Met Thr
        35                  40                  45

Arg Thr Asp Thr Leu Gly Asp Glu Val Tyr Val Gly Asp Thr Leu Thr
    50                  55                  60

Tyr Ser Phe Thr Asn Thr Asn Asn Thr Ser Ser Ala Phe Thr Ala Phe
65                  70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
            100                 105                 110

Ala Ser His Thr Ile Thr Ala Asp Asp Leu Thr Ala Gly Ser Phe Thr
        115                 120                 125

Pro Arg Thr Val Trp Lys Ala Thr Ser Asp Arg Gly Gly Thr Gln Val
    130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
            180                 185                 190

Tyr Arg Ile Pro Ala Leu Ala Glu Ala Pro Asn Gly Trp Ile Leu Ala
        195                 200                 205

Ala Phe Asp Gln Arg Pro Asn Thr Ala Met Ala Asn Gly Ser Gly Val
    210                 215                 220

Lys Cys Trp Asp Ala Pro Gln Pro Asn Ser Ile Val Gln Arg Ile Ser
225                 230                 235                 240

Lys Asp Gly Gly Lys Ser Trp Thr Pro Ile Gln Tyr Val Ala Gln Gly
                245                 250                 255

Lys Asn Ala Pro Glu Arg Tyr Gly Tyr Ser Asp Pro Ser Tyr Val Val
            260                 265                 270

Asp Glu Glu Thr Gly Glu Ile Phe Leu Phe Phe Val His Ser Tyr Asn
        275                 280                 285

Lys Gly Phe Ala Asp Ser Gln Leu Gly Val Asp Glu Ser Asn Arg Asn
    290                 295                 300
```

```
Val Leu His Ala Val Val Val Ser Ser Lys Asp Asn Gly Glu Thr Trp
305                 310                 315                 320

Ser Lys Pro Arg Asp Ile Thr Ala Asp Ile Thr Lys Gly Tyr Glu Asn
                325                 330                 335

Glu Trp Lys Ser Arg Phe Ala Thr Ser Gly Ala Gly Ile Gln Leu Lys
            340                 345                 350

Tyr Gly Lys Tyr Lys Gly Arg Leu Ile Gln Gln Tyr Ala Val Gly Arg
        355                 360                 365

Thr Thr Gly Ser Asn Ala Ala Val Ser Val Tyr Ser Asp Asp His Gly
    370                 375                 380

Lys Thr Trp Gln Ala Gly Asn Pro Val Thr Gly Met Leu Met Asp Glu
385                 390                 395                 400

Asn Lys Val Val Glu Leu Ser Asp Gly His Val Met Leu Asn Ser Arg
                405                 410                 415

Pro Gly Asn Gly Ser Gly Tyr Arg Arg Val Ala Ile Ser Glu Asp Gly
            420                 425                 430

Gly Val Asn Tyr Gly Thr Val Lys Asn Glu Thr Gln Leu Pro Asp Pro
        435                 440                 445

Asn Asn Asn Ala His Ile Thr Arg Ala Phe Pro Asn Ala Pro Glu Gly
    450                 455                 460

Ser Ala Lys Ala Lys Val Leu Leu Tyr Ser Ser Pro Arg Ala Asn Asn
465                 470                 475                 480

Glu Gly Arg Ala Asn Gly Val Val Arg Ile Ser Leu Asp Asp Gly Thr
                485                 490                 495

Thr Trp Ser Ser Gly Lys Leu Tyr Lys Ala Gly Ser Met Ala Tyr Ser
            500                 505                 510

Val Ile Thr Ala Leu Ser Gly Ala Ala Gly Gly Gly Tyr Gly Leu Leu
        515                 520                 525

Tyr Glu Gly Ala Trp Val Thr Gly Gly Gly Ile Asp Ser His Asp Ile
    530                 535                 540

Met Tyr Thr His Ile Ser Met Asp Trp Leu Gly Tyr Leu Ser Ala Thr
545                 550                 555                 560

Ala Asp Asp Val Thr Ala Ser Val Glu Glu Gly Ala Ser Thr Val Asp
                565                 570                 575

Val Thr Val Pro Val Ser Asn Val Gly Ser Val Asp Tyr Thr Gly Val
            580                 585                 590

Thr Val Thr Pro Ala Asp Leu Pro Thr Gly Trp Ser Ala Ser Pro Val
        595                 600                 605

Asn Val Gly Ala Leu Ala Ser Gly Ala Ser Lys Asp Val Thr Val Thr
    610                 615                 620

Val Asn Val Pro Ala Thr Ala Lys Lys Asp Asp Val Ala Lys Ile Val
625                 630                 635                 640

Leu Arg Val Thr Gly Thr Ser Ala Ala Asn Ala Asp Ala Thr Thr Gly
                645                 650                 655

Phe Asp Gly Ser Ile Thr Val Asn Val Thr Glu Lys Ser Glu Pro Asp
            660                 665                 670

Pro Glu Pro Glu Pro Thr Ile Thr Gly Val Ser Ala Val Thr Ser Gln
        675                 680                 685

Ala Gly Val Lys Val Gly Asp Val Phe Asp Ala Ser Lys Val Ser Val
    690                 695                 700

Thr Ala Ala Met Ser Asp Gly Ser Ser Lys Ala Leu Ala Ala Gly Glu
705                 710                 715                 720
```

```
Tyr Ser Leu Ser Ala Val Asp Ala Asp Gly Lys Ala Val Asp Leu Ala
                725                 730                 735

Glu Pro Phe Ala Ala Ala Gly Val Val Thr Val Thr Val Ser Val Pro
            740                 745                 750

Val Glu Gly Ala Asp Pro Leu Thr Ala Ser Phe Thr Ile Asp Val Ala
        755                 760                 765

Glu Lys Ser Ala Asp Pro Glu Pro Lys Pro Glu Pro Glu Pro Lys Pro
    770                 775                 780

Glu Pro Glu Lys Pro Ala Gly Pro Lys Val Asp Val Pro Thr Glu Lys
785                 790                 795                 800

Pro Gly Leu Ser Lys Thr Gly Ala Ser Thr Ala Gly Met Ser Ile Val
                805                 810                 815

Phe Val Leu Leu Ala Leu Ser Gly Val Ala Ala Leu Ser Leu Arg Arg
            820                 825                 830

Arg Ser Val His
        835


<210> SEQ ID NO 4
<211> LENGTH: 1795
<212> TYPE: PRT
<213> ORGANISM: Bifidobacterium bifidum
<220> FEATURE:
<221> NAME/KEY: source
<222> LOCATION: 1..1795
<223> OTHER INFORMATION: /mol_type="protein"
      /organism="Bifidobacterium bifidum"

<400> SEQUENCE: 4

Met Thr Thr Ile Phe Arg Arg Ala Thr Ala Lys Thr Leu Met Arg Lys
1               5                   10                  15

Leu Ser Gly Leu Leu Val Ala Ile Ala Met Leu Ala Val Leu Pro Ala
            20                  25                  30

Gly Thr Ile Ser Ala Asn Ala Ala Asp Glu Pro Pro Gln Glu Tyr Leu
        35                  40                  45

Gln Leu Thr Leu Thr Arg Thr Asp Ser Asn Gly Thr Pro Ala Glu Val
    50                  55                  60

Gly Asp Lys Leu Thr Tyr Ser Leu Gly Tyr Lys Asn Val Ser Asp Thr
65                  70                  75                  80

Gly Phe Ile Val His Pro Thr Ala Ser Asn Leu Asn Asn Val Ala Thr
                85                  90                  95

Pro Gln Ser Ala Ser Asn Pro Asn Pro Met Cys Arg Trp Gly Asn Leu
            100                 105                 110

Ala Ala Gly Ala Ser Ala Ala Cys Thr Trp Ser Ala Ser Lys Glu Phe
        115                 120                 125

Ala Tyr His Val Val Thr Glu Asp Asp Val Ala Asn Gly Phe Thr Pro
    130                 135                 140

Thr Ala Thr Val Ser Ala Thr Thr Gln Asp Gly Thr Asn Gly Val Leu
145                 150                 155                 160

Gln Ser Val Asp Ile Thr Gly Glu Thr Val Pro Ala Val Pro Ala Thr
                165                 170                 175

Ser Thr Leu Arg Val Ala Met Gln Arg Thr Asp Thr Leu Gly Asp Asn
            180                 185                 190

Val Lys Ile Gly Asp Arg Leu Thr Phe Asn Phe Thr Tyr Thr Asn Lys
        195                 200                 205

Thr Ala Gln Lys Ile Tyr Ala Tyr Pro Ser Glu Ser Asn Ile Glu Arg
    210                 215                 220
```

```
Val Asp Val Val Ser Phe Pro Arg Asn Ser Cys Arg Ser Gly Val Glu
225                 230                 235                 240

Ala Asn Gln Thr Ala Ser Cys Gly Phe Ala Tyr His Val Ile Thr Ala
                245                 250                 255

Glu Asp Val Val Ala Arg Arg Tyr Thr Pro Thr Ala Thr Phe Arg Ala
            260                 265                 270

Thr Ser Asp Arg Asp Gly Thr Gln Val Leu Gln Asp Asp Met Thr Phe
        275                 280                 285

Thr Thr Gly Thr Val Thr Val Ala Gly Pro Ala Asp Asp Ala Ala Ser
    290                 295                 300

Thr Pro Thr Glu Arg Lys Asp Gly Glu Pro Leu Leu Leu Ala Thr Asn
305                 310                 315                 320

Lys Gln Ile Gly Asn Thr Asp Tyr Tyr Arg Ile Pro Ala Ile Ala Gln
                325                 330                 335

Ala Pro Asn Gly Trp Ile Leu Ala Ala Trp Asp Leu Arg Pro Lys Leu
            340                 345                 350

Ala Ala Asp Ala Pro Asn Pro Asn Ser Ile Val Gln Arg Ile Ser Lys
        355                 360                 365

Asp Gly Gly Lys Ser Trp Glu Thr Leu Ala Tyr Val Ala Gln Gly Arg
    370                 375                 380

Ser Ala Thr Asn Lys Tyr Gly Tyr Ser Asp Pro Ser Tyr Val Val Asp
385                 390                 395                 400

Glu Glu Ala Gly Lys Ile Phe Leu Phe Cys Val Lys Ser Tyr Asp Gln
                405                 410                 415

Gly Tyr Phe Gly Ser Val Leu Gly Val Glu Asp Ala Arg Asn Val Leu
            420                 425                 430

Gln Ala Val Val Met Glu Ser Asp Asp Asn Gly Ala Thr Trp Ser Glu
        435                 440                 445

Pro Arg Asn Ile Thr Lys Asp Ile Thr Lys Gly His Glu Asp Glu Trp
    450                 455                 460

Lys Ser Arg Phe Ala Ser Ser Gly His Gly Ile Gln Leu Lys Tyr Gly
465                 470                 475                 480

Gln Tyr Lys Gly Arg Leu Ile Gln Gln Tyr Ala Val Arg Thr Thr Ser
                485                 490                 495

Asn Thr Asn Ile Ala Val Ser Val Tyr Ser Asp Asp His Gly Lys Thr
            500                 505                 510

Trp Lys Ala Gly Asn Pro Val Thr Glu Val Asn Met Asp Glu Asn Lys
        515                 520                 525

Val Val Glu Leu Ser Asp Gly Arg Val Met Leu Asn Ser Arg Pro Gly
    530                 535                 540

Ala Ala Gly Tyr Arg Arg Val Ala Ile Ser Glu Asp Gly Gly Val Asn
545                 550                 555                 560

Tyr Gly Pro Ile Lys Ser Glu Thr Gln Leu Pro Asp Pro Asn Asn Asn
                565                 570                 575

Ala Gln Ile Thr Arg Ala Phe Pro Asn Ala Pro Glu Gly Ser Ala Lys
            580                 585                 590

Ala Lys Val Leu Leu Tyr Ser Ala Pro Arg Ala Ser Asn Glu Gly Arg
        595                 600                 605

Ala Asn Gly Val Val Arg Val Ser Phe Asp Asp Gly Thr Thr Trp Ser
    610                 615                 620

Ala Gly Lys Leu Phe Lys Ala Gly Ser Met Ala Tyr Ser Val Ile Thr
625                 630                 635                 640

Ala Leu Asn Asp Ala Ala Gly Gly Gly Tyr Gly Leu Leu Tyr Glu Gly
```

-continued

```
                645                 650                 655

Glu Ser Ile Thr Tyr Thr Arg Ala Ser Met Glu Trp Leu Gly Tyr Leu
            660                 665                 670

Thr Ala Thr Ala Ser Gly Thr Ala Ala Val Lys Glu Gly Glu Gly Thr
        675                 680                 685

Leu Thr Ala Pro Val Thr Val Thr Asn Asp Gly Leu Thr Asp Tyr Thr
    690                 695                 700

Asn Val Thr Val Thr Pro Thr Gly Leu Pro Ser Gly Trp Ser Ala Glu
705                 710                 715                 720

Ala Val Asn Val Gly Asn Leu Ala Ala Gly Gln Ser Ala Thr Val Asn
                725                 730                 735

Val Pro Val Thr Val Pro Ala Ala Ala Val Ser Gly Thr Val Ala Lys
            740                 745                 750

Ala Thr Met Lys Ile Thr Gly Lys Tyr Ala Gln Ser Glu Asp Thr Leu
        755                 760                 765

His Ser Phe Ala Glu Gly Glu Leu Ala Val Thr Val Thr Asp Pro Asp
    770                 775                 780

Pro Ala Ala Lys Arg Leu Lys Leu Thr Ile Glu Arg Thr Asp Asp Asn
785                 790                 795                 800

Gly Asp Pro Val Lys Val Gly Asp Thr Leu Thr Tyr Arg Ile Thr Tyr
                805                 810                 815

Glu Asn Val Gly Thr Gln Ser Phe Ala Val Tyr Pro Arg Glu Ser Asn
            820                 825                 830

Leu Asp Gly Val Thr Thr Pro Gln Ser Ala Ser Asn Pro Ala Pro Val
        835                 840                 845

Cys Arg Trp Ser Arg Leu Ala Pro Gly Ala Thr Gly Ala Cys Val Ser
    850                 855                 860

Gly Asn Gly Lys Gln Leu Ala Tyr His Thr Val Thr Glu Ala Asp Ala
865                 870                 875                 880

Thr Ala Gly Ser Phe Thr Pro Ser Ala Thr Ile Asp Ala Thr Ala Asp
                885                 890                 895

Ala Ser Gly Glu Thr Val Leu Glu Ser Val Ser Ile Thr Gly Asp Pro
            900                 905                 910

Val Thr Val Ser Gln Pro Val Glu Leu Pro Ala Asp Ile Ala Ala Trp
        915                 920                 925

Lys Thr Arg Asn Glu Ala Leu Ala Asp Trp Gln Thr Leu Ser Glu Lys
    930                 935                 940

Leu Ala Lys Thr Asp Arg Ile Asn Trp Leu Phe Thr Gly Asp Ser Ile
945                 950                 955                 960

Thr His Gly Val Gln Phe Thr Arg Gly Tyr Arg Thr Tyr Ser Glu Leu
                965                 970                 975

Phe Ala Asn His Leu Asp Thr Ala Ser Val Arg Gly Val Ser Arg Ala
            980                 985                 990

Asn Asp Val Val Met Asn Thr Gly Ile Ser Ser Ala Asp Ala Ser Trp
        995                 1000                1005

Pro Leu Lys Asp Gly Ala Phe Glu Lys Trp Val Ser Asp Lys His Pro
    1010                1015                1020

Asp Val Val Phe Leu Thr Phe Gly Met Asn Asp Gly Arg Thr Gly Gln
1025                1030                1035                1040

Ala Phe Thr Val Asp Gln Tyr Thr Ala Asn Leu Ser Thr Leu Ile Asp
                1045                1050                1055

Lys Ile Arg Asp Leu Gly Ala Ile Pro Val Leu Gln Thr Gln Asn Tyr
            1060                1065                1070
```

```
Thr Thr Asn Thr Thr Phe Asn Ala Asn Leu Asp Thr Tyr Phe Asp Ala
        1075                1080                1085

Glu Arg Arg Leu Ala Leu Asp Lys Asn Val Leu Leu Val Asp Phe Asn
    1090                1095                1100

Lys Gln Trp Leu Glu Leu Gly Gly Gly Asn Arg Glu Ser Gly Thr Tyr
1105                1110                1115                1120

Met Gly Ala Gly Asn Asp Ile His Pro Gly Glu Asn Gly His Ile Glu
                1125                1130                1135

Trp Ala Lys Phe Thr Leu Gly Ala Leu Asn Met Ile Ala Asn Asp Asp
            1140                1145                1150

Pro Leu Ala Arg Trp Ser Ser Ser Asp Thr Thr Leu Asp Lys Pro Thr
        1155                1160                1165

Val Thr Val Asp Ala Asp Gly Asn Gly Leu Lys Gly Ser Asp Gly Leu
    1170                1175                1180

Glu Pro Ala Pro Ala Ala Ala Lys Ser Val Gly Lys Phe Leu Ser Gly
1185                1190                1195                1200

Ala Gln Tyr Val Asp Leu Gly Gly Asp Val Val Ser Ala Val Ala Gly
                1205                1210                1215

Lys Arg Glu Ser Asn Val Thr Ile Arg Phe Arg Ala Ser Ala Thr Gly
            1220                1225                1230

Gln Pro Gln Thr Leu Phe Ser Leu Gly Asp Ser Asp Ser Ala Thr Arg
        1235                1240                1245

Ala Thr Val Arg Leu Ser Ala Thr Gly Leu Val Gln Phe Leu Asn Ser
    1250                1255                1260

Gly Asn Thr Gly Asp Phe Tyr Thr Val Gly Thr Asn Asp Leu Ala Asp
1265                1270                1275                1280

Gly Ala Trp His Thr Val Ser Val Asn Phe Val Ala Asn Gly Phe Thr
                1285                1290                1295

Ile Tyr Val Asp Gly Ala Ala Met Arg Ala Ile Ser Gly Gly Ala Gly
            1300                1305                1310

Thr Gln Leu Asn Val Pro Gly Ala Ile Thr Val Asn Thr Ala Thr Ala
        1315                1320                1325

Gly Ala Ile Arg Gly Ala Asp Ser Ala Gly Gly Ala Gln Gln Leu Thr
    1330                1335                1340

Gly Ile Val Asp Tyr Val Ala Ala Trp Ser Arg Thr Leu Thr Asp Ala
1345                1350                1355                1360

Glu Ala Lys Arg Ile Ser Ala Glu Thr Ser Ala Val Ala Val Thr Lys
                1365                1370                1375

Val Asp Ala Ala Val Asn Ala Leu Gln Pro Ile Ile Ser Asp Thr Gly
            1380                1385                1390

Ala Arg Lys Asn Ile Val Phe Val Gly Gly Glu Thr Ile Glu Gly Gly
        1395                1400                1405

Tyr Thr Asp His Leu Ile Ala Lys Asn Ile Val Gln Leu Leu Asp Glu
    1410                1415                1420

Arg Val Arg Trp Glu Tyr Val Thr Gly Leu Ser Ala Thr Asp Arg Glu
1425                1430                1435                1440

Arg Gln Arg Ala Lys Phe Phe Val Ala Ala Gly Gln Gly Gly Leu Thr
                1445                1450                1455

Ala Lys Gln Met Asp Glu Asp Tyr Ala Ala Met Val Gly Glu Tyr Ser
            1460                1465                1470

Pro Asp Ile Leu Phe Leu Ala Pro Asp Leu Tyr Asp Ala Asp Gly Asn
        1475                1480                1485
```

```
Leu Ala Glu Ser Ala Ala Ala Ala Phe Ala Gly His Ile Arg Ser Val
    1490                1495                1500

Ala Ala Lys Ala Lys Glu Ala Gly Ala Lys Val Val Leu Val Thr Pro
1505                1510                1515                1520

Val Thr Val Arg Gly Gly Glu Asp Glu Tyr Ala Gly Ala Met Arg Thr
                1525                1530                1535

Val Ala Lys Glu Asp Asp Leu Pro Leu Ile Asp Ala Gln Ala Trp Ile
            1540                1545                1550

Gly Lys Val Val Ala Ala Asp Ala Ser Val Lys Thr Ala Trp Phe Asn
        1555                1560                1565

Lys Ala Gly Gln Leu Asn Tyr Ala Gly His Leu Gly Tyr Ala Arg Phe
    1570                1575                1580

Met Met Arg Ser Leu Asp Leu Tyr Pro Ser Asn Val Ser Gly Ser Arg
1585                1590                1595                1600

Ile Ala Ser Leu Pro Tyr Asp Thr Ala Asn Val Thr Leu Val Gly Ala
                1605                1610                1615

Ser Glu Asn Gly Gly Glu Leu Pro Val Gly Arg Val Glu Gly Thr Asp
            1620                1625                1630

Arg Ala His Ile Asp Thr Met Gln Ile Gly Ala Ala Ala Ser Leu Val
        1635                1640                1645

Val Val Asp Ser Tyr Ala Val Tyr Glu Ile Gly Glu Asp Gly Gly Arg
    1650                1655                1660

Thr Leu Val Ala Asp Gly Leu Lys Pro Ala Asp Val Leu Ala Asp Gly
1665                1670                1675                1680

Ile Asp Val Thr Val Asn Asp Thr Ala Ala His Arg Tyr Glu Val Val
                1685                1690                1695

Gly Ser Ala Asn Val Pro Glu Gly Ala Asp Ala Val Thr Val Thr Tyr
            1700                1705                1710

Thr Ala Thr Leu Ala Ala Val Glu Glu Pro Glu Pro Gly Pro Asp Pro
        1715                1720                1725

Asp Pro Thr Pro Asp Pro Ser Glu Lys Pro Asp Gly Asp Gly Thr Gly
    1730                1735                1740

Asp Gly Thr Gly Ala Gly Thr Gly Asp Val Gln Lys Pro Thr Pro Asp
1745                1750                1755                1760

Ala Val Ala Lys Thr Gly Ala Asp Val Phe Gly Leu Leu Thr Ala Val
                1765                1770                1775

Ala Ala Leu Leu Ala Ala Gly Gly Val Thr Leu Ser Leu Arg Arg Arg
            1780                1785                1790

Ala Asn Arg
        1795


<210> SEQ ID NO 5
<211> LENGTH: 1795
<212> TYPE: PRT
<213> ORGANISM: Bifidobacterium bifidum
<220> FEATURE:
<221> NAME/KEY: source
<222> LOCATION: 1..1795
<223> OTHER INFORMATION: /mol_type="protein"
      /organism="Bifidobacterium bifidum"

<400> SEQUENCE: 5

Met Thr Thr Ile Phe Arg Arg Ala Thr Ala Lys Thr Leu Met Arg Lys
1               5                   10                  15

Leu Ser Gly Leu Leu Val Ala Ile Ala Met Leu Ala Val Leu Pro Ala
            20                  25                  30
```

-continued

```
Gly Thr Ile Ser Ala Asn Ala Ala Asp Glu Pro Pro Gln Glu Tyr Leu
            35                  40                  45

Gln Leu Thr Leu Thr Arg Thr Asp Ser Asn Gly Thr Pro Ala Glu Val
    50                  55                  60

Gly Asp Lys Leu Thr Tyr Ser Leu Gly Tyr Lys Asn Val Ser Asp Thr
65                  70                  75                  80

Gly Phe Ile Val His Pro Thr Ala Ser Asn Leu Asn Asn Val Ala Thr
                85                  90                  95

Pro Gln Ser Ala Ser Asn Pro Asn Pro Met Cys Arg Trp Gly Asn Leu
            100                 105                 110

Ala Ala Gly Ala Ser Ala Ala Cys Thr Trp Ser Ala Ser Lys Glu Phe
        115                 120                 125

Ala Tyr His Val Val Thr Glu Asp Asp Val Ala Asn Gly Phe Thr Pro
    130                 135                 140

Thr Ala Thr Val Ser Ala Thr Thr Gln Asp Gly Thr Asn Gly Val Leu
145                 150                 155                 160

Gln Ser Val Asp Ile Thr Gly Glu Thr Val Pro Ala Val Pro Ala Thr
                165                 170                 175

Ser Thr Leu Arg Val Ala Met Gln Arg Thr Asp Thr Leu Gly Asp Asn
            180                 185                 190

Val Lys Ile Gly Asp Arg Leu Thr Phe Asn Phe Thr Tyr Thr Asn Lys
        195                 200                 205

Thr Ala Gln Lys Ile Tyr Ala Tyr Pro Ser Glu Ser Asn Ile Glu Arg
    210                 215                 220

Val Asp Val Val Ser Phe Pro Arg Asn Ser Cys Arg Ser Gly Val Glu
225                 230                 235                 240

Ala Asn Gln Thr Ala Ser Cys Gly Phe Ala Tyr His Val Ile Thr Ala
                245                 250                 255

Glu Asp Val Val Ala Arg Arg Tyr Thr Pro Thr Ala Thr Phe Arg Ala
            260                 265                 270

Thr Ser Asp Arg Asp Gly Thr Gln Val Leu Gln Asp Asp Met Thr Phe
        275                 280                 285

Thr Thr Gly Thr Val Thr Val Ala Gly Pro Ala Asp Asp Ala Ala Ser
    290                 295                 300

Thr Pro Thr Glu Arg Lys Asp Gly Glu Pro Leu Leu Leu Ala Thr Asn
305                 310                 315                 320

Lys Gln Ile Gly Asn Thr Asp Tyr Tyr Arg Ile Pro Ala Ile Ala Gln
                325                 330                 335

Ala Pro Asn Gly Trp Ile Leu Ala Ala Trp Asp Leu Arg Pro Lys Leu
            340                 345                 350

Ala Ala Asp Ala Pro Asn Pro Asn Ser Ile Val Gln Arg Ile Ser Lys
        355                 360                 365

Asp Gly Gly Lys Ser Trp Glu Thr Leu Ala Tyr Val Ala Gln Gly Arg
    370                 375                 380

Ser Ala Thr Asn Lys Tyr Gly Tyr Ser Asp Pro Ser Tyr Val Val Asp
385                 390                 395                 400

Glu Glu Ala Gly Lys Ile Phe Leu Phe Cys Val Lys Ser Tyr Asp Gln
                405                 410                 415

Gly Tyr Phe Gly Ser Val Leu Gly Val Glu Asp Ala Arg Asn Val Leu
            420                 425                 430

Gln Ala Val Val Met Glu Ser Asp Asp Asn Gly Ala Thr Trp Ser Glu
        435                 440                 445

Pro Arg Asn Ile Thr Lys Asp Ile Thr Lys Gly His Glu Asp Glu Trp
```

```
    450                 455                 460

Lys Ser Arg Phe Ala Ser Ser Gly His Gly Ile Gln Leu Lys Tyr Gly
465                 470                 475                 480

Gln Tyr Lys Gly Arg Leu Ile Gln Gln Tyr Ala Val Arg Thr Thr Ser
                485                 490                 495

Asn Thr Asn Ile Ala Val Ser Val Tyr Ser Asp Asp His Gly Lys Thr
            500                 505                 510

Trp Lys Ala Gly Asn Pro Val Thr Glu Ala Asn Met Asp Glu Asn Lys
        515                 520                 525

Val Val Glu Leu Ser Asp Gly Arg Val Met Leu Asn Ser Arg Pro Gly
    530                 535                 540

Ala Ala Gly Tyr Arg Arg Val Ala Ile Ser Glu Asp Gly Gly Val Asn
545                 550                 555                 560

Tyr Gly Pro Ile Lys Ser Glu Thr Gln Leu Pro Asp Pro Asn Asn Asn
                565                 570                 575

Ala Gln Ile Thr Arg Ala Phe Pro Asn Ala Pro Glu Gly Ser Ala Lys
            580                 585                 590

Ala Lys Val Leu Leu Tyr Ser Ala Pro Arg Ala Ser Asn Glu Gly Arg
        595                 600                 605

Ala Asn Gly Val Val Arg Val Ser Phe Asp Asp Gly Thr Thr Trp Ser
    610                 615                 620

Ala Gly Lys Leu Phe Lys Glu Gly Ser Met Ala Tyr Ser Val Ile Thr
625                 630                 635                 640

Ala Leu Asn Asp Ala Ala Gly Gly Gly Tyr Gly Leu Leu Tyr Glu Gly
                645                 650                 655

Glu Ser Ile Thr Tyr Thr Arg Val Ser Met Glu Trp Leu Gly Tyr Leu
            660                 665                 670

Thr Ala Thr Ala Ser Gly Thr Ala Thr Val Lys Glu Gly Glu Gly Thr
        675                 680                 685

Leu Thr Ala Pro Val Thr Val Thr Asn Asp Gly Leu Thr Asp Tyr Thr
    690                 695                 700

Asn Val Thr Val Thr Pro Thr Gly Leu Pro Ser Gly Trp Ser Ala Glu
705                 710                 715                 720

Ala Val Asn Val Gly Asn Leu Ala Ala Gly Gln Ser Ala Thr Val Asn
                725                 730                 735

Val Pro Val Thr Val Pro Ala Ala Ala Val Ser Gly Thr Val Ala Lys
            740                 745                 750

Ala Thr Met Lys Ile Thr Gly Lys Tyr Ala Gln Ser Glu Asp Thr Leu
        755                 760                 765

His Ser Phe Ala Glu Gly Glu Leu Ala Val Thr Val Thr Glu Pro Asp
    770                 775                 780

Pro Ala Ala Lys Arg Leu Lys Leu Thr Ile Glu Arg Thr Asp Asp Asn
785                 790                 795                 800

Gly Ala Pro Val Lys Val Gly Asp Thr Leu Thr Tyr Arg Ile Thr Tyr
                805                 810                 815

Glu Asn Val Gly Thr Gln Ser Phe Ala Val Tyr Pro Arg Lys Ser Asn
            820                 825                 830

Leu Asp Gly Val Thr Thr Pro Gln Ser Ala Ser Asn Pro Ala Pro Val
        835                 840                 845

Cys Arg Trp Ser Arg Leu Asp Pro Gly Thr Thr Gly Ala Cys Val Ser
    850                 855                 860

Gly Asn Gly Lys Arg Leu Ala Tyr His Thr Val Thr Glu Ala Asp Ala
865                 870                 875                 880
```

```
Thr Ala Gly Ser Phe Thr Pro Ser Ala Thr Ile Asp Ala Thr Ala Asp
        885                 890                 895

Thr Ser Gly Glu Thr Val Leu Glu Ser Val Ser Ile Thr Gly Asp Pro
    900                 905                 910

Val Thr Val Ser Gln Pro Val Glu Leu Pro Ala Asp Ile Ala Ala Trp
915                 920                 925

Lys Thr Arg Asn Glu Ala Leu Asp Asp Trp Gln Thr Leu Ser Glu Lys
                930                 935                 940

Leu Ala Lys Thr Asp Arg Ile Asn Trp Leu Phe Thr Gly Asp Ser Ile
945         950                 955                 960

Thr His Gly Val Gln Leu Thr Arg Gly Tyr Arg Thr Tyr Ser Glu Leu
        965                 970                 975

Phe Ala Asn His Leu Asp Thr Ala Ser Val Arg Gly Val Ser Arg Ala
    980                 985                 990

Asn Asp Val Val Met Asn Thr Gly Ile Ser Ser Ala Asp Ala Ser Trp
995                 1000                1005

Pro Leu Lys Asp Gly Ala Phe Glu Lys Trp Val Ser Asp Lys His Pro
                1010                1015                1020

Asp Val Val Phe Leu Thr Phe Gly Met Asn Asp Gly Arg Thr Gly Gln
1025        1030                1035                1040

Ala Phe Thr Val Asp Gln Tyr Thr Ala Asn Leu Ser Thr Leu Ile Asp
        1045                1050                1055

Lys Ile Arg Asp Leu Gly Ala Ile Pro Val Leu Gln Thr Gln Asn Tyr
    1060                1065                1070

Thr Thr Asn Thr Thr Phe Asn Ala Asn Leu Asp Thr Tyr Phe Asp Ala
                    1075                1080                1085

Glu Arg Arg Leu Ala Leu Asp Lys Asn Val Leu Leu Val Asp Phe Asn
                1090                1095                1100

Lys Gln Trp Leu Glu Leu Gly Gly Gly Asn Arg Glu Ser Gly Thr Tyr
1105                1110                1115                1120

Met Gly Ala Gly Asn Asp Ile His Pro Gly Glu Asn Gly His Ile Glu
                1125                1130                1135

Trp Ala Lys Phe Thr Leu Gly Ala Leu Asn Met Ile Ala Asn Asp Asp
            1140                1145                1150

Pro Leu Ala Arg Trp Ser Ser Ser Asp Thr Thr Leu Asp Lys Pro Thr
        1155                1160                1165

Val Thr Val Asp Ala Asp Gly Asn Gly Leu Lys Gly Ser Asp Gly Leu
    1170                1175                1180

Glu Pro Ala Pro Ala Ala Ala Lys Ser Val Gly Lys Phe Leu Ser Gly
1185                1190                1195                1200

Ala Gln Tyr Val Asp Leu Gly Gly Asp Val Val Ser Ala Val Ala Gly
                1205                1210                1215

Lys Arg Glu Ser Asn Val Thr Ile Arg Phe Arg Ala Ser Ala Thr Gly
            1220                1225                1230

Gln Pro Gln Thr Leu Phe Ser Leu Gly Asp Ser Asp Ser Ala Thr Arg
        1235                1240                1245

Ala Thr Val Arg Leu Ser Ala Thr Gly Leu Val Gln Phe Leu Asn Ser
    1250                1255                1260

Gly Asn Thr Gly Asp Phe Tyr Thr Val Gly Thr Asn Asp Leu Ala Asp
1265                1270                1275                1280

Gly Ala Trp His Thr Val Ser Val Asn Phe Val Ala Asn Gly Phe Thr
                1285                1290                1295
```

-continued

```
Ile Tyr Val Asp Gly Ala Ala Met Arg Ala Ile Ser Gly Gly Ala Gly
            1300                1305                1310

Thr Gln Leu Asn Val Pro Gly Ala Ile Thr Val Asn Thr Ala Thr Ala
        1315                1320                1325

Gly Ala Ile Arg Gly Ala Asp Ser Ala Gly Gly Ala Gln Gln Leu Thr
    1330                1335                1340

Gly Ile Val Asp Tyr Val Ala Ala Trp Ser Arg Thr Leu Thr Asp Ala
1345                1350                1355                1360

Glu Ala Lys Arg Ile Ser Ala Glu Thr Ser Ala Val Ala Val Thr Lys
                1365                1370                1375

Val Asp Ala Ala Val Asn Ala Leu Gln Pro Ile Ile Ser Asp Thr Gly
            1380                1385                1390

Ala Arg Lys Asn Ile Val Phe Val Gly Gly Glu Thr Ile Glu Gly Gly
        1395                1400                1405

Tyr Thr Asp His Leu Ile Ala Lys Asn Ile Val Gln Leu Leu Asp Glu
    1410                1415                1420

Arg Val Arg Trp Glu Tyr Val Thr Gly Leu Ser Ala Thr Asp Arg Glu
1425                1430                1435                1440

Leu Gln Arg Ala Lys Phe Phe Val Ala Ala Gly Gln Gly Gly Leu Thr
                1445                1450                1455

Ala Lys Gln Met Asp Glu Asp Tyr Ala Ala Met Val Gly Glu Tyr Ser
            1460                1465                1470

Pro Asp Ile Leu Phe Leu Ala Pro Asp Leu Tyr Asp Ala Asp Gly Ile
        1475                1480                1485

Leu Ala Glu Ser Asp Ala Ala Ala Phe Ala Gly His Ile Arg Ser Val
    1490                1495                1500

Ala Ala Lys Ala Lys Glu Ala Gly Ala Lys Val Val Leu Val Thr Pro
1505                1510                1515                1520

Val Thr Val Arg Gly Gly Glu Asp Glu Tyr Ala Gly Ala Met Arg Thr
                1525                1530                1535

Val Ala Lys Glu Asp Asp Leu Pro Leu Ile Asp Ala Gln Ala Trp Ile
            1540                1545                1550

Gly Lys Val Val Ala Ala Asp Ala Ser Val Lys Thr Ala Trp Phe Asn
        1555                1560                1565

Lys Ala Gly Gln Leu Asn Tyr Ala Gly His Leu Gly Tyr Ala Arg Phe
    1570                1575                1580

Met Met Arg Ser Leu Asp Leu Tyr Pro Ser Asn Val Ser Gly Ser Arg
1585                1590                1595                1600

Ile Ala Ser Leu Pro Tyr Asp Thr Ala Asn Val Thr Leu Val Gly Ala
                1605                1610                1615

Ser Glu Asn Gly Gly Glu Leu Pro Val Gly Arg Val Glu Gly Thr Asp
            1620                1625                1630

Arg Ala His Ile Asp Thr Met Gln Ile Gly Ala Ala Ala Ser Leu Val
        1635                1640                1645

Val Thr Asp Ser Tyr Ala Val Tyr Glu Ile Gly Glu Asp Gly Gly Arg
    1650                1655                1660

Thr Leu Val Ala Asp Gly Leu Lys Pro Ala Asp Val Leu Ala Asp Gly
1665                1670                1675                1680

Ile Asp Val Thr Val Asn Asp Thr Ala Ala His Arg Tyr Glu Val Val
                1685                1690                1695

Gly Ser Ala Asn Val Pro Glu Gly Ala Asp Ala Val Thr Val Thr Tyr
            1700                1705                1710

Thr Ala Thr Leu Ala Ala Val Glu Glu Pro Glu Pro Gly Pro Asp Pro
```

```
        1715                1720                1725

Asp Pro Thr Pro Asp Pro Ser Glu Lys Pro Asp Gly Asp Gly Thr Gly
    1730                1735                1740

Asp Gly Thr Gly Ala Gly Ala Gly Asp Val Gln Lys Pro Thr Pro Asp
1745                1750                1755                1760

Ala Val Ala Lys Thr Gly Ala Asp Val Phe Gly Leu Leu Ala Ala Val
                1765                1770                1775

Ala Val Leu Leu Ala Ala Gly Gly Val Thr Leu Ser Leu Arg Arg Arg
            1780                1785                1790

Ala Asn Arg
        1795


<210> SEQ ID NO 6
<211> LENGTH: 770
<212> TYPE: PRT
<213> ORGANISM: Bifidobacterium bifidum
<220> FEATURE:
<221> NAME/KEY: source
<222> LOCATION: 1..770
<223> OTHER INFORMATION: /mol_type="protein"
      /organism="Bifidobacterium bifidum"

<400> SEQUENCE: 6

Met Val Arg Ser Thr Lys Pro Ser Leu Leu Arg Arg Phe Gly Ala Leu
1               5                   10                  15

Val Ala Ala Ala Ala Met Leu Val Val Leu Pro Ala Gly Val Ser Thr
            20                  25                  30

Ala Ser Ala Ala Ser Asp Asp Ala Asp Met Leu Thr Val Thr Met Thr
        35                  40                  45

Arg Thr Asp Ala Leu Gly Asp Glu Val Tyr Val Gly Asp Thr Leu Thr
    50                  55                  60

Tyr Ser Phe Thr Asn Thr Asn Asn Thr Ser Ser Ala Phe Thr Ala Phe
65                  70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
            100                 105                 110

Ala Ser His Thr Ile Thr Ala Asp Asp Leu Thr Ala Gly Ser Phe Thr
        115                 120                 125

Pro Arg Thr Val Trp Lys Ala Thr Ser Asp Arg Gly Gly Thr Gln Val
    130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
            180                 185                 190

Tyr Arg Ile Pro Ala Leu Ala Glu Ala Pro Asn Gly Trp Ile Leu Ala
        195                 200                 205

Ala Phe Asp Gln Arg Pro Asn Thr Ala Met Ala Asn Gly Ser Gly Val
    210                 215                 220

Lys Cys Trp Asp Ala Pro Gln Pro Asn Ser Ile Val Gln Arg Ile Ser
225                 230                 235                 240

Lys Asp Gly Gly Lys Ser Trp Thr Pro Ile Gln Tyr Val Ala Gln Gly
                245                 250                 255

Lys Asn Ala Pro Glu Arg Tyr Gly Tyr Ser Asp Pro Ser Tyr Val Val
```

```
            260                 265                 270

Asp Lys Glu Thr Gly Glu Ile Phe Leu Phe Phe Val His Ser Tyr Asn
        275                 280                 285

Lys Gly Phe Ala Asp Ser Gln Leu Gly Val Asp Glu Ser Asn Arg Asn
    290                 295                 300

Val Leu His Ala Val Val Val Ser Ser Lys Asp Asn Gly Glu Thr Trp
305                 310                 315                 320

Ser Lys Pro Arg Asp Ile Thr Ala Asp Ile Thr Lys Gly Tyr Glu Asn
                325                 330                 335

Glu Trp Lys Ser Arg Phe Ala Thr Ser Gly Ala Gly Ile Gln Leu Lys
            340                 345                 350

Tyr Gly Lys Tyr Lys Gly Arg Leu Ile Gln Gln Tyr Ala Val Gly Arg
        355                 360                 365

Thr Thr Gly Ser Asn Ala Ala Val Ser Val Tyr Ser Asp Asp His Gly
    370                 375                 380

Lys Thr Trp Gln Ala Gly Asn Pro Val Thr Gly Met Leu Met Asp Glu
385                 390                 395                 400

Asn Lys Val Val Glu Leu Ser Asp Gly Arg Val Met Leu Asn Ser Arg
                405                 410                 415

Pro Gly Asn Gly Ser Gly Tyr Arg Arg Val Ala Ile Ser Glu Asp Gly
            420                 425                 430

Gly Val Asn Tyr Gly Thr Val Lys Asn Glu Thr Gln Leu Pro Asp Pro
        435                 440                 445

Asn Asn Asn Ala His Ile Thr Arg Ala Phe Pro Asn Ala Pro Glu Gly
    450                 455                 460

Ser Ala Lys Ala Lys Val Leu Leu Tyr Ser Ser Pro Arg Ala Asn Asn
465                 470                 475                 480

Glu Gly Arg Ala Asn Gly Val Val Arg Ile Ser Leu Asp Asp Gly Thr
                485                 490                 495

Thr Trp Ser Ser Gly Lys Leu Tyr Lys Glu Gly Ser Met Ala Tyr Ser
            500                 505                 510

Val Ile Thr Ala Leu Ser Gly Ala Ala Gly Gly Gly Tyr Gly Leu Leu
        515                 520                 525

Tyr Glu Gly Ala Trp Val Thr Gly Gly Gly Ile Asp Ser His Asp Ile
    530                 535                 540

Met Tyr Thr His Ile Ser Met Asp Trp Leu Gly Tyr Leu Ser Ala Thr
545                 550                 555                 560

Ala Asp Asp Val Thr Ala Ser Val Glu Glu Gly Ala Ser Thr Val Asp
                565                 570                 575

Val Thr Val Pro Val Ser Asn Val Gly Ser Val Asp Tyr Thr Gly Val
            580                 585                 590

Thr Val Thr Pro Ala Asp Leu Pro Thr Gly Trp Ser Ala Ser Pro Val
        595                 600                 605

Asn Val Gly Ala Leu Ala Ser Gly Ala Ser Lys Asp Val Thr Val Thr
    610                 615                 620

Val Asn Val Pro Ala Thr Ala Lys Lys Asp Asp Val Ala Lys Ile Val
625                 630                 635                 640

Leu Arg Val Thr Gly Thr Ser Ala Ala Asn Ala Asn Ala Thr Thr Gly
                645                 650                 655

Phe Asp Gly Ser Ile Thr Val Asn Val Thr Glu Lys Ser Glu Pro Asp
            660                 665                 670

Pro Glu Pro Glu Pro Thr Ile Thr Gly Val Ser Ala Val Thr Ser Gln
        675                 680                 685
```

```
Ala Gly Val Lys Val Gly Asp Val Phe Asp Ala Ser Lys Val Ser Val
    690                 695                 700

Thr Ala Ala Met Ser Asp Gly Ser Ser Lys Ala Leu Ala Ala Gly Glu
705                 710                 715                 720

Tyr Ser Leu Ser Ala Val Asp Ala Asp Gly Lys Ala Val Asp Leu Ala
                725                 730                 735

Glu Pro Phe Ala Ala Ala Gly Val Val Thr Val Thr Val Ser Val Pro
            740                 745                 750

Val Glu Gly Ala Asp Pro Leu Thr Ala Ser Phe Thr Ile Asp Val Ala
        755                 760                 765

Glu Lys
    770


<210> SEQ ID NO 7
<211> LENGTH: 834
<212> TYPE: PRT
<213> ORGANISM: Bifidobacterium bifidum
<220> FEATURE:
<221> NAME/KEY: source
<222> LOCATION: 1..834
<223> OTHER INFORMATION: /mol_type="protein"
      /organism="Bifidobacterium bifidum"

<400> SEQUENCE: 7

Met Val Arg Ser Thr Lys Pro Ser Leu Leu Arg Arg Leu Gly Ala Leu
1               5                   10                  15

Val Ala Ala Ala Ala Met Leu Val Val Leu Pro Ala Gly Val Ser Thr
            20                  25                  30

Ala Ser Ala Ala Ser Asp Asp Ala Asp Met Leu Thr Val Thr Met Thr
        35                  40                  45

Arg Thr Asp Ala Leu Gly Asp Glu Val Tyr Val Gly Asp Thr Leu Thr
    50                  55                  60

Tyr Ser Phe Thr Asn Thr Asn Asn Thr Ser Ser Ala Phe Thr Ala Phe
65                  70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
            100                 105                 110

Ala Ser His Thr Ile Thr Ala Asp Asp Leu Thr Ala Gly Ser Phe Thr
        115                 120                 125

Pro Arg Thr Val Trp Lys Ala Thr Ser Asp Arg Gly Gly Thr Gln Val
    130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
            180                 185                 190

Tyr Arg Ile Pro Ala Leu Ala Glu Ala Pro Asn Gly Trp Ile Leu Ala
        195                 200                 205

Ala Phe Asp Gln Arg Pro Asn Thr Ala Met Ala Asn Gly Ser Gly Val
    210                 215                 220

Lys Cys Trp Asp Ala Pro Gln Pro Asn Ser Ile Val Gln Arg Ile Ser
225                 230                 235                 240

Lys Asp Gly Gly Lys Ser Trp Thr Pro Ile Gln Tyr Val Ala Gln Gly
                245                 250                 255
```

```
Lys Asn Ala Pro Glu Arg Tyr Gly Tyr Ser Asp Pro Ser Tyr Val Val
            260                 265                 270

Asp Glu Glu Thr Gly Glu Ile Phe Leu Phe Phe Val His Ser Tyr Asn
        275                 280                 285

Lys Gly Phe Ala Asp Ser Gln Leu Gly Val Asp Glu Ser Asn Arg Asn
    290                 295                 300

Val Leu His Ala Val Val Val Ser Ser Lys Asp Asn Gly Glu Thr Trp
305                 310                 315                 320

Ser Lys Pro Arg Asp Ile Thr Ala Asp Ile Thr Lys Gly Tyr Glu Asn
                325                 330                 335

Glu Trp Lys Ser Arg Phe Ala Thr Ser Gly Ala Gly Ile Gln Leu Lys
            340                 345                 350

Tyr Gly Lys Tyr Lys Gly Arg Leu Ile Gln Gln Tyr Ala Val Gly Arg
        355                 360                 365

Thr Thr Gly Ser Asn Ala Ala Val Ser Val Tyr Ser Asp Asp His Gly
    370                 375                 380

Lys Thr Trp Gln Ala Gly Asn Pro Val Thr Gly Met Leu Met Asp Glu
385                 390                 395                 400

Asn Lys Val Val Glu Leu Ser Asp Gly Arg Val Met Leu Asn Ser Arg
                405                 410                 415

Pro Gly Asn Gly Ser Gly Tyr Arg Arg Val Ala Ile Ser Lys Asp Gly
            420                 425                 430

Gly Val Asn Tyr Gly Thr Val Lys Asn Glu Thr Gln Leu Pro Asp Pro
        435                 440                 445

Asn Asn Asn Ala His Ile Thr Arg Ala Phe Pro Asn Ala Pro Glu Gly
    450                 455                 460

Ser Ala Lys Ala Lys Val Leu Leu Tyr Ser Ser Pro Arg Ala Asn Asn
465                 470                 475                 480

Glu Gly Arg Ala Asn Gly Val Val Arg Ile Ser Leu Asp Asp Gly Thr
                485                 490                 495

Thr Trp Ser Ser Gly Lys Leu Tyr Lys Ala Gly Ser Met Ala Tyr Ser
            500                 505                 510

Val Ile Thr Ala Leu Ser Gly Ala Ala Gly Gly Gly Tyr Gly Leu Leu
        515                 520                 525

Tyr Glu Gly Ala Trp Val Thr Gly Gly Gly Ile Asp Ser His Asp Ile
    530                 535                 540

Met Tyr Thr His Ile Ser Met Asp Trp Leu Gly Tyr Leu Ser Ala Thr
545                 550                 555                 560

Ala Asp Asp Val Thr Ala Ser Val Glu Glu Gly Ala Ser Thr Val Asp
                565                 570                 575

Val Thr Val Pro Val Ser Asn Ile Gly Ser Val Asp Tyr Thr Gly Val
            580                 585                 590

Thr Val Thr Pro Ala Asp Leu Pro Thr Gly Trp Ser Ala Ser Pro Val
        595                 600                 605

Asn Val Gly Ala Leu Ala Ser Gly Ala Ser Lys Asp Val Thr Val Thr
    610                 615                 620

Val Asn Val Pro Ala Thr Ala Lys Lys Asp Asp Val Ala Lys Ile Val
625                 630                 635                 640

Leu Arg Val Thr Gly Thr Ser Ala Ala Asn Ala Asp Ala Thr Thr Gly
                645                 650                 655

Phe Asp Gly Ser Ile Thr Val Asn Val Thr Glu Lys Ser Glu Pro Asp
            660                 665                 670
```

```
Pro Glu Pro Glu Pro Thr Ile Thr Gly Val Ser Ala Val Thr Ser Gln
        675                 680                 685

Ala Gly Val Lys Val Gly Asp Val Phe Asp Ala Ser Lys Val Ser Val
    690                 695                 700

Thr Ala Ala Met Ser Asp Gly Ser Ser Lys Ala Leu Ala Ala Gly Glu
705                 710                 715                 720

Tyr Ser Leu Ser Ala Val Asp Ala Asp Gly Lys Ala Val Asp Leu Ala
                725                 730                 735

Glu Pro Phe Ala Ala Ala Gly Val Val Thr Val Thr Val Ser Val Pro
            740                 745                 750

Val Glu Gly Ala Asn Pro Leu Thr Ala Ser Phe Thr Ile Asp Val Ala
        755                 760                 765

Glu Lys Ser Val Asp Pro Glu Pro Lys Pro Glu Pro Lys Pro Glu Pro
    770                 775                 780

Glu Lys Pro Ala Gly Pro Lys Val Asp Val Pro Thr Glu Gln Pro Gly
785                 790                 795                 800

Leu Ser Lys Thr Gly Ala Ser Thr Ala Gly Met Ser Ile Val Phe Val
                805                 810                 815

Leu Leu Ala Leu Ser Gly Val Ala Ala Leu Ser Leu Arg Arg Arg Ser
            820                 825                 830

Ala His


<210> SEQ ID NO 8
<211> LENGTH: 1782
<212> TYPE: PRT
<213> ORGANISM: Bifidobacterium bifidum
<220> FEATURE:
<221> NAME/KEY: source
<222> LOCATION: 1..1782
<223> OTHER INFORMATION: /mol_type="protein"
      /organism="Bifidobacterium bifidum"

<400> SEQUENCE: 8

Met Arg Lys Leu Ser Gly Leu Leu Val Ala Ile Ala Met Leu Ala Val
1               5                   10                  15

Leu Pro Ala Gly Thr Ile Ser Ala Asn Ala Ala Asp Glu Pro Pro Gln
            20                  25                  30

Glu Tyr Leu Gln Leu Thr Leu Thr Arg Thr Asp Ser Asn Gly Thr Pro
        35                  40                  45

Ala Glu Val Gly Asp Lys Leu Thr Tyr Ser Leu Gly Tyr Lys Asn Val
    50                  55                  60

Ser Asp Thr Gly Phe Ile Val His Pro Thr Ala Ser Asn Leu Asn Asn
65                  70                  75                  80

Val Ala Thr Pro Gln Ser Ala Ser Asn Pro Asn Pro Met Cys Arg Trp
                85                  90                  95

Gly Asn Leu Ala Ala Gly Ala Ser Ala Ala Cys Thr Trp Ser Ala Ser
            100                 105                 110

Lys Glu Phe Ala Tyr His Val Val Thr Glu Asp Asp Val Ala Asn Gly
        115                 120                 125

Phe Thr Pro Thr Ala Thr Val Ser Ala Thr Thr Gln Asp Gly Thr Asn
    130                 135                 140

Gly Val Leu Gln Ser Val Asp Ile Thr Gly Glu Thr Val Pro Ala Val
145                 150                 155                 160

Pro Ala Thr Ser Thr Leu Arg Val Ala Met Gln Arg Thr Asp Thr Leu
                165                 170                 175

Gly Asp Asn Val Lys Ile Gly Asp Arg Leu Thr Phe Asn Phe Thr Tyr
```

```
            180                 185                 190

Thr Asn Lys Thr Ala Gln Lys Ile Tyr Ala Tyr Pro Ser Glu Ser Asn
        195                 200                 205

Ile Glu Arg Val Asp Val Val Ser Tyr Pro Arg Asn Ser Cys Arg Ser
    210                 215                 220

Gly Val Glu Ala Asn Gln Thr Ala Ser Cys Gly Phe Ala Tyr His Val
225                 230                 235                 240

Ile Thr Ala Glu Asp Val Val Ala Arg Arg Tyr Thr Pro Thr Ala Thr
                245                 250                 255

Phe Arg Ala Thr Ser Asp Arg Asp Gly Thr Gln Val Leu Gln Asp Asp
            260                 265                 270

Met Thr Phe Thr Thr Gly Thr Val Thr Val Ala Gly Pro Ala Asp Asp
        275                 280                 285

Ala Ala Ser Thr Pro Thr Glu Arg Lys Asp Gly Glu Pro Leu Leu Leu
    290                 295                 300

Ala Thr Asn Lys Gln Ile Gly Asn Thr Asp Tyr Tyr Arg Ile Pro Ala
305                 310                 315                 320

Ile Ala Gln Ala Pro Asn Gly Trp Ile Leu Ala Ala Trp Asp Leu Arg
                325                 330                 335

Pro Ser Ser Ala Ala Asp Ala Pro Asn Pro Asn Ser Ile Val Gln Arg
            340                 345                 350

Ile Ser Lys Asp Gly Gly Lys Ser Trp Glu Thr Leu Ala Tyr Val Ala
        355                 360                 365

Gln Gly Arg Ser Ala Thr Asn Lys Tyr Gly Tyr Ser Asp Pro Ser Tyr
    370                 375                 380

Val Val Asp Glu Glu Ala Gly Lys Ile Phe Leu Phe Cys Val Lys Ser
385                 390                 395                 400

Tyr Asp Gln Gly Tyr Phe Gly Ser Val Leu Gly Val Glu Asp Ala Arg
                405                 410                 415

Asn Val Leu Gln Ala Val Val Met Glu Ser Asp Asp Asn Gly Ala Thr
            420                 425                 430

Trp Ser Glu Pro Arg Asn Ile Thr Lys Asp Ile Thr Lys Gly His Glu
        435                 440                 445

Asp Glu Trp Lys Ser Arg Phe Ala Ser Ser Gly His Gly Ile Gln Leu
    450                 455                 460

Lys Tyr Gly Gln Tyr Lys Gly Arg Leu Ile Gln Gln Tyr Ala Val Arg
465                 470                 475                 480

Thr Thr Ser Asn Thr Asn Ile Ala Val Ser Val Tyr Ser Asp Asp His
                485                 490                 495

Gly Lys Thr Trp Lys Ala Gly Asn Pro Val Thr Glu Val Asn Met Asp
            500                 505                 510

Glu Asn Lys Val Val Glu Leu Ser Asp Gly Arg Val Met Leu Asn Ser
        515                 520                 525

Arg Pro Gly Ala Ala Gly Tyr Arg Arg Val Ala Ile Ser Glu Asp Gly
    530                 535                 540

Gly Val Asn Tyr Gly Pro Ile Lys Ser Glu Thr Gln Leu Pro Asp Pro
545                 550                 555                 560

Asn Asn Asn Ala Gln Ile Thr Arg Ala Phe Pro Asn Ala Pro Glu Gly
                565                 570                 575

Ser Ala Lys Ala Lys Val Leu Leu Tyr Ser Ala Pro Arg Ala Ser Asn
            580                 585                 590

Glu Gly Arg Ala Asn Gly Val Val Arg Val Ser Phe Asp Asp Gly Thr
        595                 600                 605
```

```
Thr Trp Ser Ala Gly Lys Leu Phe Lys Glu Gly Ser Met Ala Tyr Ser
    610                 615                 620

Val Ile Thr Ala Leu Asn Asp Ala Ala Gly Gly Gly Tyr Gly Leu Leu
625                 630                 635                 640

Tyr Glu Gly Glu Ser Ile Thr Tyr Thr Arg Ala Ser Met Glu Trp Leu
                645                 650                 655

Gly Tyr Leu Thr Ala Thr Ala Ser Gly Thr Ala Thr Val Lys Glu Gly
            660                 665                 670

Glu Gly Thr Leu Thr Ala Pro Val Thr Val Thr Asn Asp Gly Leu Thr
        675                 680                 685

Asp Tyr Thr Asn Val Asn Val Thr Pro Thr Gly Leu Pro Ser Gly Trp
    690                 695                 700

Ser Ala Glu Ala Val Asn Val Gly Asn Leu Ala Ala Gly Gln Ser Ala
705                 710                 715                 720

Thr Val Asn Val Pro Val Thr Val Pro Ala Ala Ala Val Ser Gly Thr
                725                 730                 735

Val Ala Lys Ala Thr Met Lys Ile Thr Gly Lys Tyr Ala Gln Ser Glu
            740                 745                 750

Asp Thr Leu His Ser Phe Ala Glu Gly Glu Leu Ala Val Thr Val Thr
        755                 760                 765

Asp Pro Asp Pro Ala Ala Lys Arg Leu Lys Leu Thr Ile Glu Arg Thr
    770                 775                 780

Asp Asp Asn Gly Asp Pro Val Lys Val Gly Asp Thr Leu Thr Tyr Arg
785                 790                 795                 800

Ile Thr Tyr Glu Asn Val Gly Thr Gln Ser Phe Ala Val Tyr Pro Arg
                805                 810                 815

Glu Ser Asn Leu Asp Gly Val Thr Thr Pro Gln Ser Ala Ser Asn Pro
            820                 825                 830

Ala Pro Val Cys Arg Trp Ser Arg Leu Ala Pro Gly Thr Thr Gly Ala
        835                 840                 845

Cys Val Ser Gly Asn Gly Lys Gln Leu Ala Tyr His Thr Val Thr Glu
    850                 855                 860

Ala Asp Ala Thr Ala Gly Ser Phe Thr Pro Ser Ala Thr Ile Asp Ala
865                 870                 875                 880

Thr Ala Asp Ala Ser Gly Glu Met Val Leu Glu Ser Val Ser Ile Thr
                885                 890                 895

Gly Asp Pro Val Thr Val Ser Gln Pro Val Glu Leu Pro Ala Asp Ile
            900                 905                 910

Ala Ala Trp Lys Thr Arg Asn Glu Ala Leu Asp Asp Trp Gln Ala Leu
        915                 920                 925

Ser Glu Lys Leu Ala Lys Thr Asp Arg Ile Asn Trp Leu Phe Thr Gly
    930                 935                 940

Asp Ser Ile Thr His Gly Val Gln Phe Thr Arg Gly Tyr Arg Thr Tyr
945                 950                 955                 960

Ser Glu Leu Phe Ala Asn His Leu Asp Thr Ala Ser Val Arg Gly Val
                965                 970                 975

Ser Arg Ala Asn Asp Val Val Met Asn Thr Gly Ile Ser Ser Ala Asp
            980                 985                 990

Ala Ser Trp Pro Leu Lys Asp Gly Ala Phe Glu Lys Trp Val Ser Asp
        995                 1000                1005

Lys His Pro Asp Val Val Phe Leu Thr Phe Gly Met Asn Asp Gly Arg
    1010                1015                1020
```

```
Thr Gly Gln Ala Phe Thr Val Asp Gln Tyr Thr Ala Asn Leu Ser Thr
1025                1030                1035                1040

Leu Ile Asp Lys Ile Arg Asp Ile Gly Ala Ile Pro Val Leu Gln Thr
                1045                1050                1055

Gln Asn Tyr Thr Thr Asn Thr Thr Phe Asn Ala Asn Leu Asp Thr Tyr
            1060                1065                1070

Phe Asp Ala Glu Arg Arg Leu Ala Leu Asp Lys Asn Val Leu Leu Val
        1075                1080                1085

Asp Phe Asn Lys Gln Trp Leu Ala Leu Gly Gly Gly Asn Arg Glu Ser
    1090                1095                1100

Gly Thr Tyr Met Gly Ala Gly Asn Asp Ile His Pro Gly Glu Asn Gly
1105                1110                1115                1120

His Ile Glu Trp Ala Lys Phe Thr Leu Gly Ala Leu Asn Met Ile Ala
                1125                1130                1135

Asn Asp Asp Pro Leu Ala Arg Trp Ser Ser Ser Asp Thr Thr Leu Asp
            1140                1145                1150

Lys Pro Thr Val Thr Val Asp Ala Asp Gly Asn Gly Leu Lys Gly Ser
        1155                1160                1165

Asp Gly Leu Glu Pro Ala Pro Ala Ala Ala Lys Ser Val Gly Lys Phe
    1170                1175                1180

Leu Ser Gly Ala Gln Tyr Val Asp Leu Gly Gly Asp Val Val Ser Ala
1185                1190                1195                1200

Val Ala Gly Lys Arg Glu Ser Asn Val Thr Ile Arg Phe Arg Ala Ser
                1205                1210                1215

Ala Thr Gly Gln Pro Gln Thr Leu Phe Ser Leu Gly Asp Ser Asp Ser
            1220                1225                1230

Ala Thr Arg Ala Thr Val Arg Leu Ser Ala Thr Gly Leu Val Gln Phe
        1235                1240                1245

Leu Asn Ser Gly Asn Thr Gly Asp Phe Tyr Thr Val Gly Thr Asn Asp
    1250                1255                1260

Leu Ala Asp Gly Ala Trp His Thr Val Ser Val Asn Phe Val Ala Asn
1265                1270                1275                1280

Gly Phe Thr Ile Tyr Val Asp Gly Ala Ala Met Arg Ala Ile Ser Gly
                1285                1290                1295

Gly Thr Gly Thr Gln Leu Asn Val Pro Gly Ala Ile Thr Val Asn Thr
            1300                1305                1310

Ala Thr Ala Gly Ala Ile Arg Gly Ala Asp Ser Ala Gly Gly Ala Gln
        1315                1320                1325

Gln Leu Thr Gly Ile Val Asp Tyr Val Ala Ala Trp Ser Arg Thr Leu
    1330                1335                1340

Thr Gly Ala Glu Ala Lys Arg Ile Ser Ala Glu Thr Ser Ala Val Ala
1345                1350                1355                1360

Val Thr Lys Val Asp Ala Ala Val Asn Ala Leu Gln Pro Ile Ile Ser
                1365                1370                1375

Asp Thr Gly Ala Arg Lys Asn Ile Val Phe Val Gly Gly Glu Thr Ile
            1380                1385                1390

Glu Gly Gly Tyr Thr Asp His Leu Ile Ala Lys Asn Ile Val Gln Leu
        1395                1400                1405

Leu Asp Glu Arg Val Arg Trp Glu Tyr Val Thr Gly Leu Ser Ala Thr
    1410                1415                1420

Asp Arg Glu Arg Gln Arg Ala Lys Phe Phe Val Ala Ala Gly Gln Gly
1425                1430                1435                1440

Gly Leu Thr Ala Lys Gln Met Asp Glu Asp Tyr Ala Ala Met Val Gly
```

```
                1445                1450                1455

Glu Tyr Ser Pro Asp Ile Leu Phe Leu Ala Pro Asp Leu Tyr Asp Ala
            1460                1465                1470

Asp Gly Asn Leu Ala Glu Ser Asp Ala Ala Ala Phe Ala Gly His Ile
        1475                1480                1485

Arg Ser Val Ala Ala Lys Ala Lys Glu Ala Gly Ala Lys Val Val Leu
    1490                1495                1500

Val Thr Pro Val Thr Val Arg Gly Gly Glu Asp Glu Tyr Ala Gly Ala
1505                1510                1515                1520

Met Arg Thr Val Ala Lys Glu Asp Asp Leu Pro Leu Ile Asp Ala Gln
                1525                1530                1535

Ala Trp Ile Gly Lys Val Val Ala Ala Asp Ala Ser Val Lys Thr Ala
            1540                1545                1550

Trp Phe Asn Lys Ala Gly Gln Leu Asn Tyr Ala Gly His Leu Gly Tyr
        1555                1560                1565

Ala Arg Phe Met Met Arg Ser Leu Asp Leu Tyr Pro Ser Asn Val Ser
    1570                1575                1580

Gly Ser Arg Ile Ala Ser Leu Pro Tyr Asp Thr Ala Asn Val Thr Leu
1585                1590                1595                1600

Val Gly Ala Ser Glu Asn Gly Gly Glu Leu Pro Val Gly Arg Val Glu
                1605                1610                1615

Gly Thr Asp Arg Ala His Ile Asp Thr Met Gln Ile Gly Ala Ala Ala
            1620                1625                1630

Ser Leu Val Val Ala Asp Ser Tyr Ala Val Tyr Glu Ile Gly Glu Asp
        1635                1640                1645

Gly Gly Arg Thr Leu Val Ala Asp Gly Leu Lys Pro Ala Asp Val Leu
    1650                1655                1660

Ala Asp Gly Ile Asp Val Thr Val Asn Asp Thr Ala Ala His Arg Tyr
1665                1670                1675                1680

Glu Val Val Gly Ser Ala Asn Val Pro Glu Gly Ala Asp Ala Val Thr
                1685                1690                1695

Val Thr Tyr Thr Ala Thr Leu Ala Ala Val Glu Glu Pro Glu Pro Gly
            1700                1705                1710

Pro Asp Pro Asp Pro Thr Pro Asp Pro Ser Glu Lys Pro Asp Gly Asp
        1715                1720                1725

Gly Thr Gly Asp Gly Thr Gly Ala Gly Thr Gly Asp Val Gln Lys Pro
    1730                1735                1740

Thr Pro Asp Ala Val Ala Lys Thr Gly Ala Asp Val Phe Gly Leu Leu
1745                1750                1755                1760

Ala Ala Val Ala Val Leu Leu Ala Ala Gly Ser Val Thr Leu Ser Leu
                1765                1770                1775

Arg Arg Arg Ala Asn Arg
            1780
```

```
<210> SEQ ID NO 9
<211> LENGTH: 835
<212> TYPE: PRT
<213> ORGANISM: Bifidobacterium bifidum
<220> FEATURE:
<221> NAME/KEY: source
<222> LOCATION: 1..835
<223> OTHER INFORMATION: /mol_type="protein"
      /organism="Bifidobacterium bifidum"

<400> SEQUENCE: 9

Met Val Arg Ser Thr Lys Pro Ser Leu Leu Arg Arg Phe Gly Ala Leu
```

-continued

```
1               5                   10                  15

Val Ala Ala Ala Ala Met Leu Val Val Leu Pro Ala Gly Val Ser Thr
            20                  25                  30

Ala Ser Ala Ala Ser Asp Asp Ala Asp Met Leu Thr Val Thr Met Thr
        35                  40                  45

Arg Thr Asp Ala Leu Gly Asp Glu Val Tyr Val Gly Asp Thr Leu Thr
    50                  55                  60

Tyr Ser Phe Thr Asn Thr Asn Asn Thr Ser Ser Ala Phe Thr Ala Phe
65                  70                  75                  80

Pro Ala Glu Ser Asn Leu Ser Gly Val Leu Thr Thr Gly Thr Pro Asn
                85                  90                  95

Cys Arg Tyr Glu Asn Leu Ala Gly Gly Ala Ser Tyr Pro Cys Ser Thr
            100                 105                 110

Ala Ser His Thr Ile Thr Ala Asp Asp Leu Thr Ala Gly Ser Phe Thr
        115                 120                 125

Pro Arg Thr Val Trp Lys Ala Thr Ser Asp Arg Gly Gly Thr Gln Val
    130                 135                 140

Leu Gln Asp Asn Ile Val Ser Thr Gly Asp Thr Val Thr Val Lys Glu
145                 150                 155                 160

Gly Lys Arg Pro Asp Pro Ala Thr Ile Pro Thr Asp Arg Ala Asp Gly
                165                 170                 175

Glu Ala Val Arg Leu Ala Thr Ala Arg Gln Asn Leu Gly Thr Glu Cys
            180                 185                 190

Tyr Arg Ile Pro Ala Leu Ala Glu Ala Pro Asn Gly Trp Ile Leu Ala
        195                 200                 205

Ala Phe Asp Gln Arg Pro Asn Thr Ala Met Ala Asn Gly Ser Gly Val
    210                 215                 220

Lys Cys Trp Asp Ala Pro Gln Pro Asn Ser Ile Val Gln Arg Ile Ser
225                 230                 235                 240

Lys Asp Gly Gly Lys Ser Trp Thr Pro Ile Gln Tyr Val Ala Gln Gly
                245                 250                 255

Lys Asn Ala Pro Glu Arg Tyr Gly Tyr Ser Asp Pro Ser Tyr Val Val
            260                 265                 270

Asp Lys Glu Thr Gly Glu Ile Phe Leu Phe Phe Val His Ser Tyr Asn
        275                 280                 285

Lys Gly Phe Ala Asp Ser Gln Leu Gly Val Asp Glu Ser Asn Arg Asn
    290                 295                 300

Val Leu His Ala Val Val Val Ser Ser Lys Asp Asn Gly Glu Thr Trp
305                 310                 315                 320

Ser Lys Pro Arg Asp Ile Thr Ala Asp Ile Thr Lys Gly Tyr Glu Asn
                325                 330                 335

Glu Trp Lys Ser Arg Phe Ala Thr Ser Gly Ala Gly Ile Gln Leu Lys
            340                 345                 350

Tyr Gly Lys Tyr Lys Gly Arg Leu Ile Gln Gln Tyr Ala Val Gly Arg
        355                 360                 365

Thr Thr Gly Ser Asn Ala Ala Val Ser Val Tyr Ser Asp Asp His Gly
    370                 375                 380

Lys Thr Trp Gln Ala Gly Asn Pro Val Thr Gly Met Leu Met Asp Glu
385                 390                 395                 400

Asn Lys Val Val Glu Leu Ser Asp Gly Arg Val Met Leu Asn Ser Arg
                405                 410                 415

Pro Gly Ala Ala Gly Tyr Arg Arg Val Ala Ile Ser Glu Asp Gly Gly
            420                 425                 430
```

```
Val Asn Tyr Gly Thr Val Lys Asn Glu Thr Gln Leu Pro Asp Pro Asn
        435                 440                 445

Asn Asn Ala His Ile Thr Arg Ala Phe Pro Asn Ala Pro Glu Gly Ser
    450                 455                 460

Ala Lys Ala Lys Val Leu Leu Tyr Ser Ser Pro Arg Ala Asn Asn Glu
465                 470                 475                 480

Gly Arg Ala Asn Gly Val Val Arg Ile Ser Leu Asp Asp Gly Thr Thr
                485                 490                 495

Trp Ser Ser Gly Lys Leu Tyr Lys Glu Gly Ser Met Ala Tyr Ser Val
            500                 505                 510

Ile Thr Ala Leu Ser Asp Ala Ala Gly Gly Gly Tyr Gly Leu Leu Tyr
        515                 520                 525

Glu Gly Ala Trp Val Thr Gly Gly Gly Ile Asp Ser His Asp Ile Met
    530                 535                 540

Tyr Thr His Ile Ser Met Asp Trp Leu Gly Tyr Leu Ser Ala Thr Ala
545                 550                 555                 560

Asp Asp Val Thr Ala Ser Val Glu Glu Gly Ala Ser Thr Val Asp Val
                565                 570                 575

Thr Val Pro Val Ser Asn Val Gly Ser Val Asp Tyr Thr Gly Val Thr
            580                 585                 590

Val Thr Pro Ala Asp Leu Pro Thr Gly Trp Ser Ala Ser Pro Val Asn
        595                 600                 605

Val Gly Ala Leu Ala Ser Gly Thr Ser Lys Asp Val Thr Val Thr Val
    610                 615                 620

Asn Val Pro Ala Thr Ala Lys Lys Asp Asp Val Ala Lys Ile Val Leu
625                 630                 635                 640

Arg Val Thr Gly Thr Ser Ala Ala Asn Ala Asn Ala Thr Thr Gly Phe
                645                 650                 655

Asp Gly Ser Ile Thr Val Asn Val Thr Glu Lys Ser Glu Pro Asp Pro
            660                 665                 670

Glu Pro Glu Pro Thr Ile Thr Gly Val Ser Ala Val Thr Ser Gln Ala
        675                 680                 685

Gly Val Lys Val Gly Asp Val Phe Asp Ala Ser Lys Val Ser Val Thr
    690                 695                 700

Ala Ala Met Ser Asp Gly Ser Ser Lys Ala Leu Ala Ala Gly Glu Tyr
705                 710                 715                 720

Ser Leu Ser Ala Val Asp Ala Asp Gly Lys Ala Val Asp Leu Ala Glu
                725                 730                 735

Pro Phe Ala Ala Ala Gly Val Val Thr Val Thr Val Ser Val Pro Val
            740                 745                 750

Glu Gly Ala Gly Pro Leu Thr Ala Ser Phe Thr Ile Asp Val Ala Glu
        755                 760                 765

Lys Ser Val Asp Pro Glu Pro Lys Pro Glu Pro Glu Pro Lys Pro Glu
    770                 775                 780

Pro Glu Lys Pro Ala Gly Pro Lys Val Asp Val Pro Thr Glu Gln Pro
785                 790                 795                 800

Gly Leu Ser Lys Thr Gly Ala Ser Thr Ala Gly Met Ser Ile Val Phe
                805                 810                 815

Val Leu Leu Ala Leu Ser Gly Ile Ala Ala Leu Ser Leu Arg Arg Arg
            820                 825                 830

Ser Val His
        835
```

<210> SEQ ID NO 10
<211> LENGTH: 1060
<212> TYPE: PRT
<213> ORGANISM: Trypanosoma cruzi
<220> FEATURE:
<221> NAME/KEY: source
<222> LOCATION: 1..1060
<223> OTHER INFORMATION: /mol_type="protein"
/organism="Trypanosoma cruzi"

<400> SEQUENCE: 10

```
Met Gly Lys Thr Val Val Gly Ala Ser Arg Met Phe Trp Leu Met Phe
1               5                   10                  15

Phe Val Pro Leu Leu Leu Ala Leu Cys Pro Ser Glu Pro Ala His Ala
            20                  25                  30

Leu Ala Pro Gly Ser Ser Arg Val Glu Leu Phe Lys Arg Gln Ser Ser
        35                  40                  45

Lys Val Pro Phe Glu Lys Gly Gly Lys Val Thr Glu Arg Val Val His
    50                  55                  60

Ser Phe Arg Leu Pro Ala Leu Val Asn Val Asp Gly Val Met Val Ala
65                  70                  75                  80

Ile Ala Asp Ala Arg Tyr Glu Thr Ser Asn Asp Asn Ser Leu Ile Asp
                85                  90                  95

Thr Val Ala Lys Tyr Ser Val Asp Asp Gly Glu Thr Trp Glu Thr Gln
            100                 105                 110

Ile Ala Ile Lys Asn Ser Arg Ala Ser Ser Val Ser Arg Val Val Asp
        115                 120                 125

Pro Thr Val Ile Val Lys Gly Asn Lys Leu Tyr Val Leu Val Gly Ser
    130                 135                 140

Tyr Asn Ser Ser Arg Ser Tyr Trp Thr Ser His Gly Asp Ala Arg Asp
145                 150                 155                 160

Trp Asp Ile Leu Leu Ala Val Gly Glu Val Thr Lys Ser Thr Ala Gly
                165                 170                 175

Gly Lys Ile Thr Ala Ser Ile Lys Trp Gly Ser Pro Val Ser Leu Lys
            180                 185                 190

Glu Phe Phe Pro Ala Glu Met Glu Gly Met His Thr Asn Gln Phe Leu
        195                 200                 205

Gly Gly Ala Gly Val Ala Ile Val Ala Ser Asn Gly Asn Leu Val Tyr
    210                 215                 220

Pro Val Gln Val Thr Asn Lys Lys Lys Gln Val Phe Ser Lys Ile Phe
225                 230                 235                 240

Tyr Ser Glu Asp Glu Gly Lys Thr Trp Lys Phe Gly Glu Gly Arg Ser
                245                 250                 255

Asp Phe Gly Cys Ser Glu Pro Val Ala Leu Glu Trp Glu Gly Lys Leu
            260                 265                 270

Ile Ile Asn Thr Arg Val Asp Tyr Arg Arg Arg Leu Val Tyr Glu Ser
        275                 280                 285

Ser Asp Met Gly Asn Ser Trp Val Glu Ala Val Gly Thr Leu Ser Arg
    290                 295                 300

Val Trp Gly Pro Ser Pro Lys Ser Asn Gln Pro Gly Ser Gln Ser Ser
305                 310                 315                 320

Phe Thr Ala Val Thr Ile Glu Gly Met Arg Val Met Leu Phe Thr His
                325                 330                 335

Pro Leu Asn Phe Lys Gly Arg Trp Leu Arg Asp Arg Leu Asn Leu Trp
            340                 345                 350
```

```
Leu Thr Asp Asn Gln Arg Ile Tyr Asn Val Gly Gln Val Ser Ile Gly
        355                 360                 365

Asp Glu Asn Ser Ala Tyr Ser Ser Val Leu Tyr Lys Asp Asp Lys Leu
    370                 375                 380

Tyr Cys Leu His Glu Ile Asn Ser Asn Glu Val Tyr Ser Leu Val Phe
385                 390                 395                 400

Ala Arg Leu Val Gly Glu Leu Arg Ile Ile Lys Ser Val Leu Gln Ser
                405                 410                 415

Trp Lys Asn Trp Asp Ser His Leu Ser Ser Ile Cys Thr Pro Ala Asp
            420                 425                 430

Pro Ala Ala Ser Ser Ser Glu Arg Gly Cys Gly Pro Ala Val Thr Thr
        435                 440                 445

Val Gly Leu Val Gly Phe Leu Ser His Ser Ala Thr Lys Thr Glu Trp
    450                 455                 460

Glu Asp Ala Tyr Arg Cys Val Asn Ala Ser Thr Ala Asn Ala Glu Arg
465                 470                 475                 480

Val Pro Asn Gly Leu Lys Phe Ala Gly Val Gly Gly Gly Ala Leu Trp
                485                 490                 495

Pro Val Ser Gln Gln Gly Gln Asn Gln Arg Tyr His Phe Ala Asn His
            500                 505                 510

Ala Phe Thr Leu Val Ala Ser Val Thr Ile His Glu Val Pro Ser Val
        515                 520                 525

Ala Ser Pro Leu Leu Gly Ala Ser Leu Asp Ser Ser Gly Gly Lys Lys
    530                 535                 540

Leu Leu Gly Leu Ser Tyr Asp Glu Lys His Gln Trp Gln Pro Ile Tyr
545                 550                 555                 560

Gly Ser Thr Pro Val Thr Pro Thr Gly Ser Trp Glu Met Gly Lys Arg
                565                 570                 575

Tyr His Val Val Leu Thr Met Ala Asn Lys Ile Gly Ser Val Tyr Ile
            580                 585                 590

Asp Gly Glu Pro Leu Glu Gly Ser Gly Gln Thr Val Val Pro Asp Gly
        595                 600                 605

Arg Thr Pro Asp Ile Ser His Phe Tyr Val Gly Gly Tyr Gly Arg Ser
    610                 615                 620

Asp Met Pro Thr Ile Ser His Val Thr Val Asn Asn Val Leu Leu Tyr
625                 630                 635                 640

Asn Arg Gln Leu Asn Ala Glu Glu Ile Arg Thr Leu Phe Leu Ser Gln
                645                 650                 655

Asp Leu Ile Gly Thr Glu Ala His Met Gly Ser Ser Ser Gly Ser Ser
            660                 665                 670

Ala His Ser Thr Pro Ser Thr Pro Ala Asp Asn Gly Ala His Ser Thr
        675                 680                 685

Pro Ser Thr Pro Ala Asp Ser Ser Ala His Ser Thr Pro Ser Thr Pro
    690                 695                 700

Ala Asp Ser Ser Ala His Ser Thr Pro Ser Ala Pro Gly Asp Asn Gly
705                 710                 715                 720

Ala His Ser Thr Pro Ser Thr Pro Gly Asp Ser Ser Ala His Ser Thr
                725                 730                 735

Pro Ser Thr Pro Ala Asp Asn Gly Ala His Ser Thr Pro Ser Ala Pro
            740                 745                 750

Ala Asp Ser Asn Ala His Ser Thr Pro Ser Thr Pro Ala Asp Asn Gly
        755                 760                 765

Ala His Ser Thr Pro Ser Thr Pro Ala Asp Asn Gly Ala His Ser Thr
```

```
    770                 775                 780

Pro Ser Thr Pro Gly Asp Asn Gly Ala His Ser Thr Pro Ser Thr Pro
785                 790                 795                 800

Gly Asp Ser Ser Ala His Ser Thr Pro Ser Thr Pro Ala Asp Asn Gly
                805                 810                 815

Ala His Ser Thr Pro Ser Ala Pro Ala Asp Ser Asn Ala His Ser Thr
            820                 825                 830

Pro Ser Thr Pro Gly Asp Asn Gly Ala His Ser Thr Pro Ser Ala Pro
        835                 840                 845

Ala Asp Ser Asn Ala His Ser Thr Pro Ser Thr Pro Ala Asp Ser Ser
    850                 855                 860

Ala His Ser Thr Pro Ser Ala Pro Gly Asp Asn Gly Ala His Ser Thr
865                 870                 875                 880

Pro Ser Ala Pro Ala Asp Ser Ser Ala His Ser Thr Pro Ser Ala Pro
                885                 890                 895

Gly Asp Asn Gly Ala His Ser Thr Pro Ser Ala Pro Ala Asp Asn Gly
            900                 905                 910

Ala His Ser Thr Pro Ser Ala Pro Gly Asp Ser Asn Ala His Ser Thr
        915                 920                 925

Pro Ser Thr Pro Ala Asp Ser Ser Ala His Ser Thr Pro Ser Thr Pro
    930                 935                 940

Ala Asp Ser Ser Ala His Ser Thr Pro Ser Ala Pro Gly Asp Asn Gly
945                 950                 955                 960

Ala His Ser Thr Pro Ser Ala Pro Ala Asp Ser Ser Ala His Ser Thr
                965                 970                 975

Pro Ser Ile Pro Gly Asp Ser Ser Ala His Ser Thr Pro Ser Ala Pro
            980                 985                 990

Ala Asp Ser Ser Ala His Ser Thr Pro Ser Ala Pro Gly Asp Asn Gly
        995                 1000                1005

Ala His Ser Thr Pro Ser Thr Pro Ala Asp Asn Gly Ala Asn Gly Thr
    1010                1015                1020

Val Leu Ile Leu His Asp Gly Ala Ala Phe Ser Ala Phe Ser Gly Gly
1025                1030                1035                1040

Gly Leu Leu Leu Cys Ala Gly Ala Leu Leu Leu His Val Phe Val Met
                1045                1050                1055

Ala Val Phe Phe
            1060


<210> SEQ ID NO 11
<211> LENGTH: 642
<212> TYPE: PRT
<213> ORGANISM: Trypanosoma cruzi
<220> FEATURE:
<221> NAME/KEY: source
<222> LOCATION: 1..642
<223> OTHER INFORMATION: /mol_type="protein"
      /organism="Trypanosoma cruzi"

<400> SEQUENCE: 11

Met Leu Ala Pro Gly Ser Ser Arg Val Glu Leu Phe Lys Arg Gln Ser
1               5                   10                  15

Ser Lys Val Pro Phe Glu Lys Asp Gly Lys Val Thr Glu Arg Val Val
            20                  25                  30

His Ser Phe Arg Leu Pro Ala Leu Val Asn Val Asp Gly Val Met Val
        35                  40                  45

Ala Ile Ala Asp Ala Arg Tyr Glu Thr Ser Asn Asp Asn Ser Leu Ile
```

```
    50                  55                  60

Asp Thr Val Ala Lys Tyr Ser Val Asp Asp Gly Glu Thr Trp Glu Thr
65                  70                  75                  80

Gln Ile Ala Ile Lys Asn Ser Arg Ala Ser Ser Val Ser Arg Val Val
                85                  90                  95

Asp Pro Thr Val Ile Val Lys Gly Asn Lys Leu Tyr Val Leu Val Gly
            100                 105                 110

Ser Tyr Asn Ser Ser Arg Ser Tyr Trp Thr Ser His Gly Asp Ala Arg
        115                 120                 125

Asp Trp Asp Ile Leu Leu Ala Val Gly Glu Val Thr Lys Ser Thr Ala
    130                 135                 140

Gly Gly Lys Ile Thr Ala Ser Ile Lys Trp Gly Ser Pro Val Ser Leu
145                 150                 155                 160

Lys Glu Phe Phe Pro Ala Glu Met Glu Gly Met His Thr Asn Gln Phe
                165                 170                 175

Leu Gly Gly Ala Gly Val Ala Ile Val Ala Ser Asn Gly Asn Leu Val
            180                 185                 190

Tyr Pro Val Gln Val Thr Asn Lys Lys Lys Gln Val Phe Ser Lys Ile
        195                 200                 205

Phe Tyr Ser Glu Asp Glu Gly Lys Thr Trp Lys Phe Gly Lys Gly Arg
    210                 215                 220

Ser Ala Phe Gly Cys Ser Glu Pro Val Ala Leu Glu Trp Glu Gly Lys
225                 230                 235                 240

Leu Ile Ile Asn Thr Arg Val Asp Tyr Arg Arg Arg Leu Val Tyr Glu
                245                 250                 255

Ser Ser Asp Met Gly Asn Ser Trp Leu Glu Ala Val Gly Thr Leu Ser
            260                 265                 270

Arg Val Trp Gly Pro Ser Pro Lys Ser Asn Gln Pro Gly Ser Gln Ser
        275                 280                 285

Ser Phe Thr Ala Val Thr Ile Glu Gly Met Arg Val Met Leu Phe Thr
    290                 295                 300

His Pro Leu Asn Phe Lys Gly Arg Trp Leu Arg Asp Arg Leu Asn Leu
305                 310                 315                 320

Trp Leu Thr Asp Asn Gln Arg Ile Tyr Asn Val Gly Gln Val Ser Ile
                325                 330                 335

Gly Asp Glu Asn Ser Ala Tyr Ser Ser Val Leu Tyr Lys Asp Asp Lys
            340                 345                 350

Leu Tyr Cys Leu His Glu Ile Asn Ser Asn Glu Val Tyr Ser Leu Val
        355                 360                 365

Phe Ala Arg Leu Val Gly Glu Leu Arg Ile Ile Lys Ser Val Leu Gln
    370                 375                 380

Ser Trp Lys Asn Trp Asp Ser His Leu Ser Ser Ile Cys Thr Pro Ala
385                 390                 395                 400

Asp Pro Ala Ala Ser Ser Ser Glu Arg Gly Cys Gly Pro Ala Val Thr
                405                 410                 415

Thr Val Gly Leu Val Gly Phe Leu Ser His Ser Ala Thr Lys Thr Glu
            420                 425                 430

Trp Glu Asp Ala Tyr Arg Cys Val Asn Ala Ser Thr Ala Asn Ala Glu
        435                 440                 445

Arg Val Pro Asn Gly Leu Lys Phe Ala Gly Val Gly Gly Gly Ala Leu
    450                 455                 460

Trp Pro Val Ser Gln Gln Gly Gln Asn Gln Arg Tyr Arg Phe Ala Asn
465                 470                 475                 480
```

```
His Ala Phe Thr Val Val Ala Ser Val Thr Ile His Glu Val Pro Ser
                485                 490                 495

Val Ala Ser Pro Leu Leu Gly Ala Ser Leu Asp Ser Ser Gly Gly Lys
            500                 505                 510

Lys Leu Leu Gly Leu Ser Tyr Asp Glu Arg His Gln Trp Gln Pro Ile
        515                 520                 525

Tyr Gly Ser Thr Pro Val Thr Pro Thr Gly Ser Trp Glu Met Gly Lys
    530                 535                 540

Arg Tyr His Val Val Leu Thr Met Ala Asn Lys Ile Gly Ser Glu Tyr
545                 550                 555                 560

Ile Asp Gly Glu Pro Leu Glu Gly Ser Gly Gln Thr Val Val Pro Asp
                565                 570                 575

Glu Arg Thr Pro Asp Ile Ser His Phe Tyr Val Gly Gly Tyr Lys Arg
            580                 585                 590

Ser Asp Met Pro Thr Ile Ser His Val Thr Val Asn Asn Val Leu Leu
        595                 600                 605

Tyr Asn Arg Gln Leu Asn Ala Glu Glu Ile Arg Thr Leu Phe Leu Ser
    610                 615                 620

Gln Asp Leu Ile Gly Thr Glu Ala His Met Asp Ser Ser Ser Asp Thr
625                 630                 635                 640

Ser Ala
```

SYNTHESIS OF SIALOOLIGOSACCHARIDE DERIVATIVES

CROSS REFERENCE TO RELATED APPLICATIONS

This application is the National Phase entry of PCT/EP2011/062184, which claims priority to European Patent Application No. 11166036.1, filed May 13, 2011 and Great Britain Patent Application No. 1012036.8, filed Jul. 16, 2010. The content of these applications is incorporated herein by reference in their entirety.

FIELD OF THE INVENTION

The present invention relates to the enzymatic synthesis of sialooligosaccharide glycosides, and novel precursors and products taking part in the synthesis.

BACKGROUND OF THE INVENTION

Sialic acids are derivatives of the nine-carbon sugar neuraminic acid and encompass three parent molecules, N-acetyl-(Neu5Ac), N-glycolyl-(Neu5Gc) and deamino-neuraminic acid (3-deoxy-D-glycero-D-galacto-nonulosonic acid, KDN), which can be substituted at C-4, C-7, C-8 and C-9 by various moieties. They have many major biological roles, ranging from embryogenesis to neural plasticity to pathogen interactions. Although they may rarely occur in free form, they are usually found in chemical covalent linkage at the non-reducing terminus or in internal positions of oligosaccharide side-chains of glycoproteins and glycolipids. The linkages of sialic acids in which they are bound to penultimate sugars such as galactose, N-acetyl-galactosamine and N-acetyl-glucosamine are most commonly α-2,3- and α-2,6-ketosidic bonds.

Among sialoglycoconjugates, sialylated human milk oligosaccharides are of great importance which is directly linked to their unique biological activities such as antibacterial, antiviral, immune system and cognitive development enhancing activities. Sialylated human milk oligosaccharides are found to act as prebiotics in the human intestinal system helping to develop and maintain the intestinal flora. Furthermore they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics. In the human milk oligosaccharides the sialic acid residue is always linked to the terminal 3-O- and/or 6-O-position(s) of D-galactose via α-glycosidic linkage.

The availability of naturally occurring sialylated human milk oligosaccharides is limited. Mature human milk is the natural milk source that contains the highest concentrations of milk oligosaccharides (12-14 g/l), other milk sources are cow's milk (0.01 g/l), goat's milk and milk from other mammals. This low natural availability and difficult isolation methods are important motivations for the development of biotechnological and chemical methodologies for the production of these attractive compounds.

Approximately 200 HMOs have been detected from human milk by means of combination of techniques including microchip liquid chromatography mass spectrometry (HPLC Chip/MS) and matrix-assisted laser desorption/ionization Fourier transform ion cyclotron resonance mass spectrometry (MALDI-FT ICR MS) (Ninonuevo et al. *J. Agric. Food Chem.* 54, 7471 (2006)), from which to date at least 115 oligosaccharides have been structurally determined (Urashima et al.: *Milk Oligosaccharides*, Nova Medical Books, NY, 2011). These human milk oligosaccharides can be grouped into 13 core units (Table 1). About a quarter of oligosaccharides contains sialic acid.

TABLE 1

13 different core structures of human milk oligosaccharides (HMOs)

| No | Core name | Core structure |
|---|---|---|
| 1 | lactose (Lac) | Galβ1-4Glc |
| 2 | lacto-N-tetraose (LNT) | Galβ1-3GlcNAcβ1-3Galβ1-4Glc |
| 3 | lacto-N-neotetraose (LNnT) | Galβ1-4GlcNAcβ1-3Galβ1-4Glc |
| 4 | lacto-N-hexaose (LNH) | Galβ1-3GlcNAcβ1-3(Galβ1-4GlcNAcβ1-6)Galβ1-4Glc |
| 5 | lacto-N-neohexaose (LNnH) | Galβ1-4GlcNAcβ1-3(Galβ1-4GlcNAcβ1-6)Galβ1-4Glc |
| 6 | para-lacto-N-hexaose (para-LNH) | Galβ1-3GlcNAcβ1-3Galβ1-4GlcNAcβ1-3Galβ1-4Glc |
| 7 | para-lacto-N-neohexaose (para-LNnH) | Galβ1-4GlcNAcβ1-3Galβ1-4GlcNAcβ1-3Galβ1-4Glc |
| 8 | lacto-N-octaose (LNO) | Galβ1-3GlcNAcβ1-3(Galβ1-4GlcNAcβ1-3Galβ1-4GlcNAcβ1-6)Galβ1-4Glc |
| 9 | lacto-N-neooctaose (LNnO) | Galβ1-4GlcNAcβ1-3(Galβ1-3GlcNAcβ1-3Galβ1-4GlcNAcβ1-6)Galβ1-4Glc |
| 10 | Iso-lacto-N-octaose (iso-LNO) | Galβ1-3GlcNAcβ1-3(Galβ1-3GlcNAcβ1-3Galβ1-4GlcNAcβ1-6)Galβ1-4Glc |
| 11 | para-lacto-N-octaose (para-LNO) | Galβ1-3GlcNAcβ1-3 Galβ1-4GlcNAcβ1-3Galβ1-4GlcNAcβ1-3Galβ1-4Glc |
| 12 | Lacto-N-decaose (LND) | Galβ1-3GlcNAcβ1-3[Galβ1-4GlcNAcβ1-3(Galβ1-4GlcNAcβ1-6)Galβ1-4GlcNAcβ1-6]Galβ1-4Glc |
| 13 | Lacto-N-neodecaose (LNnD) | Galβ1-3GlcNAcβ1-3[Galβ1-3GlcNAcβ1-3(Galβ1-4GlcNAcβ1-6)Galβ1-4GlcNAcβ1-6]Galβ1-4Glc |

The isolation of sialooligosaccharides form human and other mammals' milk is rather difficult even in milligram quantities due to the presence of a large number of similar oligosaccharides. To date only analytical HPLC methodologies have been developed for the isolation of some sialooligosaccharides from natural source.

The synthesis of complex sialooligosaccharides follows multistep synthetic pathways utilising protection and deprotection strategies. Stereoselective chemical synthetic processes can become very complicated due to the extensive use of protecting groups. These strategies give sialylated oligosaccharides via stereoselective O-sialylation of appropriate protected glycosyl acceptors using glycosylhalide, thioglycoside or diethylphosphite donor activations. The use of either very expensive or very toxic chemicals for the sialylation such as mercury cyanide, mercury bromide and silver carbonate is one of the reasons that make these methodologies less attractive. Inefficient stereocontrol and/or poor yields likewise make(s) the strategies less suitable for further developments. Additionally, these strategies are characterized by severe purification difficulties.

In the case of enzymatic production of sialooligosaccharides, sialyltransferases and sialidases have been the preferred enzymes used. These complex enzymatic systems represent very expensive methodologies for scale-up production and difficult purification protocols are likewise a hindrance for further technology developments. Sialidases could not be used successfully in large scale production methodologies due to low yields and lack of regio- and stereoselectivity. Although in some cases sialyltransferase enzymes are found to be effective in the synthesis of complex sialooligosaccharides (e.g. the synthesis of 1-O-β-benzyl glycoside of 3'-O—(N-acetyl-neuraminosyl)-lactose sodium salt: WO 96/32492; the synthesis of 1-O-β-(4,5-dimethoxy-2-nitro)-benzyl glycoside of 3'-O—(N-acetyl-neuraminosyl)-lactose sodium salt: Cohen et al. *J. Org. Chem.* 65, 6145 (2000)), the need of CMP-activated sialic acid (cytidine 5'-monophosphosialic acid) as sialyl donor—whose availability is, in fact, rather limited—for transferring the sialic acid portion to the acceptor oligosaccharide restricts their usefulness.

The ability of N-acetyl-lactosamine benzyl glycoside and benzyl glycosides of mucin oligosaccharides from *T. cruzi* to act as substrate in transsialidase reaction has been studied (Lubineau et al. *Carbohydr. Res.* 300, 161 (1997); Agusti et al. *Bioorg. Med. Chem.* 15, 2611 (2007)).

Regioselective sialidation of unprotected or anomerically substituted galactose, lactose or N-acetyl-lactosamine derivatives by means of sialidases in poor yield has been reported (Thiem et al. *Angew. Chem. Int. Ed. Eng.* 30, 1503 (1991); Schmidt et al. *Chem. Comm.* 1919 (2000); Schmidt et al. *J. Org. Chem.* 65, 8518 (2000)).

Some biotechnological methodologies are also described using genetically modified bacteria, yeasts or other microorganisms. Such methods have serious drawbacks in regulatory processes due to limiting commercialisation opportunities.

Sialoglycoconjugates are known to be unstable under certain reaction conditions, such as to acid and base. Indeed, they are able to self-hydrolyse. Accordingly, conditions for preparation and purification of these compounds must be carefully selected.

In summary, isolation technologies have never been able to provide large quantities of sialooligosaccharides due to the large number of oligosaccharides present in the pool of natural origin, e.g. in human milk. Additionally, the presence of regioisomers characterized by extremely similar structures further made separation technologies unsuccessful. Enzymatic methodologies suffer from the low availability of enzymes, extremely high sugar nucleotide donor prices and regulatory difficulties due to the use of enzymes produced in genetically modified organisms. The preparation of oligosaccharides via biotechnology has huge regulatory obstacles due to the potential formation of several unnatural glycosylation products. Generally, all the chemical methods developed for the synthesis of sialooligosaccharides have several drawbacks which prevented the preparation of even multigram quantities of the target compounds (e.g. see the synthesis of 3'-O- and 6'-O-(N-acetyl-neuraminosyl)-lactose through the corresponding benzyl glycoside: Rencurosi et al. *Carbohydr. Res.* 337, 473 (2002)).

During the past decades the interest in the preparation and commercialisation of sialylated human milk oligosaccharides has been increasing steadily. There is still a need for novel methodologies which can simplify preparation and overcome or avoid purification problems encountered in prior art methods.

SUMMARY OF THE INVENTION

In one aspect, the present invention relates to a method for the synthesis of compounds of general formula 1A and salts thereof.

1A

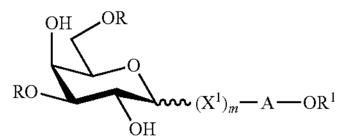

wherein one of the R groups is an α-sialyl moiety and the other is H, $X^1$ represents a carbohydrate linker, A is a D-glucopyranosyl unit optionally substituted with fucosyl, $R^1$ is a protecting group that is removable by hydrogenolysis, the integer m is 0 or 1, characterized in that a sialyl donor of formula SA-$OR^2$ or salts thereof, wherein $R^2$ can be a mono-, di- or oligosaccharide, glycolipid, glycoprotein or glycopeptide, cyclic or acyclic aliphatic group, or aryl residue, and SA is an α-sialyl moiety, is reacted with a sialyl acceptor of general formula 2A or a salt thereof

2A

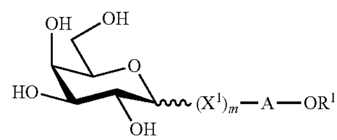

wherein $X^1$, A, m and $R^1$ are as defined above, under the catalysis of an enzyme having transsialidase activity.

In another aspect, the present invention provides compounds of general formula 1A' and salts thereof

1A'

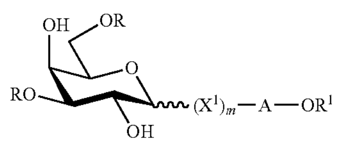

wherein one of the R groups is an α-sialyl moiety and the other is H, $R^1$ is a protecting group that is removable by hydrogenolysis, A is a D-glucopyranosyl unit optionally substituted with fucosyl, integer m is 0 or 1, and X' represents a carbohydrate linker, provided that 1-O-β-benzyl and 1-O-β-

(4,5-dimethoxy-2-nitro)-benzyl glycosides of 3'-O—(N-acetyl-neuraminosyl)-lactose sodium salt, and 1-O-β-benzyl glycoside of 6'-O—(N-acetyl-neuraminosyl)-lactose sodium salt are excluded.

BRIEF DESCRIPTION OF THE FIGURES

The invention will be described in further detail hereinafter with reference to:

FIG. 1 which shows the 400 MHz $^1$H-NMR spectrum of benzyl 3'''-O-sialyl-β-LNnT according to the present invention.

DETAILED DESCRIPTION OF THE INVENTION

Whatever route is taken to synthesise an oligosaccharide, the final target unprotected oligosaccharide is soluble only in water, which presents challenges for the later steps of the synthesis. Organic solvents commonly used in synthetic manufacturing processes are not suitable for the reactions of the very final stages of the oligosaccharide synthesis.

The present invention provides new sialooligosaccharides protected in the anomeric position and methodology suitable for manufacturing thereof. The invention is based upon the utilisation of water soluble 1-O-protected oligosaccharide intermediates in transsialidation reaction, wherein the 1-O-protecting group chosen may be removed by hydrogenolysis. Preferably, the 1-O-protecting group should also provide to the oligosaccharide intermediate physical and chemical properties assisting powerful purification processes. For example, the introduction of an aromatic group such as a benzyl or substituted benzyl group as a hydrophobic moiety enables the derivatives to be soluble in organic protic solvents like alcohols while their water solubility also remains. This opens the possibility of using mobile phases having a wide range of water/alcohol proportions which can be applied in separation/purification techniques such as size exclusion or reverse phase chromatography. Moreover, with careful design of substituents on the aromatic group, crystalline compounds can in some cases be realized, which allows the development of powerful manufacturing procedures using crystallisation alone for product purifications. Furthermore, the benzylic 1-O-protecting group can be removed by catalytic reduction (hydrogenolysis) in the last step under mild and delicate conditions that prevent by-product formation, which is undoubtedly an advantage when at least one sialyl group is present in the target oligosaccharide. It is possible for the catalytic reduction to take place in aqueous solution.

General Terms

Throughout the present application the term "α-sialyl moiety" or "sialyl moiety" present in the sialyl donors and in the compounds of general formula 1, refers to glycosyl moieties of any naturally occurring or modified neuraminic or sialic acid derivatives and analogues thereof having an α-glycosidic linkage, as depicted by the example of N-acetyl neuraminic acid in Scheme 1. Preferred neuraminic acids are N-acetyl-(Neu5Ac), N-glycolyl-(Neu5Gc) and deamino-neuraminic acid (3-deoxy-D-glycero-D-galacto-nonulosonic acid, KDN). Also included are Neu5Ac, Neu5Gc and KDN derivatives that are derivatized with linkers, reactive functional groups, detectable labels or targeting moieties, and/or substituted at C-4, C-7-, C-8 and/or C-9, especially at C-9, with acyloxy, alkoxy, halogen or azido. More preferred O-substituents are acetyl (at C-4, C-7-, C-8 and/or C-9), lactyl (at C-9), methyl (at C-8), sulphate (at C-8) or phosphate (at C-8). The preferred substituents on the amino group are acyls including glycolyl and acetoacetyl as well.

Scheme 1

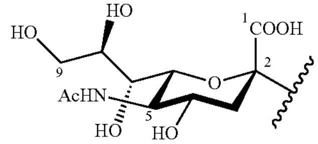

The "protecting group that is removable by hydrogenolysis" refers to groups whose C—O bond to the 1-oxygen is cleaved by addition of hydrogen in the presence of catalytic amounts of palladium, Raney nickel or another appropriate metal catalyst known for use in hydrogenolysis, resulting in the regeneration of the OH group. Such protecting groups are well known to the skilled man and are discussed in *Protective Groups in Organic Synthesis*, P G M Wuts and T W Greene, John Wiley & Sons 2007. Suitable protecting groups include benzyl, diphenylmethyl (benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). Particularly preferred protecting groups are benzyl or 2-naphthylmethyl groups optionally substituted with one or more groups selected from phenyl, alkyl or halogen. More preferably, the protecting group is selected from unsubstituted benzyl, unsubstituted 2-naphthylmethyl, 4-chlorobenzyl, 3-phenylbenzyl and 4-methylbenzyl. These particularly preferred and more preferable protecting groups have the advantage that the by-products of the hydrogenolysis are exclusively toluene, 2-methylnaphthalene, or substituted toluene or 2-methylnaphthalene derivatives, respectively. Such by-products can easily be removed even in multi ton scales from water soluble oligosaccharide products via evaporation and/or extraction processes.

Throughout the present description, the term "alkyl" means a linear or branched chain saturated hydrocarbon group with 1-6 carbon atoms, such as methyl, ethyl, n-propyl, i-propyl, n-butyl, i-butyl, s-butyl, t-butyl, n-hexyl, etc.

The term "aryl" refers to a homoaromatic group such as phenyl or naphthyl.

In the present description, the term "acyl" represents an R'—C(═O)-group, wherein R' may be H, alkyl (see above) or aryl (see above), such as formyl, acetyl, propionyl, butyryl, pivaloyl, benzoyl, etc. The alkyl or aryl residue may either be unsubstituted or may be substituted with one or more groups selected from alkyl (only for aryl residues), halogen, nitro, aryl, alkoxy, amino, alkylamino, dialkylamino, carboxyl, alkoxycarbonyl, carbamoyl, N-alkylcarbamoyl, N,N-dialkylcarbamoyl, azido, halogenalkyl or hydroxyalkyl, giving rise to acyl groups such as chloroacetyl, trichloroacetyl, 4-chlorobenzoyl, 4-nitrobenzoyl, 4-phenylbenzoyl, 4-benzamidobenzoyl, 4-(phenylcarbamoyl)-benzoyl, glycolyl, acetoacetyl, etc.

The term "alkyloxy" or "alkoxy" means an alkyl group (see above) attached to the parent molecular moiety through an oxygen atom, such as methoxy, ethoxy, t-butoxy, etc.

"Halogen" means fluoro, chloro, bromo or iodo.

"Amino" refers to a —$NH_2$ group.

"Alkylamino" means an alkyl group (see above) attached to the parent molecular moiety through an —NH-group, such as methylamino, ethylamino, etc.

"Dialkylamino" means two alkyl groups (see above), either identical or different ones, attached to the parent molecular moiety through a nitrogen atom, such as dimethylamino, diethylamino, etc.

"Acylamino" refers to an acyl group (see above) attached to the parent molecular moiety through an —NH-group, such as acetylamino (acetamido), benzoylamino (benzamido), etc.

"Carboxyl" denotes an —COOH group.

"Alkyloxycarbonyl" means an alkyloxy group (see above) attached to the parent molecular moiety through a —C(=O)-group, such as methoxycarbonyl, t-butoxycarbonyl, etc.

"Carbamoyl" is an $H_2N$—C(=O)-group.

"N-Alkylcarbamoyl" means an alkyl group (see above) attached to the parent molecular moiety through a —HN—C(=O)-group, such as N-methylcarbamoyl, etc.

"N,N-Dialkylcarbamoyl" means two alkyl groups (see above), either identical or different ones, attached to the parent molecular moiety through a >N—C(=O)-group, such as N,N-methylcarbamoyl, etc.

In the present description the term "salt" in connection with compounds of general formulae 1 and 2 and of formula SA-$OR^2$, which contain at least one sialyl residue, means an associated ion pair consisting of the negatively charged acid residue and one or more cations in any stoichiometric proportion. Cations, as used in the present context are atoms or molecules with positive charge. The cation may be inorganic as well as organic cation. Preferred inorganic cations are ammonium ion, alkali metal, alkali earth metal and transition metal ions, more preferably $Na^+$, $K^+$, $Ca^{2+}$, $Mg^{2+}$, $Ba^{2+}$, $Fe^{2+}$, $Zn^{2+}$, $Mn^{2+}$ and $Cu^{2+}$, most preferably $K^+$, $Ca^{2+}$, $Mg^{2+}$, $Ba^{2+}$, $Fe^{2+}$ and $Zn^{2+}$. Basic organic compounds in positively charged form may be relevant organic cations. Such preferred positively charged counterparts are diethyl amine, triethyl amine, diisopropyl ethyl amine, ethanolamine, diethanolamine, triethanolamine, imidazol, piperidine, piperazine, morpholin, benzyl amine, ethylene diamine, meglumin, pyrrolidine, choline, tris-(hydroxymethyl)-methyl amine, N-(2-hydroxyethyl)-pyrrolidine, N-(2-hydroxyethyl)-piperidine, N-(2-hydroxyethyl)-piperazine, N-(2-hydroxyethyl)-morpholine, L-arginine, L-lysine, oligopeptides having L-arginine or L-lysine unit or oligopeptides having free amino group on N-terminal, etc., all in protonated form. Such salt formations can be used to modify characteristics of the complex molecule as a whole, such as stability, compatibility to excipients, solubility and ability to form crystals.

Transsialidation Reactions

In accordance with the present invention there is provided a process for synthesizing sialooligosaccharides of general formula 1 and salts thereof wherein one of the R groups is an α-sialyl moiety and the other is H, X represents a carbohydrate linker, $R^1$ is a protecting group that is removable by hydrogenolysis and the integer n is 0 or 1, characterized in that a sialyl donor of formula SA-$OR^2$ and salts thereof, wherein $R^2$ can be a mono-, di- or oligosaccharide, glycolipid, glycoprotein or glycopeptide, cyclic or acyclic aliphatic group, or aryl residue, and SA is an α-sialyl moiety, is reacted with a sialyl acceptor of general formula 2 and salts thereof, under the catalysis of an enzyme having transsialidase activity. The process is depicted in Scheme 2.

Scheme 2

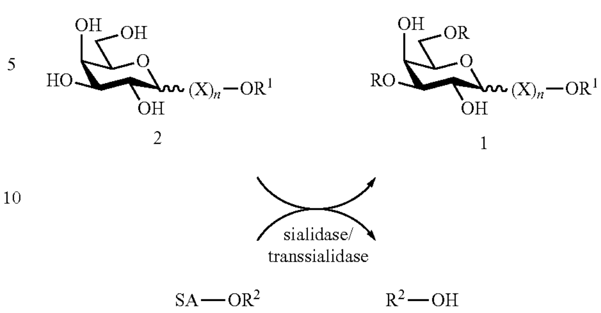

An advantage of providing compounds of general formula 1 is the more simple purification of the sialylated oligosaccharide 1-O-protected glycosides compared to the unglycosylated sialooligosaccharides. Since there is no formation of free sialic acid as a side product, and due to the different polarity of the reaction compounds, isolation of the products by reverse phase or size exclusion chromatography is possible. In the case of reverse phase chromatography when water is used, compounds of general formula 1 migrate much more slowly than the very polar compounds present in the reaction mixture, thus the polar compounds can be eluted smoothly. Compounds of general formula 1 can be then washed from the column with e.g. alcohol.

Enzymes Having Transsialidase Activity

Enzymes having transsialidase activity and suitable for the purpose of the method of making sialooligosaccharides claimed in the present application can be selected from sialidase and transsialidase enzymes.

Sialidases (EC 3.2.1.18), classified in the GH33 family, are retaining enzymes with the ability of hydrolyzing the α-linkage of the terminal sialic acid, mainly those bound to galactose with α-2-3 or α-2-6 linkage, of various sialoglycoconjugates. They are found particularly in diverse virus families and bacteria, and also in protozoa, some invertebrates and mammals. Some bacterial sialidases can be used to scavenge sialic acids from sialylated glycoprotein, glycolipids or other glycoconjugates for nutrients for bacterial cell growth.

Although sialidases are characterized by their hydrolytic activity, under appropriate reaction conditions they are able to catalyze the transfer of a sialic acid unit to an asialo acceptor by a transsialidation reaction giving rise to the formation of sialoglycoconjugates. Sialidases from pathogen bacteria or viruses such as *Bacteroides fragilis, Clostridium* species (e.g. *C. perfringens*), *Corynebacterium diphtherias, Haemophilus parasuis, Pasteurella multocida, Pseudomonas aeruginosa, Salmonella typhimurium, Streptococcus pneumoniae, Tannerella forsythia, Vibrio cholerae* or Newcastle disease virus and from non-pathogenic bacteria or viruses such as *Actinomyces viscosus, Arthrobacter* species or *Micromonospora viridifaciens* are capable of acting as a catalyst for a sialylation reaction due to their transsialidase activity with α-2-3 and/or α-2-6 selectivity. As to the regioselectivity, the ratio between the α-2-3- and α-2-6-linked products varies depending on the enzymes and/or the acceptors. For example sialidases from *A. ureafaciens, C. perfringens* and *V. cholerae* have good α-2-6 selectivity, whereas those from *S. typhimurium* and Newcastle disease virus have good to excellent preference for formation of the α-2-3 linkage.

Recently, sialidases from *Bifidobacterium* species like *Bifidobacterium bifidum* and *Bifidobacterium longum* subsp. *infantis* have been identified, cloned and characterized. These sialidases can cleave and so recognize both α-2,3- and α-2,6-linked sialosides. Sialidases from *Bifidobacterium longum* subsp. *infantis* have a consistent preference for α-2,6-linkage whereas sialidases from *Bifidobacterium bifidum* have a consistent preference for α-2,3-linkage.

In order to improve regioselectivity and/or conversion of the transsialidation reaction the sialidases may be subjected to alteration by various engineering techniques.

In rational engineering novel altered enzymes (mutants) are created by point mutation. The mutation generally affects the active site of the enzyme. Replacement of the catalytic nucleophile with a non-nucleophilic residue results in the formation of an inactive mutant or an altered enzyme with reduced transglycosylation activity due the lack of an appropriate environment for the formation of the reactive host-guest complex for transglycosylation. However, in the presence of a more active sialyl donor than the natural one, the mutated enzyme is able to transfer efficiently the sialyl residue to a suitable acceptor. Rational engineering of enzymes generally requires reliance on the static 3D protein structure. These altered enzymes may be devoid of product hydrolysis activity.

A second technique called directed evolution strategy comprises random mutagenesis of the selected natural sialidase enzyme thus creating a library of enzyme variants each of which are altered in a single or multiple positions. They may be inserted into suitable microorganisms such as *E. coli* or *S. cerevisiae* for producing recombinant variants with slightly altered properties. Clones expressing improved enzymes are then identified with a fast and reliable screening method, selected and brought into a next round of the mutation process. The recurring cycles of mutation, recombination and selection are continued as far as mutant(s) with the desired activity and/or specificity is/are evolved.

With regard to transsialidases, the first transsialidase enzyme described was found in *Trypanosoma cruzi*, a protozoa which causes Chagas disease. Since that time transsialidases have been detected in several other trypanosome types such as *Trypanosoma brucei gambiense, Trypanosoma brucei rhodesiense, Trypanosoma brucei brucei* and *Trypanosoma congolense*. Moreover, the existence of transsialidases has been shown in *Endotrypanum* types, in *Corynebacterium diphtherias* and even in the human plasma.

Transsialidases differ from sialidases in that, in addition to the hydrolytic activity towards sialic acids of the sialidases, the former have more considerable sialic acid transfer activity. Transsialidases can transfer sialic acids, preferably α-2,3-bonded sialic acids, from a donor molecule to an acceptor derivative, which is preferably a terminal galactose moiety with β-interglycosidic linkage. As a result of this transfer, an α-glycosidic bond is be formed between the sialic acid and the acceptor. However, if there is no suitable acceptor, the transsialidase hydrolyses the sialic acid.

It is possible to produce directed transsialidase enzyme mutants wherein the hydrolase activity is effaced in favour of the transsialidase action, e.g. by altering the amino acid sequence. After creating a library of altered genes by mutagenesis and/or recombination, they may be inserted into suitable microorganisms such as *E. coli* or *S. cerevisiae* for producing recombinant variants with slightly altered properties. Clones expressing improved enzymes are then identified, isolated and can be used for the desired purpose. For example, based on sequence and structure comparisons, sialidase from *Trypanosoma rangeli* may be mutated at six positions, wherein the resulting mutant is able to display a significant level of trans-sialidase activity (Paris et al. *J. Mol. Biol.* 345, 923 (2005)).

Preferably, the enzyme having transsialidase activity may be selected from sialidases or transsialidases derived from *Bifidobacterium longum* subsp. *infantis* ATCC 15697, *Bifidobacterium bifidum* JCM1254, *Bifidobacterium bifidum* S17, *Bifidobacterium bifidum* PRL2010, *Bifidobacterium bifidum* NCIMB 41171, *Trypanosoma cruzi*, etc.

More preferably the enzyme having transsialidase activity may be selected from sialidases or transsialidases as defined according to the following deposit numbers: gi|213524659 (*Bifidobacterium longum* subsp. *infantis* ATCC 15697, SEQ ID NO: 1), gi|213523006 *Bifidobacterium longum* subsp. *infantis* ATCC 15697, SEQ ID NO: 2), gi|309252191 (*Bifidobacterium bifidum* S17, SEQ ID NO: 3), gi|309252190 (*Bifidobacterium bifidum* S17, SEQ ID NO: 4), gi|310867437 (*Bifidobacterium bifidum* PRL2010, SEQ ID NO: 5), gi|310867438 (*Bifidobacterium bifidum* PRL2010, SEQ ID NO: 6), gi|224283484 (*Bifidobacterium bifidum* NCIMB 41171, SEQ ID NO: 7), gi|224283485 (*Bifidobacterium bifidum* NCIMB 41171, SEQ ID NO: 8), gi|334283443 gi|47252690 (*Bifidobacterium bifidum* JCM1254, SEQ ID NO: 9), gi|47252690 (*T. cruzi*, SEQ ID NO: 10), gi|432485 (*T. cruzi*, SEQ ID NO: 11). Particularly preferred sialidases/transsialidases with transsialidase activity are listed in the following Table 2:

TABLE 2

Preferred sialidases/transsialidases

| GI number in GenBank Database | Organism | SEQ ID NO: |
|---|---|---|
| gi\|213524659 | *Bifidobacterium longum* subsp. *infantis* ATCC 15697 | 1 |
| gi\|213523006 | *Bifidobacterium longum* subsp. *infantis* ATCC 15697 | 2 |
| gi\|309252191 | *Bifidobacterium bifidum* S17 | 3 |
| gi\|309252190 | *Bifidobacterium bifidum* S17 | 4 |
| gi\|310867437 | *Bifidobacterium bifidum* PRL2010 | 5 |
| gi\|310867438 | *Bifidobacterium bifidum* PRL2010 | 6 |
| gi\|224283484 | *Bifidobacterium bifidum* NCIMB 41171 | 7 |
| gi\|224283485 | *Bifidobacterium bifidum* NCIMB 41171 | 8 |
| gi\|334283443 | *Bifidobacterium bifidum* JCM1254 | 9 |
| gi\|47252690 | *Trypanosoma cruzi* | 10 |
| gi\|432485 | *Trypanosoma cruzi* | 11 |

It is envisaged that sialidase/transsialidase enzyme mutants retaining transsialidase activity and having a sequence similarity/homology to the sequence of the above mentioned enzyme sequences having transsialidase activity of at least 70%, more preferably at least 80%, even more preferably at least 85%, even more preferably at least 90% and most preferably at least 95% or even 97%, 98% or 99% as compared to the entire wild type sequence on amino acid level.

Preferably, the sequence similarity is at least 90%, more preferably 95%, 97%, 98% or most preferably 99%. Preferably, said trans-sialidase activity is at least 75% of that of the native form of the enzyme, more preferably at least 90% and still more preferably at least 100%.

Sialidases and transsialidases possess a broader donor and acceptor specificity than the sialyl transferases used in prior art processes, and so can be used in a particularly wide variety of reactions. Sialidases/transsialidases are therefore more advantageous for industrial utilisation than are sialyltransferases previously used.

Donors for Sialidases/Transsialidases

It is known that, upon infection of an organism with *T. cruzi*, the transsialidase in *T. cruzi* scavenges sialic acids from sialoglycoconjugates of the host's organism and efficiently sialylates its own surface mucin in order to mask its own epitope.

After numerous intensive investigations it has been found that a huge number of natural and synthetic sialic acid containing derivatives can act as sialyl donors in transsialidation reactions. Thus sialyl donor compounds of general formula SA-$OR^2$ defined above can provide a substrate to be transferred by transsialidases to the acceptor. Transsialidases do not transfer pure sialic acid or CMP-sialic acid (which is, in fact, a β-sialide) to the acceptor, the presence of a sialic acid with an α-anomeric aglycon or α-anomeric substituent is a requisite for the transsialidase reactions. Typical natural sialyl donors can be selected from, but are not limited to, 3'-O-sialyl-lactose, fetuin, gangliosides, O- or N-linked glycopeptides, all of which contain a sialic acid α-2,3-linked to a terminal β-galactoside residue, or polysialic acid with α-2,8-linkage. Among synthetic sialosides 2-O-(4-methylumbelliferyl)- or 2-O-(optionally substituted phenyl)-α-D-sialosides, more commonly 2-O-(p-nitrophenyl)-α-D-sialoside, are of preference.

Acceptors for Sialidases/Transsialidases

Transsialidase acceptors used in transsialidation reaction disclosed above are characterized by general formula 2 and salts thereof which are $R^1$-galactopyranosides (when n is 0) or oligosaccharide $R^1$-glycosides whose terminal sugar moiety on the non-reducing end is galactopyranose (when n equals 1). The terminal galactopyranosyl unit is bound preferably with a β-glycosidic linkage.

The anomeric hydroxyl group of compounds of general formula 2 are protected with $R^1$ groups that can be removed by hydrogenolysis. As set out previously, such groups include optionally substituted benzyl and naphthylmethyl groups. Benzyl or 2-naphthylmethyl groups optionally substituted with phenyl, alkyl or halogen are preferred $R^1$-groups, and among them unsubstituted benzyl, unsubstituted 2-naphthylmethyl, 4-chlorobenzyl, 3-phenylbenzyl or 4-methylbenzyl groups are of particular preference.

When n is 1, the structural element X, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl glucosamine, galactose, fucose and sialic acid.

In a preferred method n is 1 and linker X corresponds to formula —$(X^1)_m$-A-forming acceptors of general formula 2A or salts thereof

2A

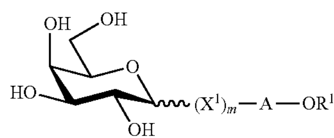

wherein A is a D-glucopyranosyl unit optionally substituted with fucosyl, $X^1$ represents a carbohydrate linker, and integer m is 0 or 1. Group —$OR^1$ is linked to the anomeric carbon ($C_1$) atom of the D-glucopyranosyl ring, preferably in β orientation.

When m is 0, the terminal D-galactopyranosyl unit is directly coupled to group A through an interglycosidic linkage. Preferably, the interglycosidic linkage is a 1-4 linkage thus forming compounds of general formula 2B

2B

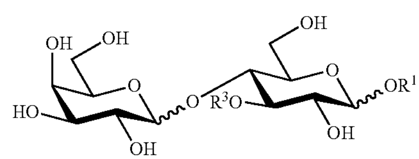

wherein $R^3$ is fucosyl or H. More preferably the interglycosidic linkage between the galactose and the glucose portion is β thus giving rise to a lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 2C or salts thereof

2C

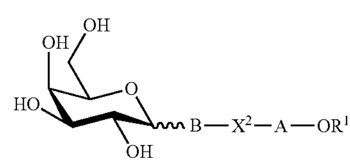

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the terminal galactosyl group is attached to group B through 1-3 or 1-4 interglycosidic linkage forming thus a lacto-N-biosyl or N-acetyl-lactosaminyl terminal disaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred method group $X^2$ is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 2D or salts thereof

2D

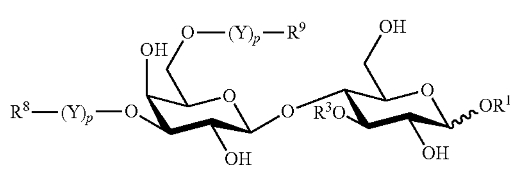

wherein $R^1$ is a group removable by hydrogenolysis, $R^3$ is H or fucosyl unit, Y is independently an N-acetyl-lactosaminyl group optionally substituted with a sialyl and/or fucosyl residue, integer p is independently 0, 1 or 2, $R^8$ is selected form the groups characterized by general formulae 5 and 6,

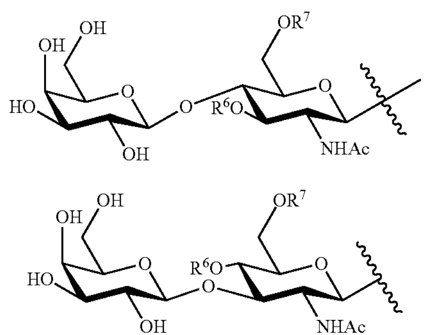

wherein $R^6$ is H or fucosyl residue, $R^7$H or α-sialyl moiety, and $R^9$ is selected from H, α-sialyl moiety, a group of general formula 5 and a group of general formula 6.

According to a further preferred method, the compound of general formula 2D and salts thereof as defined above is characterized by its linkages and attached moieties, wherein

- an N-acetyl-lactosaminyl group in group Y, when attached to another N-acetyl-lactosaminyl group (p=2), is coupled with 1-3 interglycosidic linkage,
- the group of general formula 5, when attached to Y (p=1, 2), is coupled with 1-3 interglycosidic linkage,
- the group of general formula 6, when attached to Y (p=1, 2), is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl group present in Y is linked to the galactose of the N-acetyl-lactosaminyl group with 2-6 interglycosidic linkage.

In a further aspect, the compound of general formula 2B, 2C or 2D and salts thereof as defined above represents the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having unsubstituted terminal galactosyl residue. Preferably, the sialyl substituent is N-acetyl neuraminyl group.

Particularly preferably, the compound of general formula 2B, 2C or 2D and salts thereof as defined above is selected from the group of $R^1$-glycosides of Galβ1-4Glc (lactose), Galβ1-4(Fucα1-3)Glc (3-O-fucosyllactose), Galβ1-3GlcNAcβ1-3Galβ1-4Glc (LNT), Galβ1-4GlcNAcβ1-3Galβ1-4Glc (LNnT), Galβ1-3(Fucα1-4)GlcNAcβ1-3Galβ1-4Glc (LNFP II), Galβ1-4(Fucα1-3)GlcNAcβ1-3Galβ1-4Glc (LNFP III), Galβ1-3GlcNAcβ1-3Galβ1-4(Fucα1-4)Glc (LNFP V), Galβ1-3(Fucα1-4)GlcNAcβ1-3Galβ1-4(Fucα1-3)Glc (LNDFH II), Galβ1-3(Neu5Acα2-6)GlcNAcβ1-3Galβ1-4Glc (LSTb), Galβ1-3(Neu5Acα2-6)(Fucα1-4)GlcNAcβ1-3Galβ1-4Glc, Galβ1-3(Neu5Acα2-6)GlcNAcβ1-3Galβ1-4(Fucα1-3)Glc, Galβ1-4GlcNAcβ1-3Galβ1-4(Fucα1-3)Glc, Galβ1-4(Fucα1-3)GlcNAcβ1-3Galβ1-4(Fucα1-3)Glc (LNDFH III), or salts thereof. The $R^1$-glycosides may be alpha or beta-anomers. Preferably, said $R^1$-glycosides are the beta-anomers.

A typical synthesis of compounds of general formula 2 comprises the treatment of galactose, or oligosaccharides having a galactopyranosyl unit at the nonreducing terminal, with acetic anhydride and sodium acetate at 50-125° C., followed by Lewis acid catalyzed glycosylation using $R^1$—OH, preferably benzyl/substituted benzyl alcohols, in organic solvent such as DCM, toluene, THF, etc. Subsequently, compounds of general formula 2 are obtained via a final Zemplén deprotection of the glycosylated products.

According to another typical anomeric O-protection procedure, fully or partially protected galactose or oligosaccharides having a galactopyranosyl unit at the nonreducing end with a free anomeric OH in a dipolar aprotic solvent such as DMF, DMSO, N-methylpyrrolidone, hexamethylphosphoramide (HMPA), N,N'-dimethylhexahydropyrimidine-2-one (DMPU), THF, dioxane, acetonitrile, etc., or mixture thereof, is O-alkylated in the presence of a strong base and $R^1$—X wherein X is a leaving group selected from halogen, alkylsulfonyloxy like mesyl, triflyl, etc. and arylsulfonyl like benzenesulfonyl, tosyl, etc. Preferred alkylating agents are benzyl or 1- or 2-naphthylmethyl halogenides optionally substituted with one or more groups selected from phenyl, alkyl or halogen. The strong base is able to deprotonate the anomeric OH chemoselectively due to its more acidic character when an equivalent amount or a slight excess (1 to 1.5 equiv.) of base is used. The strong base suitable for activating the anomeric OH is typically taken from the group of alkali metal or alkaline earth metal hydrides or alkoxides such as NaH, KH, $CaH_2$, NaOMe, $NaO^tBu$, $KO^tBu$, inorganic hydroxides, potassium carbonate, etc. The alkylation agent is added in an equivalent amount or a slight excess (1 to 1.5 equiv.). The reaction is carried out between −10 and 80° C., preferably at a low temperature during whole course of the reaction or at a low temperature during the addition of the reagents/reactants and an elevated temperature in the later stages of the course of the reaction. Benzyl/substituted benzyl glycosides of general formula 2 can be obtained after usual work-up.

In a further aspect, the present invention relates to providing compounds of general formula 2A' and salts thereof

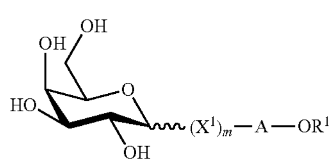

wherein A is a D-glucopyranosyl unit optionally substituted with fucosyl, $X^1$ represents a carbohydrate linker, integer m is 0 or 1, provided that a) when m is 0, then group A is substituted with fucosyl, and b) the compound differs to 1-O-β-benzyl-LNT, 1-O-β-(4-hydroxymethylbenzyl)-LNnT and 1-O-β-benzyl-LNnT. Group —$OR^1$ is linked to the anomeric carbon ($C_1$) atom of the D-glucopyranosyl ring, preferably in β orientation.

When m is 0, the terminal D-galactopyranosyl unit is directly coupled to group A through an interglycosidic linkage. Preferably, the interglycosidic linkage is a 1-4 linkage thus forming compounds of general formula 2B' and salts thereof

2B'

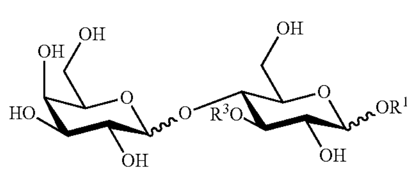

wherein $R^3$ is fucosyl. More preferably the interglycosidic linkage between the galactose and the glucose portion is β thus giving rise to a lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 2C' and salts thereof

2C'

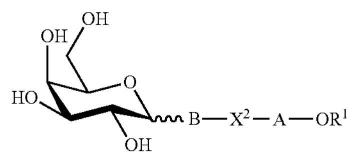

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the terminal galactosyl group is attached to group B through 1-3 or 1-4 interglycosidic linkage forming thus a lacto-N-biosyl or N-acetyl-lactosaminyl terminal disaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred method group $X^2$ is galactose optionally substituted with sialyl or oligosaccharide residue representing a linear or a branched structure having the saccharide building units selected from N-acetyl-lactosamine, lacto-N-biose, fucose and sialic acid, forming thus human milk oligosaccharide derivatives represented by general formula 2D' or salts thereof.

2D'

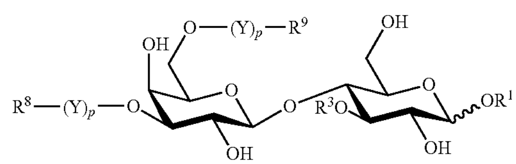

wherein $R^1$ is a group removable by hydrogenolysis, $R^3$ is H or fucosyl unit, Y is independently an N-acetyl-lactosaminyl group optionally substituted with a sialyl and/or fucosyl residue, integer p is independently 0, 1 or 2, $R^8$ is selected form the groups characterized by general formulae 5 and 6,

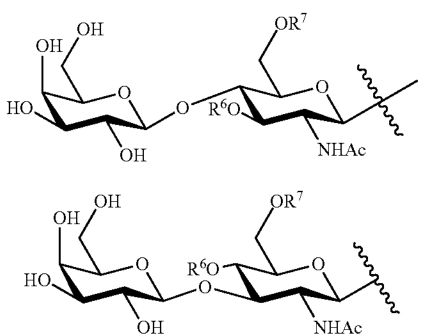

wherein $R^6$ is H or fucosyl residue, $R^7$H or α-sialyl moiety, and $R^9$ is selected from H, α-sialyl moiety, a group of general formula 5 and a group of general formula 6.

According to a further preferred embodiment, the compound of general formula 2D' and salts thereof as defined above is characterized by its linkages and attached moieties, wherein

- an N-acetyl-lactosaminyl group in group Y, when attached to another N-acetyl-lactosaminyl group, is coupled with 1-3 interglycosidic linkage,
- the group of general formula 5, when attached to Y, is coupled with 1-3 interglycosidic linkage,
- the group of general formula 6, when attached to Y, is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl present in Y is linked to the galactose of the N-acetyl-lactosaminyl group with 2-6 interglycosidic linkage.

In a further aspect, the compound of general formula 2C' or 2D' and salts thereof as defined above represents the $R^1$-glycosides lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having unsubstituted terminal galactosyl residue. Preferably, the sialyl substituent is N-acetyl neuraminyl group.

Particularly preferably, the compound of general formula 2A' and salts thereof as defined above is selected from the group of $R^1$-glycosides of Galβ1-4(Fucα1-3)Glc (3-O-fucosyllactose), Galβ1-3GlcNAcβ1-3Galβ1-4Glc (LNT), Galβ1-4GlcNAcβ1-3Galβ1-4Glc (LNnT), Galβ1-3(Fucα1-4)GlcNAcβ1-3Galβ1-4Glc (LNFP II), Galβ1-4(Fucα1-3)GlcNAcβ1-3Galβ1-4Glc (LNFP III), Galβ1-3GlcNAcβ1-3Galβ1-4(Fucα1-3)Glc (LNFP V), Galβ1-3(Fucα1-4)GlcNAcβ1-3Galβ1-4(Fucα1-3)Glc (LNDFH II), Galβ1-3(Neu5Acα2-6)GlcNAcβ1-3Galβ1-4Glc (LSTb), Galβ1-3(Neu5Acα2-6)(Fucα1-4)GlcNAcβ1-3Galβ1-4Glc, Galβ1-3(Neu5Acα2-6)GlcNAcβ1-3Galβ1-4(Fucα1-3)Glc, Galβ1-4GlcNAcβ1-3Galβ1-4(Fucα1-3)Glc, Galβ1-4(Fucα1-3)GlcNAcβ1-3Galβ1-4(Fucα1-3)Glc (LNDFH III), or salts thereof. The $R^1$-glycosides may be alpha or beta-anomers. Preferably, said $R^1$-glycosides are the beta-anomers.

Products of Transsialidation Reaction

As set forth above, the transsialidation reaction claimed in the present application produces compounds of general formula 1 and salts thereof

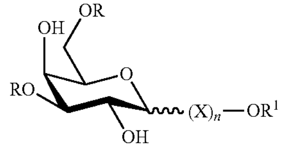

wherein one of the R groups is an α-sialyl moiety and the other is H, X represents a carbohydrate linker, $R^1$ is a protecting group that is removable by hydrogenolysis and the integer n is 0 or 1, from compounds of general formula 2 and salts thereof. $R^1$ group includes optionally substituted benzyl and naphthylmethyl groups, among which benzyl or 2-naphthylmethyl groups optionally substituted with phenyl, alkyl or halogen are preferred $R^1$-groups, and among them unsubstituted benzyl, unsubstituted 2-naphthylmethyl, 4-chlorobenzyl, 3-phenylbenzyl or 4-methylbenzyl groups are of particular preference.

When n is 1, the structural element X, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl glucosamine, galactose, fucose and sialic acid.

In a preferred method n is 1 and linker X corresponds to formula —$(X^1)_m$-A-forming sialylated products of general formula 1A and salts thereof

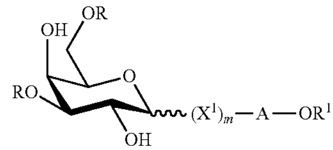

wherein A is a D-glucopyranosyl unit optionally substituted with fucosyl, $X^1$ represents a carbohydrate linker, and integer m is 0 or 1. Group —$OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1B and salts thereof.

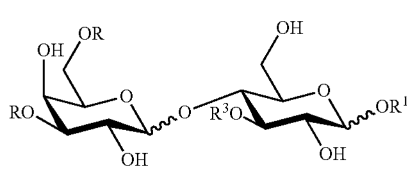

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1C and salts thereof

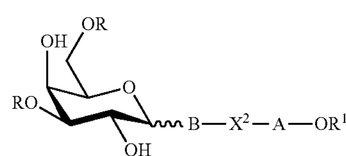

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred method to synthesize sialyl oligosaccharide derivatives, group $X^2$ in compounds of general formula 1C and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1D and salts thereof

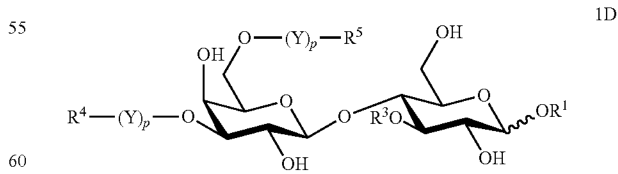

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^4$ is selected form the groups characterized by general formulae 3 and 4,

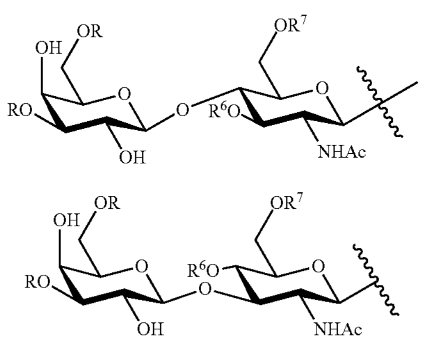

wherein $R^6$ is H or fucosyl residue, $R^7$H or α-sialyl moiety, one of the R groups is an α-sialyl moiety and the other is H, and $R^5$ is selected from H, α-sialyl moiety, group of general formula 3 and group of general formula 4.

According to a further preferred method, the compound of general formula 1D and salts thereof as defined above is characterized by its linkages and attached moieties, wherein an N-acetyl-lactosaminyl group in group Y (p=2), when attached to another N-acetyl-lactosaminyl group, is coupled with 1-3 interglycosidic linkage, the group of general formula 3, when attached to Y (p=1, 2), is coupled with 1-3 interglycosidic linkage, the group of general formula 4, when attached to Y (p=1, 2), is coupled with 1-3 interglycosidic linkage, the fucosyl residue if attached to a N-acetyl-lactosaminyl group present in Y is linked to the N-acetyl-glucosamine of the N-acetyl-lactosaminyl group with 1-3 interglycosidic linkage, the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1B, 1C or 1D and salts thereof as defined above represents the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 3-OH or 6-OH of a terminal galactosyl residue. Preferably, the sialyl substituent(s) is/are N-acetyl-neuraminyl group(s).

Particularly preferably, the compound of general formula 1B, 1C or 1D and salts thereof as defined above is selected from the group of R'-glycosides of Neu5Acα2-3Galβ1-4Glc (3'-O—(N-acetyl-neuraminosyl)-lactose), Neu5Acα2-6Galβ1-4Glc (6'-O—(N-acetyl-neuraminosyl)-lactose), Neu5Acα2-3Galβ1-4(Fucα1-3)Glc (3-O-fucosyl-3'-O—(N-acetyl-neuraminosyl)-lactose), Neu5Acα2-3Galβ1-3GlcNAcβ1-3Galβ1-4Glc (LST a), Neu5Acα2-6Galβ1-3GlcNAcβ1-3Galβ1-4Glc, Neu5Acα2-3Galβ1-4GlcNAcβ1-3Galβ1-4Glc, Neu5Acα2-6Galβ1-4GlcNAcβ1-3Galβ1-4Glc (LST c), Neu5Acα2-3Galβ1-3(Fucα1-4)GlcNAcβ1-3Galβ1-4Glc (FLST a), Neu5Acα2-6Galβ1-3(Fucα1-4)GlcNAcβ1-3Galβ1-4Glc, Neu5Acα2-3Galβ1-4(Fucα1-3)GlcNAcβ1-3Galβ1-4Glc, Neu5Acα2-Galβ1-4(Fucα1-3)GlcNAcβ1-3Galβ1-4Glc, Neu5Acα2-3Galβ1-3GlcNAcβ1-3Galβ1-4(Fucα1-3)Glc, Neu5Acα2-6Galβ1-3GlcNAcβ1-3Galβ1-4(Fucα1-4)Glc, Neu5Acα2-3Galβ1-3(Fucα1-4)GlcNAcβ1-3Galβ1-4(Fucα1-3)Glc, Neu5Acα2-6Galβ1-3 (Fucα1-4)GlcNAcβ1-3Galβ1-4 (Fucα1-3)Glc, Neu5Acα2-3Galβ1-3 (Neu5Acα2-6) GlcNAcβ1-3Galβ1-4Glc (DSLNT), Neu5Acα2-6Galβ1-3 (Neu5Acα2-6)GlcNAcβ1-3Galβ1-4Glc, Neu5Acα2-3Galβ1-3(Neu5Acα2-6)(Fucα1-4)GlcNAcβ1-3Galβ1-4Glc (FDSLNT I), Neu5Acα2-6Galβ1-3(Neu5Acα2-6)(Fucα1-4)GlcNAcβ1-3Galβ1-4Glc, Neu5Acα2-3Galβ1-3 (Neu5Acα2-6)GlcNAcβ1-3Galβ1-4(Fucα1-3)Glc (FD-SLNT II), Neu5Acα2-6Galβ1-3(Neu5Acα2-6)GlcNAcβ1-3Galβ1-4(Fucα1-3)Glc, Neu5Acα2-3Galβ1-4GlcNAcβ1-3Galβ1-4(Fucα1-3)Glc, Neu5Acα2-6Galβ1-4GlcNAcβ1-3Galβ1-4(Fucα1-3)Glc (FLST c), Neu5Acα2-3Galβ1-4 (Fucα1-3)GlcNAcβ1-3Galβ1-4(Fucα1-3)Glc, Neu5Acα2-6Galβ1-4(Fucα1-3)GlcNAcβ1-3Galβ1-4(Fucα1-3)Glc, Neu5Acα2-3Galβ1-4(Fucα1-3)GlcNAcβ1-3Galβ1-4Glc, Neu5Acα2-6Galβ1-4(Fucα1-3)GlcNAcβ1-3Galβ1-4Glc or salts thereof. The $R^1$-glycosides may be alpha- or beta-anomers. Preferably, said $R^1$-glycosides are the beta-anomers.

In case of selective α-2-3 sialidation, the transsialidation reaction claimed in the present application produces compounds of general formula 1-3 and salts thereof

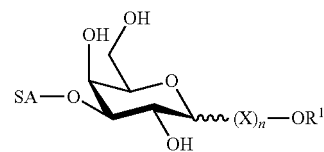

wherein SA is an α-sialyl moiety, X represents a carbohydrate linker, $R^1$ is a protecting group that is removable by hydrogenolysis and the integer n is 0 or 1, from compounds of general formula 2 and salts thereof. $R^1$ group includes optionally substituted benzyl and naphthylmethyl groups, among which benzyl or 2-naphthylmethyl groups optionally substituted with phenyl, alkyl or halogen are preferred $R^1$-groups, and among them unsubstituted benzyl, unsubstituted 2-naphthylmethyl, 4-chlorobenzyl, 3-phenylbenzyl or 4-methylbenzyl groups are of particular preference.

When n is 1, the structural element X, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl glucosamine, galactose, fucose and sialic acid.

In a preferred method n is 1 and linker X corresponds to formula $—(X^1)_m$-A-forming sialylated products of general formula 1-3A and salts thereof

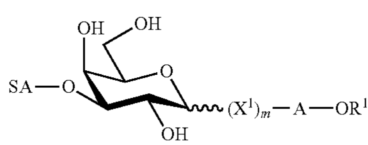

wherein A is a D-glucopyranosyl unit optionally substituted with fucosyl, $X^1$ represents a carbohydrate linker, and integer m is 0 or 1. Group $—OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1-3B and salts thereof 1-3B

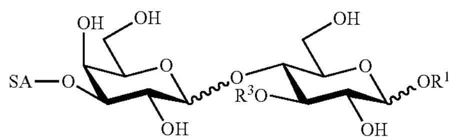

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1-3C and salts thereof 1-3C

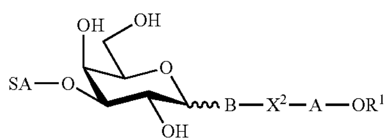

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred method to synthesize sialyl oligosaccharide derivatives, group $X^2$ in compounds of general formula 1-3C and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1-3D and salts thereof 1-3D

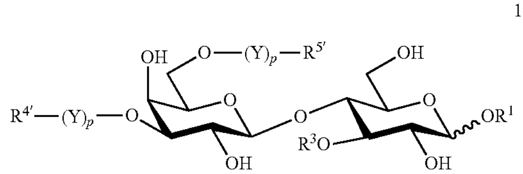

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^{4'}$ is selected form the groups characterized by general formulae 3-3 and 4-3, 3-3

4-3

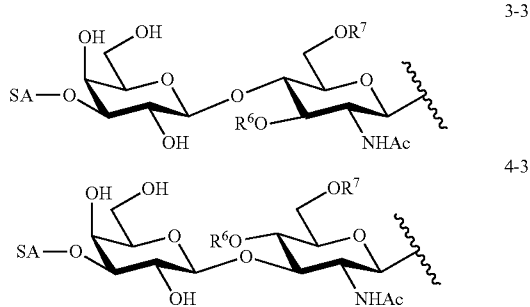

wherein $R^6$ is H or fucosyl residue, $R^7$H or α-sialyl moiety, SA is α-sialyl moiety and $R^{5'}$ is selected from H, α-sialyl moiety, group of general formula 3-3 and group of general formula 4-3.

According to a further preferred embodiment, the compound of general formula 1-3D and salts thereof as defined above is characterized by its linkages and attached moieties, wherein

- an N-acetyl-lactosaminyl group in group Y (p=2), when attached to another N-acetyl-lactosaminyl group, is coupled with 1-3 interglycosidic linkage,
- the group of general formula 3-3, when attached to Y (p=1, 2), is coupled with 1-3 interglycosidic linkage,
- the group of general formula 4-3, when attached to Y (p=1, 2), is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1-3B, 1-3C or 1-3D and salts thereof as defined above represents the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 3-OH of a terminal galactosyl residue, and salts thereof. Preferably, the sialyl substituent(s) is/are N-acetyl neuraminyl group(s).

Particularly preferably, the compound of general formula 1-3B, 1-3C or 1-3D and salts thereof as defined above is selected from the group of $R^1$-glycosides of Neu5Acα2-3Galβ1-4Glc (3'-O—(N-acetyl-neuraminosyl)-lactose), Neu5Acα2-3Galβ1-4(Fucα1-3)Glc (3-O-fucosyl-3'-O—(N-acetyl-neuraminosyl)-lactose), Neu5Acα2-3Galβ1-3GlcNAcβ1-3Galβ1-4Glc (LST a), Neu5Acα2-3Galβ1-4GlcNAcβ1-3Galβ1-4Glc, Neu5Acα2-3Galβ1-3(Fucα1-4)GlcNAcβ1-3Galβ1-4Glc (FLST a), Neu5Acα2-3Galβ1-4(Fucα1-3)GlcNAcβ1-3Galβ1-4Glc, Neu5Acα2-3Galβ1-3GlcNAcβ1-3Galβ1-4(Fucα1-3)Glc, Neu5Acα2-3Galβ1-3(Fucα1-4)GlcNAcβ1-3Galβ1-4(Fucα1-3)Glc, Neu5Acα2-3Galβ1-3(Neu5Acα2-6)GlcNAcβ1-3Galβ1-4Glc (DSLNT), Neu5Acα2-3Galβ1-3(Neu5Acα2-6)(Fucα1-4)GlcNAcβ1-3Galβ1-4Glc (FDSLNT I), Neu5Acα2-3Galβ1-3(Neu5Acα2-6)GlcNAcβ1-3Galβ1-4(Fucα1-3)Glc (FDSLNT II), Neu5Acα2-3Galβ1-4GlcNAcβ1-3Galβ1-4(Fucα1-3)Glc, Neu5Acα2-3Galβ1-4(Fucα1-3)GlcNAcβ1-3Galβ1-4(Fucα1-3)Glc, Neu5Acα2-3Galβ1-4(Fucα1-3)GlcNAcβ1-3Galβ1-4Glc and salts thereof. The $R^1$-glycosides may be alpha- or beta-anomers. Preferably, said $R^1$-glycosides are the beta-anomers.

In case of selective α-2-6 sialidation, the transsialidation reaction claimed in the present application produces compounds of general formula 1-6 and salts thereof 1-6

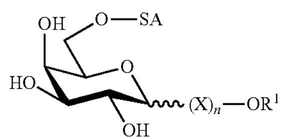

wherein SA is an α-sialyl moiety, X represents a carbohydrate linker, $R^1$ is a protecting group that is removable by hydrogenolysis and the integer n is 0 or 1, from compounds of general formula 2 and salts thereof. $R^1$ group includes optionally substituted benzyl and naphthylmethyl groups, among which benzyl or 2-naphthylmethyl groups optionally substituted with phenyl, alkyl or halogen are preferred $R^1$-groups, and among them unsubstituted benzyl, unsubstituted 2-naphthylmethyl, 4-chlorobenzyl, 3-phenylbenzyl or 4-methylbenzyl groups are of particular preference.

When n is 1, the structural element X, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl glucosamine, galactose, fucose and sialic acid.

In a preferred method n is 1 and linker X corresponds to formula —$(X^1)_m$-A-forming sialylated products of general formula 1-6A and salts thereof.

1-6A

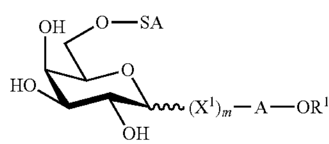

wherein A is a D-glucopyranosyl unit optionally substituted with fucosyl, $X^1$ represents a carbohydrate linker, and integer m is 0 or 1. Group —$OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1-6B and salts thereof 1-6B

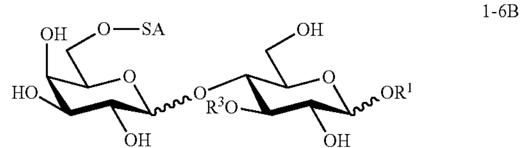

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1-6C and salts thereof.

1-6C

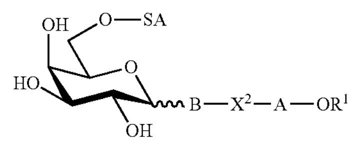

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred method to synthesize sialyl oligosaccharide derivatives, group $X^2$ in compounds of general formula 1-6C and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1-6D and salts thereof 1-6D

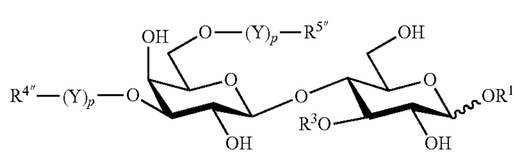

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^{4''}$ is selected from the groups characterized by general formulae 3-6 and 4-6,

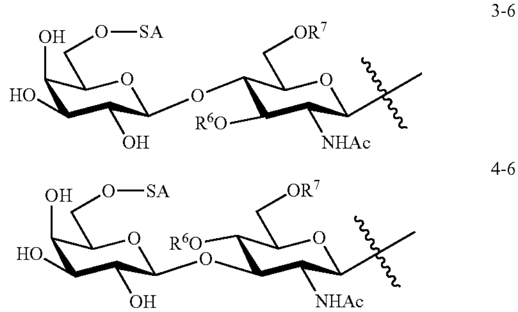

wherein $R^6$ is H or fucosyl residue, $R^7$H or α-sialyl moiety, SA is α-sialyl moiety and $R^{5''}$ is selected from H, α-sialyl moiety, group of general formula 3-6 and group of general formula 4-6, or salts thereof.

According to a further preferred embodiment, the compound of general formula 1-6D and salts thereof as defined above is characterized by its linkages and attached moieties, wherein

- an N-acetyl-lactosaminyl group in group Y (p=2), when attached to another N-acetyl-lactosaminyl group, is coupled with 1-3 interglycosidic linkage,
- the group of general formula 3-6, when attached to Y (p=1, 2), is coupled with 1-3 interglycosidic linkage,
- the group of general formula 4-6, when attached to Y (p=1, 2), is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1-6B, 1-6C or 1-6D and salts thereof as defined above represents the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 6-OH of a terminal galactosyl residue, and salts thereof. Preferably, the sialyl substituent(s) is/are N-acetyl neuraminyl group(s).

Particularly preferably, the compound of general formula 1-6B, 1-6C or 1-6D and salts thereof as defined above is selected from the group of $R^1$-glycosides of Neu5Acα2-6Galβ1-4Glc (6'-O—(N-acetyl-neuraminosyl)-lactose), Neu5Acα2-6Galβ1-4(Fucα1-3)Glc, Neu5Acα2-6Galβ1-3GlcNAcβ1-3Galβ1-4Glc, Neu5Acα2-6Galβ1-4GlcNAcβ1-3Galβ1-4Glc (LST c), Neu5Acα2-6Galβ1-3(Fucα1-4)GlcNAcβ1-3Galβ1-4Glc, Neu5Acα2-6Galβ1-4(Fucα1-3)GlcNAcβ1-3Galβ1-4Glc, Neu5Acα2-6Galβ1-3GlcNAcβ1-3Galβ1-4(Fucα1-3)Glc, Neu5Acα2-6Galβ1-3(Fucα1-4)GlcNAcβ1-3Galβ1-4(Fucα1-3)Glc, Neu5Acα2-6Galβ1-3(Neu5Acα2-6)GlcNAcβ1-3Galβ1-4Glc, Neu5Acα2-6Galβ1-3(Neu5Acα2-6)(Fucα1-4)GlcNAcβ1-3Galβ1-4Glc, Neu5Acα2-6Galβ1-3(Neu5Acα2-6)GlcNAcβ1-3Galβ1-4(Fucα1-3)Glc, Neu5Acα2-6Galβ1-4GlcNAcβ1-3Galβ1-4(Fucα1-3)Glc (FLST c), Neu5Acα2-6Galβ1-4(Fucα1-3)GlcNAcβ1-3Galβ1-4(Fucα1-3)Glc, Neu5Acα2-6Galβ1-4(Fucα1-3)GlcNAcβ1-3Galβ1-4Glc or salts thereof. The $R^1$-glycosides may be alpha- or beta-anomers. Preferably, said $R^1$-glycosides are the beta-anomers.

It should be emphasized that some compounds represented by general formula 1 and salts thereof defined above and obtainable in the transsialidation reaction disclosed in the present application are novel. Thus the invention relates to providing novel compounds of general formula 1A' and salts thereof

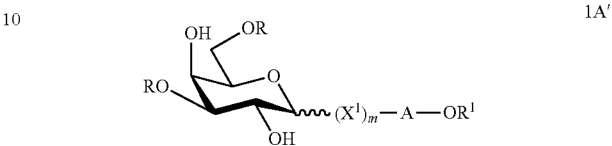

wherein one of the R groups is an α-sialyl moiety and the other is H, $R^1$ is a protecting group that is removable by hydrogenolysis, A is a D-glucopyranosyl unit optionally substituted with fucosyl, integer m is 0 or 1, and $X^1$ represents a carbohydrate linker, provided that 1-O-β-benzyl and 1-O-β-(4,5-dimethoxy-2-nitro)-benzyl glycosides of 3'-O—(N-acetyl-neuraminosyl)-lactose sodium salt, and 1-O-β-benzyl glycoside of 6'-O—(N-acetyl-neuraminosyl)-lactose sodium salt are excluded. Group —$OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1B' and salts thereof

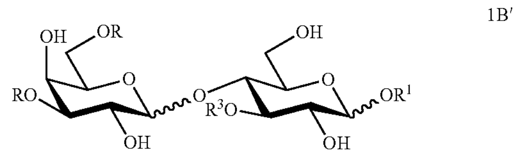

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1C' and salts thereof.

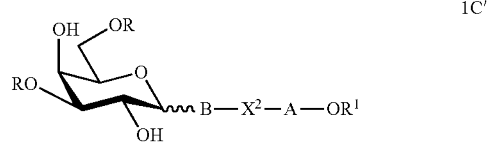

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred embodiment, group $X^2$ in compounds of general formula 1C' and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1D' and salts thereof

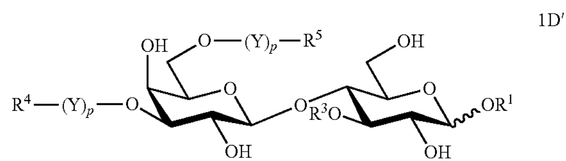

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^4$ is selected form the groups characterized by general formulae 3 and 4,

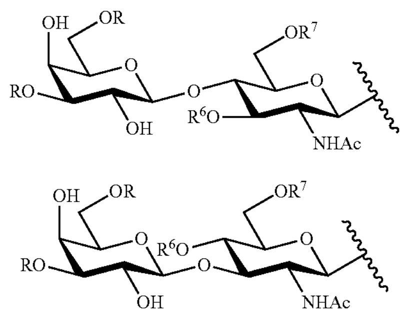

wherein $R^6$ is H or fucosyl residue, $R^7$H or α-sialyl moiety, one of the R groups is an α-sialyl moiety and the other is H, and $R^5$ is selected from H, α-sialyl moiety, group of general formula 3 and group of general formula 4.

According to a further preferred embodiment, the compound of general formula 1D' and salts thereof as defined above is characterized by its linkages and attached moieties, wherein

- an N-acetyl-lactosaminyl group in group Y (p=2), when attached to another N-acetyl-lactosaminyl group, is coupled with 1-3 interglycosidic linkage,
- the group of general formula 3, when attached to Y (p=1, 2), is coupled with 1-3 interglycosidic linkage,
- the group of general formula 4, when attached to Y (p=1, 2), is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1B', 1C' or 1D' and salts thereof as defined above is selected from the group consisting of the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 3-OH or 6-OH of a terminal galactosyl residue, and salts thereof. Preferably, the sialyl substituent(s) is/are N-acetyl neuraminyl group(s).

Particularly preferably, the compound of general formula 1A' and salts thereof as defined above is selected from the group consisting of $R^1$-glycosides of Neu5Acα2-3Galβ1-4Glc (3'-O—(N-acetyl-neuraminosyl)-lactose), Neu5Acα2-6Galβ1-4Glc (6'-O—(N-acetyl-neuraminosyl)-lactose), Neu5Acα2-3Galβ1-4(Fucα1-3)Glc (3-O-fucosyl-3'-O—(N-acetyl-neuraminosyl)-lactose), Neu5Acα2-3Galβ1-3GlcNAcβ1-3Galβ1-4Glc (LST a), Neu5Acα2-6Galβ1-3GlcNAcβ1-3Galβ1-4Glc, Neu5Acα2-3Galβ1-4GlcNAcβ1-3Galβ1-4Glc, Neu5Acα2-6Galβ1-4GlcNAcβ1-3Galβ1-4Glc (LST c), Neu5Acα2-3Galβ1-3(Fucα1-4)GlcNAcβ1-3Galβ1-4Glc (FLST a), Neu5Acα2-6Galβ1-3(Fucα1-4)GlcNAcβ1-3Galβ1-4Glc, Neu5Acα2-3Galβ1-4(Fucα1-3)GlcNAcβ1-3Galβ1-4Glc, Neu5Acα2-Galβ1-4(Fucα1-3)GlcNAcβ1-3Galβ1-4Glc, Neu5Acα2-3Galβ1-3GlcNAcβ1-3Galβ1-4(Fucα1-4)Glc, Neu5Acα2-6Galβ1-3GlcNAcβ1-3Galβ1-4(Fucα1-4)Glc, Neu5Acα2-3Galβ1-3(Fucα1-4)GlcNAcβ1-3Galβ1-4(Fucα1-3)Glc, Neu5Acα2-6Galβ1-3 (Fucα1-4)GlcNAcβ1-3Galβ1-4 (Fucα1-3)Glc, Neu5Acα2-3Galβ1-3 (Neu5Acα2-6) GlcNAcβ1-3Galβ1-4Glc (DSLNT), Neu5Acα2-6Galβ1-3 (Neu5Acα2-6)GlcNAcβ1-3Galβ1-4Glc, Neu5Acα2-3Galβ1-3(Neu5Acα2-6)(Fucα1-4)GlcNAcβ1-3Galβ1-4Glc (FDSLNT I), Neu5Acα2-6Galβ1-3(Neu5Acα2-6)(Fucα1-4)GlcNAcβ1-3Galβ1-4Glc, Neu5Acα2-3Galβ1-3 (Neu5Acα2-6)GlcNAcβ1-3Galβ1-4(Fucα1-3)Glc (FDSLNT II), Neu5Acα2-6Galβ1-3(Neu5Acα2-6)GlcNAcβ1-3Galβ1-4(Fucα1-3)Glc, Neu5Acα2-3Galβ1-4GlcNAcβ1-3Galβ1-4(Fucα1-3)Glc, Neu5Acα2-6Galβ1-4GlcNAcβ1-3Galβ1-4(Fucα1-3)Glc (FLST c), Neu5Acα2-3Galβ1-4 (Fucα1-3)GlcNAcβ1-3Galβ1-4(Fucα1-3)Glc, Neu5Acα2-6Galβ1-4(Fucα1-3)GlcNAcβ1-3Galβ1-4(Fucα1-3)Glc, Neu5Acα2-3Galβ1-4(Fucα1-3)GlcNAcβ1-3Galβ1-4Glc, Neu5Acα2-6Galβ1-4(Fucα1-3)GlcNAcβ1-3Galβ1-4Glc or salts thereof. The $R^1$-glycosides may be alpha- or beta-anomers. Preferably, said $R^1$-glycosides are the beta-anomers.

In one embodiment within the group of compounds of general formula 1A' and salts thereof the present invention relates to α-2-3-sialylated compounds of general formula 1'-3A and salts thereof

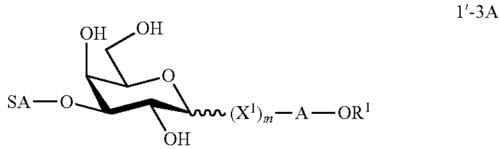

wherein A is a D-glucopyranosyl unit optionally substituted with fucosyl, $X^1$ represents a carbohydrate linker, and integer m is 0 or 1. Group —$OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1'-3B and salts thereof

1'-3B

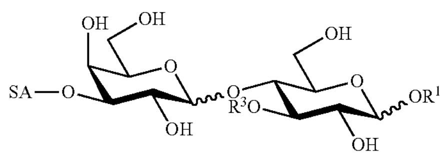

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1'-3C and salts thereof

1'-3C

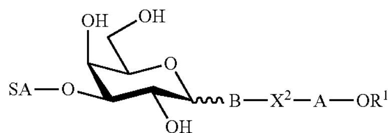

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred embodiment, group $X^2$ in compounds of general formula 1'-3C and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1'-3D and salts thereof

1'-3D

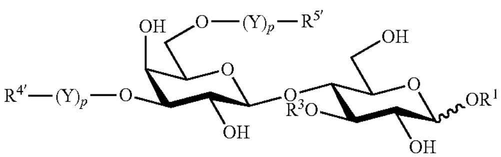

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^{4'}$ is selected from the groups characterized by general formulae 3-3 and 4-3, 3-3

4-3

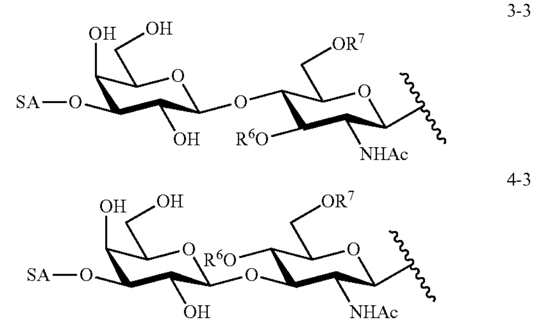

wherein $R^6$ is H or fucosyl residue, $R^7$H or α-sialyl moiety, SA is α-sialyl moiety and $R^{5'}$ is selected from H, α-sialyl moiety, group of general formula 3-3 and group of general formula 4-3.

According to a further preferred embodiment, the compound of general formula 1'-3D and salts thereof as defined above is characterized by its linkages and attached moieties, wherein an N-acetyl-lactosaminyl group in group Y (p=2), when attached to another N-acetyl-lactosaminyl group, is coupled with 1-3 interglycosidic linkage, the group of general formula 3-3, when attached to Y (p=1, 2), is coupled with 1-3 interglycosidic linkage, the group of general formula 4-3, when attached to Y (p=1, 2), is coupled with 1-3 interglycosidic linkage, the fucosyl residue if attached to a N-acetyl-lactosaminyl group present in Y is linked to the N-acetyl-glucosamine of the N-acetyl-lactosaminyl group with 1-3 interglycosidic linkage, the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1'-3B, 1'-3C or 1'-3D and salts thereof as defined above is selected from the group consisting of the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 3-OH of a terminal galactosyl residue, and salts thereof. Preferably, the sialyl substituent(s) is/are N-acetyl-neuraminyl group(s).

Particularly preferably, the compound of general formula 1'-3B, 1'-3C or 1'-3D and salts thereof as defined above is selected from the group consisting of $R^1$-glycosides of Neu5Acα2-3Galβ1-4Glc (3'-O—(N-acetyl-neuraminosyl)-lactose), Neu5Acα2-3Galβ1-4 (Fucα1-3)Glc (3-O-fucosyl-3'-O—(N-acetyl-neuraminosyl)-lactose), Neu5Acα2-3Galβ1-3GlcNAcβ1-3Galβ1-4Glc (LST a), Neu5Acα2-3Galβ1-4GlcNAcβ1-3Galβ1-4Glc, Neu5Acα2-3Galβ1-3 (Fucα1-4)GlcNAcβ1-3Galβ1-4Glc (FLST a), Neu5Acα2-3Galβ1-4(Fucα1-3)GlcNAcβ1-3Galβ1-4Glc, Neu5Acα2-3Galβ1-3GlcNAcβ1-3Galβ1-4(Fucα1-3)Glc, Neu5Acα2-3Galβ1-3 (Fucα1-4)GlcNAcβ1-3Galβ1-4(Fucα1-3)Glc, Neu5Acα2-3Galβ1-3 (Neu5Acα2-6)GlcNAcβ1-3Galβ1-4Glc (DSLNT), Neu5Acα2-3Galβ1-3 (Neu5Acα2-6) (Fucα1-4)GlcNAcβ1-3Galβ1-4Glc (FDSLNT I), Neu5Acα2-3Galβ1-3 (Neu5Acα2-6)GlcNAcβ1-3Galβ1-4 (Fucα1-3)Glc (FDSLNT II), Neu5Acα2-3Galβ1-4GlcNAcβ1-3Galβ1-4(Fucα1-3)Glc, Neu5Acα2-3Galβ1-4 (Fucα1-3)GlcNAcβ1-3Galβ1-4(Fucα1-3)Glc, Neu5Acα2-3Galβ1-4(Fucα1-3)GlcNAcβ1-3Galβ1-4Glc or salts thereof. The $R^1$-glycosides may be alpha- or beta-anomers. Preferably, said $R^1$-glycosides are the beta-anomers.

In another embodiment within the group of compounds of general formula 1A' and salts thereof the present invention relates to α-2-6-sialylated compounds of general formula 1'-6A and salts thereof.

1'-6A

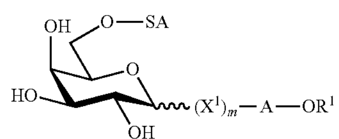

wherein A is a D-glucopyranosyl unit optionally substituted with fucosyl, $X^1$ represents a carbohydrate linker, and integer m is 0 or 1. Group —$OR^1$ is linked to the anomeric carbon ($C_1$) atom of the D-glucopyranosyl ring, preferably in β orientation.

When m is 0, the D-galactopyranosyl unit is directly coupled to group A through an interglycosidic linkage. Preferably, the interglycosidic linkage is a 1-4 linkage thus forming compounds of general formula 1'-6B and salts thereof

1'-6B

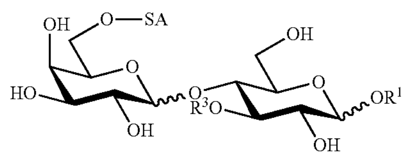

wherein $R^3$ is fucosyl or H. More preferably the interglycosidic linkage between the galactose and the glucose portion is β thus giving rise to a 3'-O-sialyl-lactose derivative. In an even more preferable embodiment aglycon —$OR^1$ is also in β orientation.

When m is 1, the structural element $X^1$, as carbohydrate linker, means a mono-, di-, tri-, tetra-, penta- or oligosaccharide representing a linear or a branched structure. The monosaccharide building units of the carbohydrate linker can be any naturally occurring 5-, 6- or 9-carbon containing sugar derivatives, with the most frequently occurring units being glucose, N-acetyl-glucosamine, galactose, fucose and sialic acid. Preferably, linker $X^1$ is represented by the formula —B—$X^2$— thus forming compounds of general formula 1'-6C and salts thereof.

1'-6C

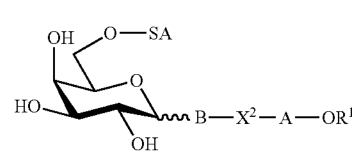

wherein group B is an N-acetyl-glucosaminopyranosyl unit optionally substituted with fucosyl and/or sialyl, and linker $X^2$ means a mono-, di-, tri-, tetra-, penta- or oligosaccharide representing a linear or a branched structure having the monosaccharide building units selected from glucose, N-acetyl-glucosamine, galactose, fucose and sialic acid. Group —$OR^1$ is linked to the anomeric carbon ($C_1$) atom of the D-glucopyranosyl ring, preferably in β orientation. In preference, the sialyl-galactosyl group is attached to group B through 1-3 or 1-4 interglycosidic linkage forming thus a sialyl-lacto-N-biosyl or sialyl-N-acetyl-lactosaminyl terminal trisaccharide moieties, respectively. In a further favoured method, a fucosyl substituent may be coupled to the 3-OH or 4-OH group of unit B and/or to the 3-OH group of unit A, and/or sialyl may be connected to 6-OH of unit B.

In a more preferred embodiment, group $X^2$ in compounds of general formula 1'-6C and salts thereof is galactose optionally substituted with sialyl or oligosaccharide representing a linear or a branched structure having the saccharide building units selected from N-acetyl-lactosamine, lacto-N-biose, fucose and sialic acid, forming thus human milk oligosaccharide derivatives represented by general formula 1'-6D and salts thereof

1'-6D

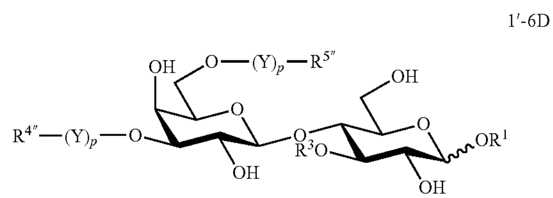

wherein $R^1$ is a group removable by hydrogenolysis, $R^3$ is H or fucosyl unit, Y is independently N-acetyl-lactosaminyl group optionally substituted with a sialyl and/or fucosyl residue, integer p is independently 0, 1 or 2, $R^{4''}$ is selected form the groups characterized by general formulae 3-6 and 4-6, 3-6

4-6

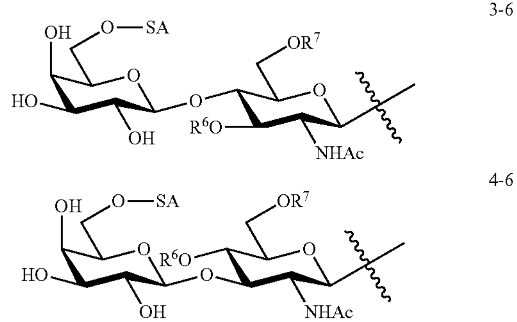

wherein $R^6$ is H or fucosyl residue, $R^7$H or α-sialyl moiety, SA is α-sialyl moiety and $R^{5''}$ is selected from H, α-sialyl moiety, group of general formula 3-6 and group of general formula 4-6.

According to a further preferred method, the compound of general formula 1'-6D and salts thereof as defined above is characterized by its linkages and attached moieties, wherein

- an N-acetyl-lactosaminyl group in group Y (p=2), when attached to another N-acetyl-lactosaminyl group, is coupled with 1-3 interglycosidic linkage,
- the group of general formula 3-6, when attached to Y (p=1, 2), is coupled with 1-3 interglycosidic linkage,
- the group of general formula 4-6, when attached to Y (p=1, 2), is coupled with 1-3 interglycosidic linkage,
- the fucosyl residue if attached to a N-acetyl-lactosaminyl group present in Y is linked to the N-acetyl-glucosamine of the N-acetyl-lactosaminyl group with 1-3 interglycosidic linkage,
- the α-sialyl residue if attached to a N-acetyl-lactosaminyl present in Y is linked to the galactose of the N-acetyl-lactosaminyl group with 2-6 interglycosidic linkage.

In a further aspect, the compound of general formula 1'-6B, 1'-6C or 1'-6D and salts thereof as defined above represents the $R^1$-glycosides of lactose, lacto-N-neotetraose, para-lacto-N-hexaose, para-lacto-N-neohexaose, lacto-N-neohexaose, para-lacto-N-octaose and lacto-N-neooctaose, lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue and having sialyl substituent in 6-OH of a terminal galactosyl residue, and salts thereof. Preferably, the sialyl substituent(s) is/are N-acetyl neuraminyl group(s).

Particularly preferably, the compound of general formula 1'-6B, 1'-6C or 1'-6D and salts thereof as defined above is selected from the group of $R^1$-glycosides of Neu5Acα2-6Galβ1-4Glc (6'-O—(N-acetyl-neuraminosyl)-lactose), Neu5Acα2-6Galβ1-4(Fucα1-3)Glc, Neu5Acα2-6Galβ1-3GlcNAcβ1-3Galβ1-4Glc, Neu5Acα2-6Galβ1-4GlcNAcβ1-3Galβ1-4Glc (LST c), Neu5Acα2-6Galβ1-3(Fucα1-4)GlcNAcβ1-3Galβ1-4Glc, Neu5Acα2-6Galβ1-4(Fucα1-3)GlcNAcβ1-3Galβ1-4Glc, Neu5Acα2-6Galβ1-3GlcNAcβ1-3Galβ1-4(Fucα1-3)Glc, Neu5Acα2-6Galβ1-3(Fucα1-4)GlcNAcβ1-3Galβ1-4(Fucα1-3)Glc, Neu5Acα2-6Galβ1-3(Neu5Acα2-6)GlcNAcβ1-3Galβ1-4Glc, Neu5Acα2-6Galβ1-3(Neu5Acα2-6)(Fucα1-4)GlcNAcβ1-3Galβ1-4Glc, Neu5Acα2-6Galβ1-3(Neu5Acα2-6)GlcNAcβ1-3Galβ1-4(Fucα1-3)Glc, Neu5Acα2-6Galβ1-4GlcNAcβ1-3Galβ1-4(Fucα1-3)Glc (FLST c), Neu5Acα2-6Galβ1-4(Fucα1-3)GlcNAcβ1-3Galβ1-4(Fucα1-3)Glc, Neu5Acα2-6Galβ1-4(Fucα1-3)GlcNAcβ1-3Galβ1-4Glc or salts thereof. The $R^1$-glycosides may be alpha- or beta-anomers. Preferably, said $R^1$-glycosides are the beta-anomers.

Other features of the invention will become apparent in the course of the following descriptions of exemplary embodiments which are given for illustration of the invention and are not to be limiting thereof.

EXPERIMENTAL

1. Synthesis of Sialyl Acceptors

A) General procedure: lactose (5 g, 14.6 mmol) and TsOH.$H_2O$ (0.2 g, 1.05 mmol) were added in one portion to a mixture of DMF (20 ml) and benzaldehyde dimethyl acetal (5.5 ml, 35.4 mmol, 2.4 eq.) at room temperature. The reaction mixture was stirred strongly at 70° C. under exclusion of humidity for 1 hour. After cooling triethyl amine (0.15 ml) was added then the volatile components (MeOH, triethyl amine, remaining benzaldehyde dimethyl acetal) were removed in vacuo. To the reaction mixture the benzyl bromide derivative (1.5 eq.)—predissolved in 5-10 ml of DMF, if the reagent is a solid—was added and the mixture was cooled to 0° C. for 20 min. Still under cooling NaH (0.8 g of a 55% dispersion on mineral oil, 1.3 eq.) was added in one portion and the mixture was stirred under cooling until the hydrogen formation stopped then at room temperature for 2-3 hours. Methanol (2 ml) was added carefully and the reaction was stirred for a further 5 min. The reaction mixture was portioned between 100 ml of DCM and 100 ml of water and extracted. The water layer was back-extracted twice with 100 ml of DCM. The combined organic phases were evaporated, the residue was dissolved in 100 ml of acetonitrile and extracted with 100 ml of hexane. The acetonitrile was distilled off and the residue was taken up in isopropanol (10 ml) and isopropyl ether (50 ml) at 50° C. The clear solution was cooled to −20° C. for or overnight. The crystals obtained were filtered off and washed twice with TBME and dried. Recrystallization may be carried out from a mixture of TBME (~50 ml) and ethanol (~20 ml).

4-Chlorobenzyl 4',6'-O-benzylidene-β-lactoside

Yield: 1.71 g

4-Methylbenzyl 4',6'-O-benzylidene-β-lactoside

Yield: 3.20 g

3-Phenylbenzyl 4',6'-O-benzylidene-β-lactoside

Yield: 2.70 g

2-Naphthylmethyl 4',6'-O-benzylidene-β-lactoside

Yield: 1.77 g

B) To a mixture of one of the above benzylidene acetals (500 mg) in methanol (10 ml) and water (0.5 ml) TFA was added at room temperature and the reaction mixture was stirred for 2-4 hours under exclusion of humidity then evaporated. The remaining material was co-evaporated with ethanol 3-4 times giving a crude solid, which, after drying, may be recrystallized from a mixture of methanol (~10-35 ml) and water (~0-2 mL).

4-Chlorobenzyl β-lactoside

Yield: 333 mg $^{13}$C-NMR (75.1 MHz, $D_2O$): δ=135.25, 133.67, 130.30, 128.70, 103.00, 101.13, 78.39, 75.44, 74.89, 74.49, 72.88, 72.58, 71.03, 70.83, 68.62, 61.11, 60.13.

4-Methylbenzyl β-lactoside

Yield: 439 mg $^{13}$C-NMR (75.1 MHz, $D_2O$): δ=138.91, 133.50, 129.37, 129.07, 103.01, 100.96, 78.43, 75.44, 74.87, 74.52, 72.90, 72.59, 71.47, 71.03, 68.63, 61.11, 60.17, 20.34.

3-Phenylbenzyl β-lactoside

Yield: 438 mg $^{13}$C-NMR (75.1 MHz, $d_6$-DMSO/$d_4$-MeOH/$D_2O$ 8:1:1): δ=140.29, 140.24, 138.88, 129.13, 129.02, 127.66, 126.88, 126.83, 126.03, 125.90, 103.95, 102.03, 80.76, 75.65, 75.07, 75.00, 73.34, 73.28, 70.66, 69.81, 68.27, 60.56.

2-Naphthylmethyl β-lactoside

Yield: 378 mg $^{13}C$-NMR (75.1 MHz, $D_2O/d_6$-DMSO): δ=134.96, 133.24, 133.12, 128.59, 128.31, 128.08, 127.46, 126.98, 126.90, 126.79, 103.26, 101.59, 78.89, 75.62, 75.09, 74.81, 73.14, 72.81, 71.33, 71.14, 68.75, 61.22, 60.39.

C)

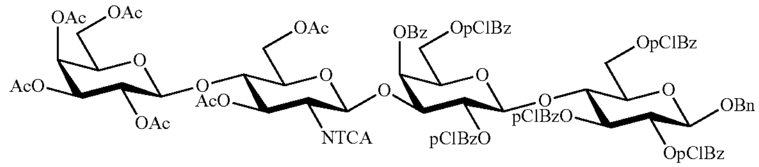

10 g (8.13 mmol) of benzyl 2,3,6,2',6'-penta-O-(4-chlorobenzoyl)-4'-O-benzoyl-β-lactoside and 10 g (1.6 equiv.) of methyl N-trichloroacetyl-3,6,2',3',4'6'-hexa-O-acetyl-1-thiolactosaminide were dissolved in 35 ml of dry $CHCl_3$ under argon. To this solution 3.7 g of NIS and 490 mg of AgOTf were added at rt, and the stirring was continued for approx. 20 min. Triethyl amine (5 ml) was added to the slurry, diluted with $CH_2Cl_2$ (500 ml) and then extracted 2× with sodium thiosulphate solution (10%), the organic phase was separated, dried with $MgSO_4$, filtered, concentrated, and the syrup was chromatographed on a column of silica-gel, using a gradient of $CH_2Cl_2$: acetone 98:2→95:5. Yield: 12.7 g, 80%. MS (ESP): 1972.1 $[M+Na]^+$, 1988.1 $[M+K]^+$, 1948.2 $[M-H]^-$, 1984.0 $[M+Cl]^-$. $^{13}C$ NMR ($CDCl_3$) δ: 101.2, 100.7, 100.0, 98.8 (anomeric carbons).

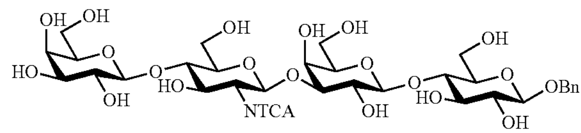

10 g (5.1 mmol) of tetrasaccharide prepared above was dissolved in MeOH (110 ml) and a solution of NaOMe (1 M in MeOH) was added until pH 10 was attained. The solution was stirred at 40° C. for 5 h, then was neutralized by addition of Amberlite IR 120H$^+$ resin, the resin was filtered off, and the filtrate was evaporated to dryness. The residue was dissolved in warm DMF (10 ml) and added dropwise to $^iPr_2O$ (150 ml) and the suspension was stirred for an additional 3 h. The precipitate was filtered off, washed with $^iPr_2O$ (2×20 ml) and dried to yield 4.2 g of product as off-white powder (91%). MS (ESP): 900.1 $[M-H]^-$. $^{13}C$ NMR ($D_2O$) δ: 105.6, 105.5, 104.2, 103.7 (anomeric carbons).

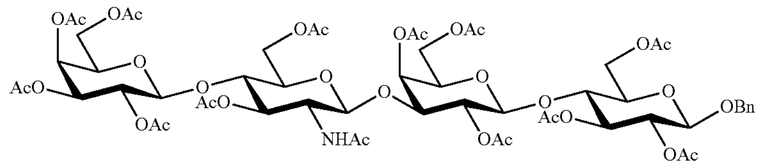

35 g of a compound of the tetrasaccharide prepared above was dissolved in 110 ml of MeOH and 110 ml of aqueous KOH (7.5 g) solution and the mixture was stirred at rt. for id. The mixture was then chilled with an ice-bath, neutralized by HCl-gas and concentrated to dryness. The resulting crude brown glass was then acetylated with pyridine (150 ml) and acetic anhydride (150 ml) at rt. for 1 d. The solution was concentrated, the syrup was dissolved in $CH_2Cl_2$, the organic phase was extracted with 1M HCl-solution and then with sat. $NaHCO_3$-solution, dried with $MgSO_4$, filtered and concentrated to yield 43 g of brown foam, which was subjected to column chromatography using $CH_2Cl_2$:acetone 8:2 as eluent. $^{13}C$ NMR ($CDCl_3$) δ: 101.2, 100.8, 100.4, 99.2 (anomeric carbons).

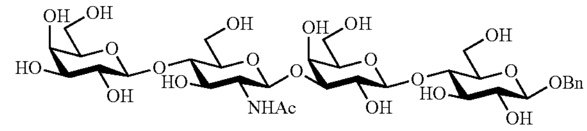

140 g (107.5 mmol) of the peracetylated tetrasaccharide prepared above was dissolved in 1.5 L of MeOH, NaOMe-solution (1M) was added until pH 10, and the mixture was stirred at 50° C. overnight. The product crystallized from the reaction mixture. The mixture is allowed to cool to rt., then it was chilled, filtered, the filtrate was washed with cold EtOH, then dried to yield 69 g of benzyl β-LNnT as a white powder (86.5 mmol, 80%). $^{13}C$ NMR ($D_2O$) δ: 105.6, 105.5, 105.4, 103.6 (anomeric carbons). Mp. 284-286° C.

D) General Procedure for the Preparation of a Neutral HMO Benzyl/Substituted Benzyl Glycoside A selected neutral HMO (1 equiv.) was dissolved/suspended in 1-10 volumes (g/mL) of DMF, DMSO or a mixture thereof. The reaction mixture was cooled to 0° C. and benzyl bromide/substituted benzyl bromide (1.2-1.4 equiv.) was added. A strong base such as sodium hydride, potassium hydride, calcium hydride, potassium t-butoxide, sodium t-butoxide (1.2-1.4 equiv) was added at 0-40° C. and the reaction mixture was stirred for 6-24 hours at 0-60° C. Subsequently, water was added to quench the excess of base and the reaction mixture was stirred at RT for 30 minutes. The resulting reaction mixture was concentrated and purified in reverse phase chromatography, silica gel chromatography, ion-exchange chromatography, size-exclusion chromatography, etc. or crystallized giving rise to the desired benzylated/substituted benzylated neutral HMO compound in 70-80% yields.

1-O-β-(4-methylbenzyl)-LNnT $^1$H NMR ($D_2O$): 7.3 (dd, 4H), 4.88 (d, 1H), 4.7 (m), 4.54 (d, 1H), 4.48 (d, 1H), 4.42 (d, 1H), 4.34 (d), 4.0-3.5 (m), 3.34 (dd, 1H).

$^{13}$C NMR ($D_2O$): 184.2, 177.6, 173.7, 141.5, 136.1, 131.9, 131.4, 105.6, 105.5, 105.4, 103.6, 93.2, 84.7, 81.5, 81.0, 80.8, 78.0, 77.6, 77.4, 77.1, 75.5, 75.2, 74.8, 74.0, 73.6, 72.9, 63.7, 62.8, 58.9, 56.4, 25.9, 22.9.

1-O-β-(4-chlorobenzyl)-LNnT $^1$H NMR ($D_2O$): 7.4 (s, 4H), 4.9 (d, 1H), 4.72 (m), 4.52 (d, 1H), 4.8 (d, 1H), 4.42 (d, 1H), 4.16 (d, 1H), 4.0-3.52 (m).

$^{13}$C NMR ($D_2O$): 138.9, 177.6, 138.3, 137.9, 136.2, 131.3, 105.6, 105.5, 105.4, 103.7, 93.2, 86.1, 84.7, 81.5, 81.0, 80.8, 78.0, 77.5, 77.4, 77.2, 77.1, 75.5, 75.2, 74.9, 63.7, 58.9, 57.8, 56.4, 24.8.

1-O-β-benzyl-LNT $^1$H-NMR ($D_2O$, 400 MHz) δ 2.03 (s, 3H, C$\underline{H}_3$CONH), 3.35 (dd, 1H, J=8.1 8.5 Hz, H-2), 3.49 (m, 1H, H-5"), 3.53 (m, H-2"), 3.65 (m, 1H, H-3'"), 3.57 (dd, 1H, J=8.1 9.0 Hz, H-4"), 3.58 (m, 1H, H-5), 3.59 (dd, 1H, J=7.7 10.0 Hz, H-2'), 3.62 (m, 1H, H-3), 3.63 (m, 1H, H-4), 3.71 (m, 1H, H-5'), 3.71 (m, 1H, H-5'"), 3.73 (dd, 1H, J=3.3 10.0 Hz, H-3'), 3.76 (m, 2H, H-6ab'"), 3.76 (m, 2H, H-6ab'), 3.80 (m, 1H, H-6a"), 3.80 (dd, 1H, J=5.0 12.2 Hz, H-6a), 3.82 (dd, 1H, J=8.1 10.5 Hz, H-3"), 3.90 (m, 1H, H-6b"), 3.90 (dd, 1H, J=8.4 10.5 Hz, H-2"), 3.92 (d, 1H, J=3.3 Hz, H-4"), 3.98 (dd, 1H, J=1.6 12.2 Hz, H-6b), 4.15 (d, 1H, J=3.3 Hz, H-4'), 4.44 (d, 1H, J=7.7 Hz, H-1'), 4.45 (d, 1H, J=7.7 Hz, H-1'"), 4.56 (d, 1H, J=8.1 Hz, H-1), 4.73 (d, 1H, J=8.4 Hz, H-1'), 4.76 (d, 1H, J=11.7 Hz, C$\underline{H}_2$Ph), 4.94 (d, 1H, J=11.7 Hz, C$\underline{H}_2$Ph), 7.40-7.50 (m, 5H, Ph).

$^{13}$C-NMR ($D_2O$, 100 MHz) δ 24.9 (C$\underline{H}_3$CONH), 57.4 (C-2"), 62.8 (C-6), 63.2 (C-6"), 63.7 (C-6'"), 63.7 (C-6'), 71.0 (C-4'), 71.2 (C-4'"), 71.3 (C-4"), 72.7 (C-2'), 73.4 (C-2'"), 74.2 ($\underline{C}H_2$Ph), 75.2 (C-3'"), 75.5 (C-2), 77.1 (C-3), 77.5 (C-5'), 77.6 (C-5'"), 77.9 (C-5), 78.0 (C-5"), 81.1 (C-4), 84.7 (C-3'), 84.8 (C-3"), 103.7 (C-1), 105.3 (C-1"), 105.6 (C-1'), 106.2 (C-1'"), 131.1 (Ph), 131.4 (2C, Ph), 131.5 (2C, Ph), 139.2 (Ph), 177.7 ($CH_3\underline{C}$ONH).

M.p. 245° C. (dec.). $[\alpha]_D^{22}$=−10.3 (c=1, $H_2O$).

1-O-β-(4-methylbenzyl)-LNT $^1$H-NMR ($D_2O$, 300 MHz) δ 1.97 (s, 3H), 2.29 (s, 3H), 3.27 (dd, 1H, J=8.1 8.5 Hz), 3.39-3.87 (m, 21H), 3.92 (dd, 1H, J=1.8 12.3 Hz), 4.09 (d, 1H, J=3.3 Hz), 4.37 (d, 1H, J=8.1 Hz), 4.38 (d, 1H, J=7.8 Hz), 4.47 (d, 1H, J=8.1 Hz), 4.65 (d, 1H, J=11.7 Hz), 4.67 (d, 1H, J=8.1 Hz), 4.83 (d, 1H, J=11.7 Hz), 7.22 (d, 2H, J=8.1 Hz), 7.30 (d, 2H, J=8.1 Hz).

$^{13}$C-NMR ($D_2O$, δ5.4 MHz) δ 23.1, 25.0, 57.7, 62.8, 63.2, 63.7, 63.8, 71.0, 71.1, 71.3, 72.7, 73.4, 74.1, 75.2, 75.5, 77.1, 77.5, 77.6, 77.9, 78.0, 81.1, 84.7, 84.8, 103.6, 105.3, 105.7, 106.2, 131.7 (2C), 132.0 (2C), 136.2, 141.5, 177.7.

2. Trans-Sialylation Reactions

General procedure: a solution of 2-O-(p-nitrophenyl)-α-D-sialoside (25 mmol) and the appropriate sialyl acceptor (35 mmol) in degassed incubation buffer (1.0 m, 100 mM Tris/HCl, pH 7.5, 50 mg BSA, 0.02% $NaN_3$) was incubated with recombinant transsialidase from *T. cruzi* (80 μl, 1.3 mg/ml) at 23° C. for 24 h. The reaction was monitored by TLC (butanol/acetic acid/water 5:2:2). After completion, the enzyme was denatured and centrifuged before the supernatant is lyophilized. The dry residue was dissolved in water and purified by biogel chromatography (P-2 Biogel, 16×900 mm) with water or by reverse phase chromatography. The yields vary between 45-85%.

4-Chlorobenzyl 3'-O—(N-acetyl-neuraminosyl)-β-lactoside $^1$H-NMR (500 MHz, $D_2O$): δ [ppm]=7.46-7.42 (m, 4H, $H_{(a/b)arom}$); 4.91 (d, 1H, $CH_2$a-Bn); 4.74 (d, 1H, $CH_2$b-Bn); 4.55-4.52 (m, 2H, H-1/H-1'); 4.11 (dd, 1H, H-3'); 2.76 (dd, 1H, H-3"$_{eq}$); 2.04 (s, 3H, $COCH_3$); 1.81 (dd, 1H, H-3"$_{ax}$).

$J_{(a,b)-Bn}$=11.8; $J_{2',3'}$=9.9; $J_{3',4'}$=2.9; $J_{3''ax,3''eq}$=12.4; $J_{3''ax,4''}$=12.1; $J_{3''eq,4''}$=4.5 Hz.

$^{13}$C-NMR (126 MHz, $D_2O$): δ [ppm]=135.2, 133.5 (quart. $C_{arom}$); 130.2 ($CH_{a-arom}$); 128.6 ($CH_{b-arom}$); 102.6 (C-1'); 101.1 (C-1); 51.7 (C-5"); 39.6 (C-3"); 22.0 ($COCH_3$).

4-Methylbenzyl 3'-O—(N-acetyl-neuraminosyl)-β-lactoside $^1$H-NMR (500 MHz, $D_2O$): δ [ppm]=7.36 (d, 2H, H-$a_{arom}$); 7.28 (d, 2H, H-$b_{arom}$); 4.89 (d, 1H, $CH_2$a-Bn); 4.72 (d, 1H, $CH_2$b-Bn); 4.54-4.52 (m, 2H, H-1/H-1'); 4.12 (dd, 1H, H-3'); 2.76 (dd, 1H, H-3"$_{eq}$); 2.35 (s, 3H, $CH_3$-Tol); 2.04 (s, 3H, $COCH_3$), 1.81 (dd, 1H, H-3"$_{ax}$).

$J_{(a,b)arom}$=7.9; $J_{(a,b)-Bn}$ 11.5; $J_{2',3'}$=9.9; $J_{3',4'}$=3.0; $J_{3''ax,3''eq}$=12.5; $J_{3''ax,4''}$=12.2; $J_{3''eq,4''}$=4.6 Hz.

$^{13}$C-NMR (126 MHz, $D_2O$): δ [ppm]=138.8, 133.4 (quart. $C_{arom}$); 129.3 ($CH_{a-arom}$); 129.0 ($CH_{b-arom}$); 102.6 (C-1'); 100.9 (C-1); 99.8 (C-2"), 51.7 (C-5"); 39.6 (C-3"); 22.0 ($COCH_3$); 20.2 ($CH_3$-Tol).

2-Naphthylmethyl 3'-O—(N-acetyl-neuraminosyl)-β-lactoside $^1$H-NMR (500 MHz, $D_2O$): δ [ppm]=7.99-7.97 (m, 4H, H-arom); 7.62-7.59 (m, 3H, H-arom); 5.10 (d, 1H, $CH_2$a-Bn); 4.95 (d, 1H, $CH_2$b-Bn); 4.60 (d, 1H, H-1); 4.53 (d, 1H, H-1'); 4.12 (dd, 1H, H-3'); 2.77 (dd, 1H, H-3"$_{eq}$); 2.04 (s, 3H, $COCH_3$); 1.81 (dd, 1H, H-3"$_{ax}$).

$J_{(a,b)-Bn}$=11.9; $J_{1,2}$=8.0; $J_{1',2'}$=7.9; $J_{2',3'}$=9.9; =3.0; $J_{3''ax,3''eq}$=12.5; $J_{3''ax,4''}$=12.1; $J_{3''eq,4''}$=4.6 Hz.

$^{13}$C-NMR (126 MHz, $D_2O$): δ [ppm]=128.3, 127.9, 127.7, 127.6, 126.6, 126.5 ($CH_{arom}$); 102.6 (C-1'); 101.1 (C-1); 51.7 (C-5"); 22.0 ($COCH_3$).

3-Phenylbenzyl 3'-O—(N-acetyl-neuraminosyl)-β-lactoside $^1$H-NMR (400 MHz, $D_2O$): δ [ppm]=7.75-7.44 (m, 9H, H-arom); 4.99 (d, 1H, $CH_2$a-Bn); 4.82 (d, 1H, $CH_2$b-Bn); 4.57 (d, 1H, H-1); 4.53 (d, 1H, H-1'); 4.13 (dd, 1H, H-3'); 2.78 (dd, 1H, H-3"$_{eq}$); 2.05 (s, 3H, $COCH_3$); 1.82 (dd, 1H, H-3"$_{ax}$).

$J_{(a,b)-Bn}$=11.8; $J_{1,2}$=8.0; =7.9; $J_{2',3'}$=9.9; $J_{3',4'}$=3.1; $J_{3''ax,3''eq}$=12.5; $J_{3''ax,4''}$=12.0; $J_{3''eq,4''}$=4.6 Hz.

$^{13}$C-NMR (100 MHz, $D_2O$): δ [ppm]=140.9, 140.3, 137.5 (quart. $C_{arom}$); 129.4, 129.2, 127.9, 127.8, 127.1, 127.0, 126.9, ($CH_{arom}$); 102.7 (C-1'); 101.2 (C-1); 99.6 (C-2"); 51.8 (C-5"); 39.7 (C-3"); 22.1 ($COCH_3$).

Benzyl 3'"-O—(N-acetyl-neuraminosyl)-β-LNnT $^1$H-NMR (400 MHz, $D_2O$): see FIG. 1.

The invention claimed is:

1. Method for the synthesis of compounds of human milk oligosaccharides of Formula 1-3D and salts thereof 1-3D

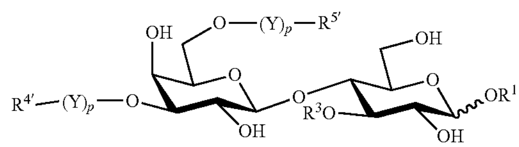

wherein Y is independently an N-acetyl-lactosaminyl group optionally substituted with a sialyl and/or fucosyl residue, integer p is independently 0, 1 or 2, $R^{4'}$ is selected from Formulae 3-3 or 4-3, 3-3

4-3

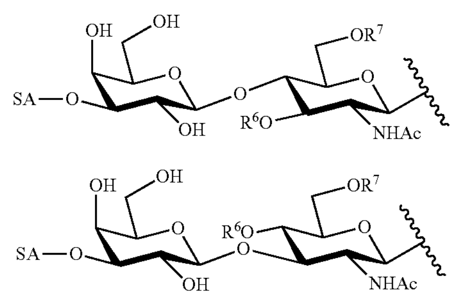

wherein $R^6$ is H or fucosyl residue, $R^7$H or α-sialyl moiety, SA is α-sialyl moiety, and $R^{5'}$ is selected from the group consisting of H, α-sialyl moiety, a group of Formula 3-3, and a group of Formula 4-3;

wherein $R^1$ is a protecting group that is removable by hydrogenolysis, in which a sialyl donor of formula SA-$OR^2$ and salts thereof, wherein $R^2$ is a mono-, di- or oligosaccharide, glycolipid, glycoprotein or glycopeptide, cyclic or acyclic aliphatic group, or aryl residue, and SA is an α-sialyl moiety, is reacted with a sialyl acceptor of Formula 2D and salts thereof

2D

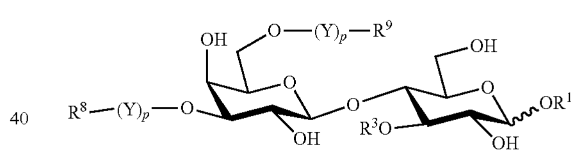

wherein $R^1$ is as defined above and is a group removable by hydrogenolysis, in which a sialyl donor of formula SA-$OR^3$ is H or fucosyl unit, Y is independently an N-acetyl-lactosaminyl group optionally substituted with a sialyl and/or fucosyl residue, p is an integer independently selected from 0, 1 or 2, $R^8$ is selected form Formulae 5 or 6,

5

6

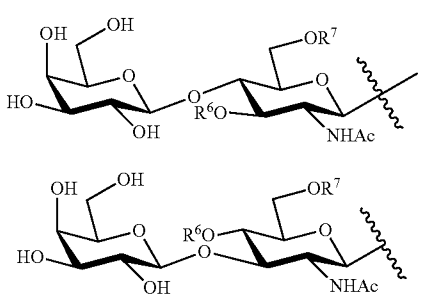

wherein $R^6$ is H or fucosyl residue, $R^7$H or α-sialyl moiety, and $R^9$ is selected from the group consisting of H, α-sialyl moiety, a group of Formula 5 and a group of Formula 6, under the catalysis of an enzyme having transsialidase activity.

2. The method according to claim 1, wherein the enzyme having transsialidase activity is selected from sialidases derived from *Bifidobacterium* species and transsialidases derived from *Trypanosoma cruzi*.

3. The method according to claim 1, wherein the enzyme having transsialidase activity is an engineered enzyme.

4. The method according to claim 1, wherein the sialyl donor is selected from the group consisting of 2-O-(p-nitrophenyl)-α-D-sialoside, 2-O-(4-methylumbelliferyl)-α-D-sialoside, fetuin and 3'-O-sialyl-lactose.

5. The method according to claim 1, wherein $R_1$ is selected from the group consisting of benzyl or 2-naphthylmethyl groups optionally substituted with at least one group selected from the group consisting of phenyl, alkyl or halogen.

6. Method for the synthesis of compounds selected from the group consisting of $R^1$-glycosides of Neu5Acα2-3Galβ1-4(Fucα1-3)Glc (3-O-fucosyl-3'-O-(N-acetyl-neuraminosyl)-lactose), Neu5Acα2-3Galβ1-3GlcNAcβ1-3Galβ1-4Glc (LST a), Neu5Acα2-3Galβ1-GlcNAcβ1-3Galβ1-4Glc, Neu5Acα2-3Galβ1-3(Fucα1-4)GlcNAcβ1-3Galβ1-4Glc (FLST a), Neu5Acα2-3Galβ1-4(Fucα1-3)GlcNAcβ1-3Galβ1-4Glc, Neu5Acα2-3Galβ1-3GlcNAcβ1-3Galβ1-4(Fucα1-3)Glc, Neu5Acα2-3Galβ1-3(Fucα1-4)GlcNAcβ1-3Galβ1-4(Fucα1-3)Glc, Neu5Acα2-3Galβ1-3(Neu5Acα2-6)GlcNAcβ1-3Galβ1-4Glc (DSLNT), Neu5Acα2-3Galβ1-3(Neu5Acα2-6)(Fucα1-4)GlcNAcβ1-3Galβ1-4Glc (FDSLNT I), Neu5Acα2-3Galβ1-3(Neu5Acα2-6)GlcNAcβ1-3Galβ1-4(Fucα1-3)Glc (FDSLNT II), Neu5Acα2-3Galβ1-4GlcNAcβ1-3Galβ1-4(Fucα1-3)Glc, Neu5Acα2-3Galβ1-4(Fucα1-3)GlcNAcβ1-3Galβ1-4(Fucα1-3)Glc, Neu5Acα2-3Galβ1-4(Fucα1-3)GlcNAcβ1-3Galβ1-4Glc and salts thereof wherein $R^1$ is a protecting group that is removable by hydrogenolysis, in which a sialyl donor of formula SA-$OR^2$ and salts thereof, wherein $R^2$ is a mono-, di- or oligosaccharide, glycolipid, glycoprotein or glycopeptide, cyclic or acyclic aliphatic group, or aryl residue, and SA is an α-sialyl moiety, is reacted with a sialyl acceptor selected from the group of $R^1$-glycosides of Galβ1-4(Fucα1-3)Glc (3-O-fucosyllactose), Galβ1-3GlcNAcβ1-3Galβ1-4Glc (LNT), Galβ1-4GlcNAcβ1-3Galβ1-4Glc (LNnT), Galβ1-3(Fucα1-4)GlcNAcβ1-3Galβ1-4Glc (LNFP II), Galβ1-4(Fucα1-3)GlcNAcβ1-3Galβ1-4Glc (LNFP III), Galβ1-3GlcNAcβ1-3Galβ1-4(Fucα1-3)Glc (LNFP V), Galβ1-3(Fucα1-4)GlcNAcβ1-3Galβ1-4(Fucα1-3)Glc (LNDFH II), Galβ1-3(Neu5Acα2-6)GlcNAcβ1-3Galβ1-4Glc (LSTb), Galβ1-3(Neu5Acα2-6)(Fucα1-4)GlcNAcβ1-3Galβ1-4Glc, Galβ1-3(Neu5Acα2-6)GlcNAcβ1-3Galβ1-4(Fucα1-3)Glc, Galβ1-4GlcNAcβ1-3Galβ1-4(Fucα1-3)Glc, Galβ1-4(Fucα1-3)GlcNAcβ1-3Galβ1-4(Fucα1-3)Glc (LNDFH III), or salts thereof, under the catalysis of an enzyme having transsialidase activity.

7. The method according to claim 6, wherein $R_1$ is selected from the group consisting of benzyl or 2-naphthylmethyl groups optionally substituted with at least one group selected from the group consisting of phenyl, alkyl or halogen.

8. The method according to claim 6, wherein the enzyme having transsialidase activity is selected from sialidases derived from *Bifidobacterium* species and transsialidases derived from *Trypanosoma cruzi*.

9. The method according to claim 6, wherein the enzyme having transsialidase activity is an engineered enzyme.

10. The method according to claim 6, wherein the sialyl donor is selected from the group consisting of 2-O-(p-nitrophenyl)-a-D-sialoside, 2-O-(4 methylumbelliferyl)-α-D-sialoside, fetuin and 3'-O-sialyl-lactose.

* * * * *

UNITED STATES PATENT AND TRADEMARK OFFICE

CERTIFICATE OF CORRECTION

PATENT NO. : 9,102,966 B2
APPLICATION NO. : 13/809794
DATED : August 11, 2015
INVENTOR(S) : Andreas Schroven et al.

It is certified that error appears in the above-identified patent and that said Letters Patent is hereby corrected as shown below:

On Title Page, Item (73) Assignee
replace "KGS, Lyngby (DK)"
with --Kgs. Lyngby (DK)--.

On Title Page, Item (56), References Cited, Other Publications, Line 29
replace "055:1-17"
with --055:H7"--.

Signed and Sealed this
Fifth Day of April, 2016

Michelle K. Lee
*Director of the United States Patent and Trademark Office*